US008017126B2

(12) United States Patent
Quinnan et al.

(10) Patent No.: US 8,017,126 B2
(45) Date of Patent: Sep. 13, 2011

(54) MODIFIED HIV-1 ENVELOPE PROTEINS

(75) Inventors: Gerald Quinnan, Rockville, MD (US); Fatim Cham, Garmantown, MD (US); Guido Van Der Groen, Kontich (BE)

(73) Assignees: Henry M. Jackson Foundation for the Advanvement of Military Medicine Inc., Rockville, MD (US); Prince Leopoid Institute of Trtopical Medicine, Antwerp (BE)

( * ) Notice: Subject to any disclaimer, the term of this patent is extended or adjusted under 35 U.S.C. 154(b) by 535 days.

(21) Appl. No.: 11/661,210

(22) PCT Filed: Aug. 29, 2005

(86) PCT No.: PCT/US2005/030563
§ 371 (c)(1), (2), (4) Date: Oct. 28, 2008

(87) PCT Pub. No.: WO2006/026508
PCT Pub. Date: Mar. 9, 2006

(65) Prior Publication Data
US 2009/0232830 A1 Sep. 17, 2009

Related U.S. Application Data

(60) Provisional application No. 60/604,802, filed on Aug. 27, 2004.

(51) Int. Cl.

| | |
|---|---|
| *A61K 39/21* | (2006.01) |
| *C07H 21/04* | (2006.01) |
| *C12N 15/00* | (2006.01) |
| *C12N 5/00* | (2006.01) |
| *C12N 1/20* | (2006.01) |
| *C12N 15/09* | (2006.01) |

(52) U.S. Cl. ............... 424/188.1; 424/208.1; 536/23.72; 435/320.1; 435/325; 435/252.3; 435/69.3

(58) Field of Classification Search ........................ None
See application file for complete search history.

(56) References Cited

FOREIGN PATENT DOCUMENTS

WO WO 00/58438 10/2000

OTHER PUBLICATIONS

Mateu et al. Non-additive effects of multiple amino acid substitutions on antigen-antibody recognition. European Journal of Immunology 1992, vol. 22, pp. 1385-1389.*
Greenspan et al. Defining epitopes: Its not as easy as it seems. Nature Biotechnology Oct. 1999, vol. 17, pp. 936-937.*
Tumanova et al. Construction of Peptides Mimicking a HIV-1 gp41 Epitope Recognized by Virus-Neutralizing Antibodies 2F5. Molecular Biology 2001, vol. 35, No. 1, pp. 130-133.*
Conley et al. Neutralization of divergent human immunodeficiency virus type 1 variants and primary isolates by IAM-41-2F5, an anti-gp41 human monoclonal antibody. Proceedings from the National Academy of Science, U.S.A, Apr. 1994, vol. 91, pp. 3348-3352.*
Burton et al. HIV vaccine design and the neutralizing antibody problem. Nature Immunology, Mar. 2004, vol. 5 No. 3, p. 233-236.*
Feinberg et al. AIDS vaccine models: Challenging challenge viruses. Nature Medicine, Mar. 2002, vol. 8, No. 3, pp. 207-210.*
Klein et al. Examination of the contributions of size and avidity to the neutralization mechanisms of the anti-HIV antibodies b12 and 4E10. Proceedings of the National Academy of Sciences of the United States of America Apr. 16, 2009, electronic publication Early Edition.*
Letvin. Progress toward an HIV vaccine. Annual Review of Medicine 2005, vol. 56, p. 213-223.*
Puls et al. Therapeutic vaccination against HIV: current progress and future possibilities. Clinical Science 2006, vol. 110, p. 59-71.*
Yee et al. Prospects for gene therapy using HIV-based vectors. Somatic Cell and Molecular Genetics, Nov. 2001, vol. 26, No. 1/6, pp. 159-174.*
Broder et al. (1994). Antigenic implications of human immunodeficiency virus type 1 envelope quaternary structure: Oligomer-specific and -sensitive monoclonal antibodies. Proc. Natl. Acad. Sci. USA 91, 11699-703.
Dong et al. (2003). Induction of Primary Virus-Cross-Reactive Human Immunodeficiency Virus Type 1- Neutralizing Antibodies in Small Animals by Using an Alphavirus-Derived In Vivo Expression System. J. Virol. 77, 3119-30.
Earl et al. (1994). Native Oligomeric Human Immunodeficiency Virus Type 1 Envelope Glycoprotein Elicits Diverse Monoclonal Antibody Reactivities J. Virol. 68, 3015-26.
Garrity et al. (1997). Refocusing Neutralizing Antibody Response by Targeted Dampening of an Immunodominant Epitope. J. Immun. 159, 279-289.
Javaherian et al. (1989). Principal neutralizing domain of the human immunodeficiency virus type 1 envelope protein. Proc. Natl. Acad. Sci. USA 86, 6768-72.
Mascola et al. (1999). Protection of Macques against Simian/Human Immunodeficiency Virus 89.6PD by Passive Transfer of Neutralizing Antibodies. J. Virol. 73, 4009-18.
Mascola et al. (2000). Protection of macques against vaginal transmission of a pathogenic HIV-1/SIV chimeric virus by passive infusion of neutralizing antibodies. Nat. Med. 6, 207-10.
Quinnan (1997). Antiviral Agents and Diseases of Man, Raven Press, 791-833.
Quinnan et al. (1998). Evolution of Neutralizing Antibody Response Against HIV Type 1 Virions and Pseudovirus in Multicenter AIDS Cohort Study Participants. AIDS Res. Hum. Retroviruses 14, 939-49.
Quinnan et al. (1999). Expression and Characterization of HIV Type 1 Envelope Protein Associated with a Broadly reactive Neutralizing Antibody Response, AIDS Res. Hum. Retroviruses 15, 561-70.
Trkola et al. (1995). Cross-Clade Neutralization of Primary Isolate of Human Immunodeficiency Virus Type-1 by Human Monoclonal Antibodies and Tetrameric CDA-IgG. J. Virol. 69, 6609-17.

(Continued)

*Primary Examiner* — Jeffrey Parkin
*Assistant Examiner* — Louise Humphrey
(74) *Attorney, Agent, or Firm* — Morgan, Lewis & Bockius LLP

(57) ABSTRACT

The present invention relates to modified HIV-1 envelope proteins which express epitopes that produce a broadly cross reactive neutralizing response, their methods of use and antibodies which bind to these epitopes.

16 Claims, 7 Drawing Sheets

OTHER PUBLICATIONS

Zhang et al. (2002). A variable Region 3 (V3) Mutation Determines a Global Neutralization Phenotype and CD4-Independent Infectivity of a Human Immunodeficiency Virus Type 1 Envelope Associated with a Broadly Cross-Reactive, Primar Virus-Neutralizing Antibody Response. J. Virol. 76, 644-55.

Yang et al., "Genetic diversity and high proportion of intersubtype recombinants among HIV type 1-infected pregnant women in Kisumu, western Kenya," AIDS Res. Hum. Retroviruses, 2004, 20(5):565-574.

Carr et al., "Diverse BF recombinants have spread widely since the introduction of HIV-1 into South America," AIDS, 2001, 15(15):F41-F47.

Conley et al., "Neutralization of divergent human immunodeficiency virus type 1 variants and primary isolates by IAM-41-2F5, an anti-gp41 human monoclonal antibody," Proc. Natl. Acad. Sci. USA, 1994, 91(8):3348-3352.

Cham et al., "Neutralization and infectivity characteristics of envelope glycoproteins from human immunodeficiency virus type 1 infected donors whose sera exhibit broadly cross-reactive neutralizing activity," Virology, 2006, 347(1):36-51.

Zhang et al., "Broadly cross-reactive HIV neutralizing human monoclonal antibody Fab selected by sequential antigen panning of a phage display library," J. Immunol. Methods, 2003, 283(1-2):17-25.

* cited by examiner

A

B

MODIFIED HIV-1 ENVELOPE PROTEINS

CROSS-REFERENCE TO RELATED APPLICATIONS

The present application is a U.S. National Phase Application of International Application PCT/US2005/030563 (filed Aug. 29, 2005), which claims the benefit of U.S. Provisional Application No. 60/604,802 (filed Aug. 27, 2004) all of which are hereby incorporated by reference in their entirety.

ACKNOWLEDGMENT OF FEDERAL SUPPORT

The present invention arose in part from research funded by federal grant NIH 1RO1 AI37433.

FIELD OF THE INVENTION

The invention related to HIV-1 envelope proteins and their method of use as vaccines for the prevention and treatment of AIDS.

BACKGROUND OF THE INVENTION

Efforts to develop a vaccine to prevent infections with Human Immunodeficiency Virus Type 1 (HIV-1) have been complicated by resistance of the virus to the effects of antibodies. Specifically, efforts to develop vaccines that induce antibodies that neutralize the infectivity of diverse strains of HIV-1 have had limited success. Neutralizing antibodies are likely to be critical for vaccine success, since they are the only immunological mechanism that may completely prevent infection. Neutralizing antibodies are the principal mechanism for effectiveness of most or all proven viral vaccines (Galasso (1997) Antiviral Agents and Diseases of Man, Raven Press, 791-833). Even natural infections with HIV-1 are not associated with robust neutralizing antibody responses. In most patients, infection progresses for a number of years before antibodies develop that neutralize a variety of HIV strains (Quinnan et al. (1999) AIDS Res. Hum. Retroviruses 15, 561-70). Even after such an extended period, it is rare that an individual will develop antibodies that neutralize most strains of HIV-1.

The component of HIV-1 that is the target of neutralizing antibodies is the envelope protein spike. The essential unit comprising the spike is a dimer composed of the 120 kd surface protein (gp120) and the 41 kd transmembrane protein (gp41). The spike is believed to be a trimer of such heterodimers. The gp41 molecules anchor the complex to the viral membrane, and the gp120 molecules are associated with the gp41 molecules in such a way that they mediate the interaction of the virus with receptors on target cells. The epitopes that induce neutralizing antibodies and interact with them are in the gp120 and gp41 molecules. Infection of target cells by HIV-1 is a multi-step process, which begins when the viral gp120 molecules bind to the principal viral receptor on target cells, CD4. Binding to CD4 induces conformational change in the envelope protein spike, such that it is then competent to bind to the viral coreceptor, a chemokine receptor molecule that is usually either CCR5 or CXCR4. It is believed that the binding of the envelope proteins to the coreceptor results in further conformational change that results in the membranes of the virus and target cell being drawn together and undergoing fusion. Once membrane fusion occurs, the viral core may enter the target cell and initiate subsequent steps in the infection process. Neutralizing epitopes in envelope proteins are highly conformation-dependent, and many of them may only be formed during the conformational transitions that occur subsequent to CD4 or coreceptor interaction. Vaccines that are intended to induce antibodies that neutralize HIV-1 are designed using forms of envelope protein that are prepared in ways that may result in presentation to the immune system of epitopes that will induce broadly cross-reactive neutralizing antibodies.

An extraordinary variety of approaches to preparation of HIV-1 envelope protein-based vaccines has been tried for induction of broadly cross-reactive neutralizing antibodies with limited success. The approaches used have included the administration of envelope protein prepared using various recombinant DNA techniques, synthetic peptides representative of particular structures in the envelope protein complex, live viral vectors that express envelope proteins in vivo, covalently linked complexes of envelope proteins and CD4, and other materials. Previous research utilized a unique HIV-1 envelope proteins as immunogen, and two methods of presentation of envelope proteins as vaccine, both of which were designed to present the HIV-1 envelope proteins in a form that closely resembled the conformation it assumes on the surface of the virus (Dong et al. (2003) J. Virol. 77, 3119-3130).

The unique envelope protein that was used in those studies is designated R2 (Quinnan et al. (1999) AIDS Res. Hum. Retroviruses 15, 561-570; Quinnan et al. (1998) AIDS Res. Hum. Retroviruses 14, 939-949; Trkola et al. (1995) J. Virol. 69, 6609-6617; Zhang et al. (2002) J. Virol. 76, 644-655). The gene encoding this envelope protein was recovered from cells from an HIV-1-infected donor, who had antibodies that neutralized many different primary isolates of HIV-1. Primary isolates are notoriously difficult to neutralize, and sera from infected humans generally neutralize few, or a limited subset of strains of HIV-1. The envelope protein gene from the donor was cloned and the envelope protein that it encodes has been characterized extensively. When the envelope protein is expressed on the surface of HIV-1, using a method known as pseudotyping, the virus displays unique characteristics. It is able to infect cells that express the HIV-1 coreceptor, CCR5, in the absence of the primary receptor, CD4. All other naturally occurring strains of HIV-1 require CD4 for infection. Other characteristics of the virus suggest that the envelope protein is in a conformation that most envelope protein do not assume until after binding to CD4. The R2 envelope protein is sensitive to neutralization by monoclonal antibodies (Mabs) that do not neutralize most strains of HIV-1 unless they are first bound to CD4. These Mabs are said to be directed against CD4-induced (CD4i) epitopes. Since these epitopes are required for coreceptor binding, they are highly conserved among strains of HIV-1. A rare mutation in variable region 3 (V3) of the R2 envelope protein is necessary for its CD4-independent infectivity as well as its sensitivity to CD4i Mabs. This mutation has similar, but variable effects on other strains of HIV-1, indicating that its effects depend to a certain extent on other sequences in the R2 envelope protein. The mutation involves a proline substitution near the tip of the V3 loop structure. This proline undoubtedly has significant effects on conformation of the V3 loop, and apparently has significant effects on the conformation of the entire Env. It is this Env, which is apparently triggered to express cross-reactive CD4i epitopes, which has been used to induce broadly cross-reactive neutralization.

Two methods were used for immunization of mice and monkeys with the R2 envelope protein (Dong et al. (2003) J. Virol. 77, 3119-3130). One of the methods involved use of a viral expression vector for in vivo expression, and the other involved administration a form of the envelope protein that had been engineered to be missing part of the gp41 molecule (Broder et al. (1994) Proc. Natl. Acad. Sci. USA 91, 11699-11703; Earl et al. (1994) J. Virol. 68, 3015-3026). This protein is referred to as gp140, and is similar to the intact protein spike, but is produced by cells engineered to express the protein as a soluble trimeric molecule. The gp140 protein retains its conformation in potent adjuvant. The two immunization methods have been used separately and sequentially.

Immunization of mice and monkeys with R2 Env induced neutralizing antibodies with cross-reactivity patterns similar to each other and to the cross-reactivity of the serum from the donor of the R2 envelope protein. The serum from the donor of R2 neutralizes strains of all HIV-1 subtypes that have been tested, but neutralizes strains of the A, B, C, and F subtypes much better than the D and E subtypes. The sera from the immunized mice and monkeys neutralize HIV-1 strains of the A, B, C, and F subtypes, but not of the D or E subtypes. It is speculated that this pattern of cross-reactivity reflects the cross-reactivity of the CD4i neutralization epitopes expressed on R2 envelope protein. It is noteworthy that the responses induced in monkeys neutralized one of three strains tested of recombinant Simian-Human Immunodeficiency virus (SHIV); the two strains that were not neutralized are sensitive to neutralization by a Mab directed against a cross-reactive epitope in gp41, 2F5. An implication of this finding is that the R2 envelope protein may not be an effective inducer of antibodies that recognize the 2F5 epitope. Since 2F5 is a human Mab, envelope protein from other donors with cross-reactive neutralizing antibodies may express epitopes that would be better inducers than R2 of antibodies that recognize the 2F5 epitope.

The 2F5 Mab is of particular interest, since it is one of the three most highly cross-reactive neutralizing human Mabs that have been discovered (Trkola et al. (1995) J. Virol. 69, 6609-6617). Its importance is documented in studies, which demonstrated that combinations of 2F5 and the other two highly cross-reactive Mabs could protect monkeys from infection with SHIV (Mascola et al. (1999) J. Virol. 73, 4009-4018; Mascola et al. (2000) Nat. Med. 6, 207-210). The core epitope recognized by 2F5 has been localized by epitope mapping studies to a region of the gp41 ectodomain near the viral membrane. The amino acid sequence of the core epitope is the sequence ELDKWAS (SEQ ID NO: 1). However, there have been no reports of successful induction of neutralizing antibodies using as immunogens synthetic peptides comprising either this sequence or this sequence plus additional flanking sequences. It is likely, therefore, that the capacity of HIV-1 Envelope protein to induce neutralizing antibodies directed against the 2F5 epitope depends upon additional, not yet identified sequences, or is dependent upon conformation of this region of the molecule. It is thought that this region of gp41 undergoes conformational changes during the process of viral attachment to target cells and fusion of the virus and cell membranes. It is reasonably possible that the actual 2F5 neutralization epitope of most strains of HIV-1 does not actually form until fusion-related conformational changes have occurred. HIV-1 Envelope protein which expressed the epitope in its neutralization-active form in the absence of target cell interaction would be particularly good candidates for use in vaccination regimens for induction of 2F5-like antibodies.

Previously, Applicants have demonstrated the isolation of a unique HIV-1 envelope protein gene from an individual with BCN antibodies (see, for example, WO 00/07631). The Envelope protein encoded by this gene was designated R2, and is unique with respect to its amino acid sequence and its ability to infect target cells in the absence of CD4. The R2 Envelope protein is unusual with respect to its sensitivity to neutralization by Mabs against epitopes that are usually neutralization sensitive only in the presence of CD4. The CD4-independence and sensitivity of the R2 Envelope protein to neutralization by these Mabs are both dependent upon an unusual sequence in V3 of the protein. The R2 Envelope protein has been used to immunized mice and monkeys, and induced BCN antibodies in each species. Envelope proteins that induce antibodies against neutralization epitopes distinct from those targeted by R2 could be important components of an immunogen that approached universal effectiveness in prevention of HIV-1 infection.

SUMMARY OF THE INVENTION

The invention encompasses a modified HIV-1 envelope protein or fragment thereof comprising at least one epitope which induces a broadly cross reactive antibody response following administration to a mammal, including humans, wherein the envelope protein comprises an amino acid substitution at a residue corresponding to position 657 of SEQ ID NO: 3 or 659 of SEQ ID NO: 2. In one embodiment the substitution at position 657 is a threonine for alanine while in another embodiment, the substitution at position 659 is a threonine for lysine. In other embodiments of the invention, the modified HIV-1 envelope protein or fragment thereof comprises, or consists of, the amino acid sequence of SEQ ID NO: 2, 3, 4, 5, 6, 7, 43, 45, 47 or 49.

In another embodiment, the modified HIV-1 envelope protein or fragment thereof comprises at least one neutralizing antibody epitope comprising the amino acid sequence SEQ ID NO: 55. In some embodiments, the amino acid sequence of the epitope comprises SEQ ID NO: 20 or 25.

The invention also encompasses a nucleic acid encoding any of the aforementioned modified HIV-1 envelope proteins or fragments thereof. In some embodiments, the nucleic acid molecule comprises, or consists of, the nucleotide sequence of SEQ ID NO: 42, 44, 46, 48, 50, 51, 52, 53 or 54. In additional embodiments, the nucleic acid molecule is operably linked to one or more expression control elements. The invention also encompasses a nucleic acid vector comprising any of the aforementioned nucleic acids. The invention further encompasses a host cell transfected or transformed to contain these nucleic acid molecules or vectors. The host cell may be a eukaryotic or prokaryotic host cell. The invention includes a method for producing a polypeptide comprising culturing this host cell under conditions in which the polypeptide encoded by said nucleic acid molecule is expressed.

The invention includes a composition comprising the modified HIV-1 envelope protein or fragment thereof, or nucleic acids encoding these polypeptides, as described above and a pharmaceutically acceptable carrier. In one embodiment, the composition is suitable as a vaccine in humans.

The invention includes a fusion protein comprising the aforementioned modified HIV-1 envelope protein or fragment thereof. The invention also includes a method of generating antibodies in a mammal comprising administering one or more of the aforementioned modified HIV-1 envelope proteins or fragments thereof in an amount sufficient to induce the production of the antibodies. The invention further includes a method of generating antibodies in a mammal comprising administering at least one nucleic acid encoding any of the aforementioned modified HIV-1 envelope protein or fragment thereof in an amount sufficient to express levels of the HIV-1 envelope protein or fragment thereof to induce the production of the antibodies. The invention includes antibodies produced by any of these methods. In one embodiment, the antibody is monoclonal while in other embodiments, the antibodies are broadly cross-reactive HIV-1 envelope neutralizing antibodies. In certain embodiments, the antibodies inhibit HIV infection and/or are effective for reducing the amount of HIV present in an infected individual.

DETAILED DESCRIPTION

Figure 1:
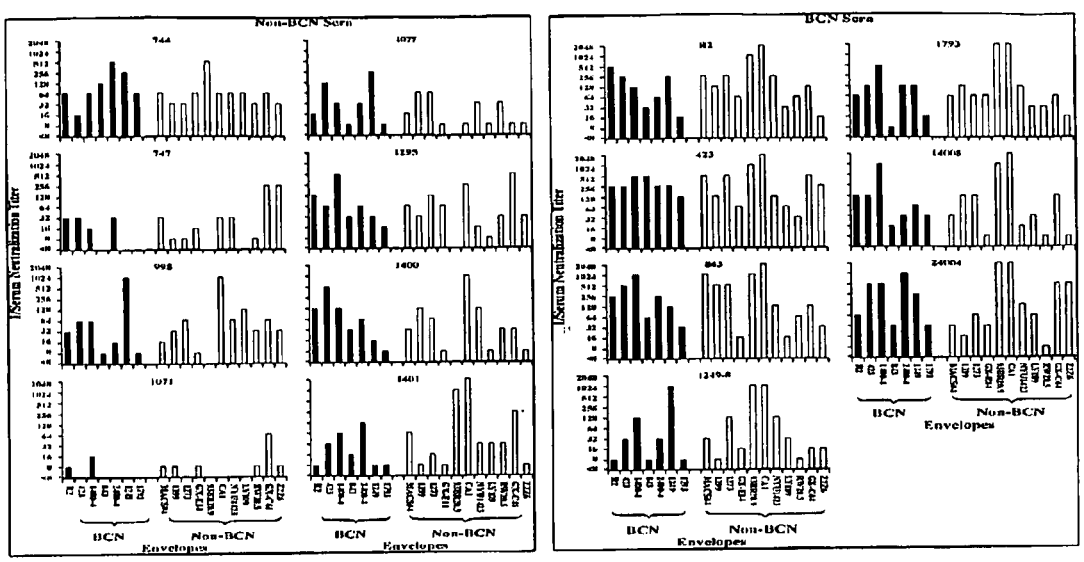
FIG. 1: Neutralization of pseudotyped HIV-1 strains by sera from donors with and without broadly cross-neutralizing (BCN) antibodies.

A group of donors with HIV-1 infections have been identified who have broadly cross-reactive neutralizing antibodies. The sera from donors were screened for neutralization of distantly related primary isolates of HIV-1 to identify those that were considered broadly cross-neutralizing (BCN). These envelope proteins and the genes encoding them are the subject of this invention.

HIV-1 Envelope Proteins

The invention encompasses isolated or modified HIV-1 envelope proteins that express epitopes which bind broadly cross-reactive neutralizing antibodies. Normally, such epitopes are only transiently expressed during fusion of the envelope protein to a cell-surface receptor (e.g., CD4, CCR5, CXCR4, etc.) due to binding and subsequent conformational change of the envelope protein to reveal the epitope. Thus, when an envelope protein is not bound to a cell surface receptor, such epitopes are generally not expressed on the surface of the envelope protein and hence not available for binding to (or for interacting with) broadly cross-reactive anti-envelope protein antibodies. The isolated HIV-1 envelope proteins of the present invention express these epitopes on their surface in the absence of binding to a cell surface receptor. The expression of these epitopes is responsible for induction of the BCN response.

The invention therefore includes an HIV-1 envelope protein or fragment thereof comprising an epitope which is capable of inducing the production of, and binding to, a broadly cross reactive neutralizing antibody. In one embodiment, the epitope encompasses a component of the three dimensional structure of an HIV-1 envelope protein that is displayed regardless of whether or not the HIV-1 envelope protein is binding to a cell surface receptor. In one embodiment, these epitopes are linear amino acid sequences from a modified HIV-1 envelope protein. These epitopes contain amino acid sequences that correspond to amino acid sequences in epitopes that in most HIV envelope proteins are only transiently expressed during binding to a cell surface receptor. Nonetheless, the three dimensional structures are displayed on the protein surface in the absence of the envelope protein binding to a cell surface receptor. HIV-1 envelope proteins containing these epitopes are associated with a broadly cross-reactive neutralizing antibody response in humans. Examples of polypeptides which contain the expressed epitope include, but are not limited to, SEQ ID NO: 2 (1400/4), 3 (2400/4) or 55.

HIV-1 envelope proteins containing modifications in the primary amino acid sequence, which result in envelope proteins with epitopes which induce a broadly cross-reactive neutralizing antiserum, are also encompassed in the invention. Such substitutions confer induction of a broadly cross-reactive neutralizing antibody response both in vivo and in vitro. Such alterations include, but are not limited to, an amino acid substitution at a position corresponding to amino acid residue 659 of SEQ ID NO: 2 (1400/4) and residue 657 of SEQ ID NO: 3 (2400/4). Amino acid residues at these and other positions can be systematically modified, either singly or in combination with other sites so as to enhance immunogenicity. The R2 envelope protein (SEQ ID NO: 41) has an exceptional capacity to induce neutralizing antibodies that are active against highly divergent strains of HIV-1, and this immunogenicity corresponds to the presence of a proline-methionine sequence at residues 313 and 314. Substitution of amino acid residues 313 and 314 with the consensus sequence at those positions, histidine-isoleucine, abrogates the constitutive expression of epitopes that ordinarily requires interaction of HIV-1 envelopes with their primary receptor, CD4, for expression. Notwithstanding such modification(s), the conformation of HIV-1 envelope proteins remains sufficiently intact to maintain infectivity when present as a component of the virion. Individuals (i.e., humans) who are infected with HIV-1 strains that possess envelope proteins with such active epitopes may develop immune responses which reduce or block viral infectivity of multiple subtypes of HIV-1.

The envelope proteins of the invention include the full length envelope protein wherein one or more epitope sites have been modified, and fragments thereof containing one or more of the modified epitope sites. In one embodiment, one or more amino acid residues are deleted while in another embodiment, one or more of these sites are substituted with another amino acid which alters the conformation of the epitope. Examples of amino acids which can be substituted include, but are not limited to, any naturally occurring amino acid. Preferred naturally occurring amino acids which can be substituted include, but are not limited to, threonine, lysine, and proline. Modified amino acids can also be substituted at any epitope site.

The relative positions of known epitope sites of the HIV-1 envelope protein can be determined by amino acid sequence alignment of multiple HIV-1 envelope protein sequences. Amino acid and nucleotide sequence information for envelope proteins of other strains are referenced in Kuiken et al. (2002) HIV Sequence Compendium, Los Alamos National Laboratory, LA-UR03-3564, which is hereby incorporated by reference. Exemplary epitope sites include the binding epitope for the 2F5 and 4E10 monoclonal antibodies (Muster et al. (1994) J. Virol. 68, 4031-4034; Muster et al. (1993) J. Virol. 67, 6642-6647. The 2F5 epitope amino acid sequence (ELDKWAS (SEQ ID NO: 1)) corresponds to residues 654 to 660 of SEQ ID NO: 4 and residues 657 to 663 of SEQ ID NO: 6 while the 4E10 epitope (NWFDIT (SEQ ID NO: 8)) corresponds to residues 663 to 668 of SEQ ID NO: 4 and residues 666 to 671 of SEQ ID NO: 6. Corresponding residues which also comprise the 2F5 and 4E10 monoclonal antibody epitopes in envelope proteins from other HIV-1 isolates which may not have the same amino acid residue number can readily be determined by amino acid sequence alignment as set forth herein.

In another embodiment, the invention encompasses HIV-1 envelope proteins comprising the amino acid sequence as set forth in SEQ ID NO: 2, 3, 4, 5, 6, 7, 43, 45, 47 or 49 and fragments thereof containing one or more of the modified epitope sites including the modification at an amino acid corresponding to residue 662. In yet another embodiment, the invention encompasses HIV-1 envelope proteins consisting of the amino acid sequence as set forth in SEQ ID NO: 22, 3, 4, 5, 6, 7, 43, 45, 47 or 49.

Nucleic Acid Molecules

The present invention further provides nucleic acid molecules that encode the isolated or modified HIV-1 envelope proteins or fragments thereof that contain one or more of the modified epitopes, preferably in isolated form. As used herein, "nucleic acid" is defined as RNA or DNA that encodes a protein or peptide as defined above, is complementary to a nucleic acid sequence encoding such peptides, hybridizes to nucleic acid molecules that encode the isolated or modified HIV-1 envelope proteins across the open reading frame under appropriate stringency conditions, or encodes a polypeptide that shares at least about 75% sequence identity, preferably at least about 80%, more preferably at least about 85%, and even more preferably at least about 90% or even 95% or more identity with the isolated or modified HIV-1 envelope proteins.

The nucleic acids of the invention further include nucleic acid molecules that share at least 80%, preferably at least about 85%, and more preferably at least about 90% or 95% or more identity with the nucleotide sequence of nucleic acid molecules that encode the isolated or modified HIV-1 envelope proteins, particularly across the open reading frame. Specifically contemplated are genomic DNA, cDNA, mRNA and antisense molecules, as well as nucleic acids based on alternative backbones or including alternative bases whether derived from natural sources or synthesized. Such nucleic acids, however, are defined further as being novel and unobvious over any prior art nucleic acid including that which encodes, hybridizes under appropriate stringency conditions, or is complementary to nucleic acid encoding a protein according to the present invention.

Homology or identity at the nucleotide or amino acid sequence level is determined by BLAST (Basic Local Alignment Search Tool) analysis using the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (1994) Nature Genetics 6, 119-129 which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al. (1992) Proc. Natl. Acad. Sci. USA 89, 10915-10919, fully incorporated by reference), recommended for query sequences over 85 in length (nucleotide bases or amino acids).

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C. to 68° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer (pH 6.5) with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS or 68° C. in 0.1×SSC and 0.5% SDS. A skilled artisan can readily determine and vary the stringency conditions appropriately to obtain a clear and detectable hybridization signal. Preferred molecules are those that hybridize under the above conditions to the complement of nucleic acid sequences encoding the proteins comprising SEQ ID NO: 2, 3, 4, 5, 6 and 7 and which encode a functional protein. Even more preferred hybridizing molecules are those that hybridize under the above conditions to the complement strand of the open reading frame of the nucleic acid encoding the isolated or modified HIV-1 envelope protein. Examples include, but are not limited to, nucleic acids comprising a nucleotide sequence as set forth in SEQ ID NO: 42, 44, 46, 48, 50, 51, 52, 53 or 54 As used herein, a nucleic acid molecule is said to be "isolated" when the nucleic acid molecule is substantially separated from contaminant nucleic acid molecules encoding other polypeptides.

The present invention further provides fragments of the encoding nucleic acid molecule which contain the desired modification (i.e., modification of one or more amino acids in the selected epitope) in the envelope proteins. As used herein, a fragment of an encoding nucleic acid molecule refers to a small portion of the entire protein coding sequence. The size of the fragment will be determined by the intended use. For example, if the fragment is chosen so as to encode an active portion of the protein (i.e., a selected monoclonal antibody epitope or modification of such an epitope as described herein), the fragment will need to be large enough to encode the functional regions of the protein (i.e., epitopes). For instance, fragments which encode peptides corresponding to predicted antigenic regions may be prepared. If the fragment is to be used as a nucleic acid probe or PCR primer, then the fragment length is chosen so as to obtain a relatively small number of false positives during probing/priming.

Fragments of the encoding nucleic acid molecules of the present invention (i.e., synthetic oligonucleotides) that are used to synthesize gene sequences encoding proteins of the invention, can easily be synthesized by chemical techniques, for example, the phosphotriester method of Matteucci et al. (1981) J. Am. Chem. Soc. 103, 3185-3191 or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention. Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

Recombinant Nucleic Acids

The present invention further provides recombinant DNA molecules (rDNA) that contain a coding sequence. As used herein, a rDNA molecule is a DNA molecule that has been subjected to molecular manipulation in situ. Methods for generating rDNA molecules are well known in the art, for example, see Sambrook et al. (2001) Molecular Cloning—A Laboratory Manual, Cold Spring Harbor Laboratory Press. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 (BioRad), pPL and pKK223 (Pharmacia).

Expression vectors compatible with eukaryotic cells, preferably those compatible with vertebrate cells, can also be used to form rDNA molecules that contain a coding sequence. Eukaryotic cell expression vectors, including viral vectors, are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies Inc.), pTDT1 (ATCC), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al. (1982) J. Mol. Anal. Genet. 1, 327-341). Alternatively, the selectable marker can be present on a separate plasmid, and the two vectors are introduced by co-transfection of the host cell, and selected by culturing in the appropriate drug for the selectable marker. The present invention further provides host cells transformed with a nucleic acid molecule that encodes a protein of the present invention. The host cell can be either prokaryotic or eukaryotic.

Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH-3T3) available from the ATCC as CRL 1658, baby hamster kidney cells (BHK), and the like eukaryotic tissue culture cell lines. Any prokaryotic host can be used to express a rDNA molecule encoding a protein of the invention. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al. (1972) Proc. Natl. Acad. Sci. USA 69, 2110; and Sambrook et al. (2001) Molecular Cloning—A Laboratory Manual, Cold Spring Harbor Laboratory Press. With regard to transformation of vertebrate cells with vectors containing rDNA, electroporation, cationic lipid or salt treatment methods are typically employed, see, for example, Graham et al. (1973) Virol. 52, 456; Wigler et al. (1979) Proc. Natl. Acad. Sci. USA 76, 1373-1376.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern (1975) J. Mol. Biol. 98, 503-504 or Berent et al. (1985) Biotech. 3, 208-209 or the proteins produced from the cell assayed via an immunological method.

Production of Recombinant Proteins

One skilled in the art would know how to make recombinant nucleic acid molecules which encode the isolated or modified HIV-1 envelope proteins of the invention. Furthermore, one skilled in the art would know how to use these recombinant nucleic acid molecules to obtain the proteins encoded thereby, as described herein for the recombinant nucleic acid molecule which encodes an isolated or modified HIV-1 envelope protein comprising one or more modifications at one or more epitopes sites. In one embodiment, the recombinant envelope protein or fragment thereof contains a substitution of an amino acid residue (e.g., threonine for alanine) at a position corresponding to residue 659 of SEQ ID NO: 2.

In accordance with the invention, numerous vector systems for expression of the isolated or modified HIV-1 envelope protein may be employed. For example, one class of vectors utilizes DNA elements which are derived from animal viruses, such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The marker may provide, for example, prototrophy to an auxotrophic host, biocide resistance, (e.g., antibiotics) or resistance to heavy metals such as copper or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals. The cDNA expression vectors incorporating such elements include those described by Okayama (1983) Mol. Cell. Biol. 3, 280-289.

The vectors used in the subject invention are designed to express high levels of HIV-1 envelope proteins in cultured eukaryotic cells as well as efficiently secrete these proteins into the culture medium. In one embodiment, the targeting of the HIV-1 envelope proteins into the culture medium is accomplished by fusing in-frame to the mature N-terminus of the HIV-1 envelope protein the tissue plasminogen activator (tPA) prepro-signal sequence.

The HIV-1 envelope protein may be produced by (a) transfecting a mammalian cell with an expression vector encoding the HIV-1 envelope protein; (b) culturing the resulting transfected mammalian cell under conditions such that HIV-1 envelope protein is produced; and (c) recovering the HIV-1 envelope protein from the cell culture media or the cells themselves.

Once the expression vector or DNA sequence containing the constructs has been prepared for expression, the expression vectors may be transfected or introduced into an appropriate mammalian cell host. Various techniques may be employed to achieve this, such as, for example, protoplast fusion, calcium phosphate precipitation, electroporation or other conventional techniques. In the case of protoplast fusion, the cells are grown in media and screened for the appropriate activity.

Methods and conditions for culturing the resulting transfected cells and for recovering the HIV-1 envelope protein so produced are well known to those skilled in the art, and may be varied or optimized depending upon the specific expression vector and mammalian host cell employed.

In accordance with the claimed invention, the preferred host cells for expressing the HIV-1 envelope protein of this invention are mammalian cell lines. Mammalian cell lines include, for example, monkey kidney CV1 line transformed by SV40 (COS-7); human embryonic kidney line 293 (HEK293); baby hamster kidney cells (BHK); Chinese hamster ovary-cells-DHFR (CHO); Chinese hamster ovary-cells DHFR(DXB11); monkey kidney cells (CV1); African green monkey kidney cells (VERO-76); human cervical carcinoma cells (HELA); canine kidney cells (MDCK); human lung cells (W138); human liver cells (HepG2); mouse mammary tumor (MMT 060562); mouse cell line (C127); and myeloma cell lines.

Other eukaryotic expression systems utilizing non-mammalian vector/cell line combinations can be used to produce the envelope proteins. These include, but are not limited to, baculovirus vector/insect cell expression systems and yeast shuttle vector/yeast cell expression systems.

Methods and conditions for purifying HIV-1 envelope proteins from the culture media are provided in the invention, but it should be recognized that these procedures can be varied or optimized as is well known to those skilled in the art.

The HIV-1 envelope proteins or fragments thereof of the present invention may also be prepared by any known synthetic techniques. Conveniently, the proteins may be prepared using the solid-phase synthetic technique initially described by Merrifield (1965), which is incorporated herein by reference. Other peptide synthesis techniques may be found, for example, in Bodanszky et al. (1976), Peptide Synthesis, Wiley.

HIV-1 Envelope Fusion Proteins

HIV-1 envelope fusion proteins and methods for making such proteins have been previously described (U.S. Pat. No. 5,885,580). It is now a relatively straight forward technology to prepare cells expressing a foreign gene. Such cells act as hosts and may include, for the fusion proteins of the present invention, yeasts, fungi, insect cells, plants cells or animals cells. Expression vectors for many of these host cells have been isolated and characterized, and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extrachromosomal plasmids or after integration in whole or in part in the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector, and other factors readily appreciated by those of ordinary skill in the art.

The foreign DNA insert of interest comprises any DNA sequence coding for fusion proteins including any synthetic sequence with this coding capacity or any such cloned sequence or combination thereof. For example, fusion proteins coded and expressed by an entirely recombinant DNA sequence is encompassed by this invention but not to the exclusion of fusion proteins peptides obtained by other techniques.

Vectors useful for constructing eukaryotic expression systems for the production of fusion proteins comprise the fusion protein's DNA sequence, operatively linked thereto with appropriate transcriptional activation DNA sequences, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

Yeast expression systems, which are the preferred variety of recombinant eukaryotic expression system, generally employ *Saccharomyces cerevisiae* as the species of choice for expressing recombinant proteins. Other species of the genus *Saccharomyces* are suitable for recombinant yeast expression system, and include but are not limited to *carlsbergensis, uvarum, rouxii, montanus, kluyveri, elongisporus, norbensis, oviformis,* and *diastaticus. Saccharomyces cerevisiae* and similar yeasts possess well known promoters useful in the construction of expression systems active in yeast, including but not limited to GAP, GAL10, ADH2, PHO5, and alpha mating factor.

Yeast vectors useful for constructing recombinant yeast expression systems for expressing fusion proteins include, but are not limited to, shuttle vectors, cosmid plasmids, chimeric plasmids, and those having sequences derived from two micron circle plasmids. Insertion of the appropriate DNA sequence coding for fusion proteins into these vectors will, in principle, result in a useful recombinant yeast expression system for fusion proteins where the modified vector is inserted into the appropriate host cell, by transformation or other means. Recombinant mammalian expression system are another means of producing the fusion proteins for the vaccines/immunogens of this invention. In general, a host mammalian cell can be any cell that has been efficiently cloned in cell culture. However, it is apparent to those skilled in the art that mammalian expression options can be extended to include organ culture and transgenic animals. Host mammalian cells useful for the purpose of constructing a recombinant mammalian expression system include, but are not limited to, Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover (1985), DNA Cloning: A Practical Approach, IRL Press.

Fusion proteins may possess additional and desirable structural modifications not shared with the same organically synthesized peptide, such as adenylation, carboxylation, N- and O-glycosylation, hydroxylation, methylation, phosphorylation or myristylation. These added features may be chosen or preferred as the case may be, by the appropriate choice of recombinant expression system. On the other hand, fusion proteins may have its sequence extended by the principles and practice of organic synthesis.

Vaccine Compositions

When used in vaccine or immunogenic compositions, the isolated or modified HIV-1 envelope proteins or fragments thereof of the present invention may be used as "subunit" vaccines or immunogens. Such vaccines or immunogens offer significant advantages over traditional vaccines in terms of safety and cost of production; however, subunit vaccines are often less immunogenic than whole-virus vaccines, and it is possible that adjuvants with significant immunostimulatory capabilities may be required in order to reach their full potential.

Currently, adjuvants approved for human use in the United States include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), Muramyl dipeptide (MDP), synthetic analogues of MDP, N-acetylmuramyl-L-alanyl-D-isoglutamyl-L-alanine-2-[1,2-dipalmitoyl-s-glycero-3-(hydroxyphosphoryloxy)]ethylamide (MTP-PE) and compositions containing a degradable oil and an emulsifying agent, wherein the oil and emulsifying agent are present in the form of an oil-in-water emulsion having oil droplets substantially all of which are less than one micron in diameter.

The formulation of a vaccine or immunogenic compositions of the invention will employ an effective amount of the protein or peptide antigen. That is, there will be included an amount of antigen which, in combination with the adjuvant, will cause the subject to produce a specific and sufficient immunological response so as to impart protection to the subject from subsequent exposure to HIV. When used as an immunogenic composition, the formulation will contain an amount of antigen which, in combination with the adjuvant, will cause the subject to produce specific antibodies which may be used for diagnostic or therapeutic purposes.

The vaccine compositions of the invention may be useful for the prevention or therapy of HIV-1 infection. While all animals that can be afflicted with HIV-1 can be treated in this manner, the invention, of course, is particularly directed to the preventive and therapeutic use of the vaccines of the invention in humans. Often, more than one administration may be required to bring about the desired prophylactic or therapeutic effect; the exact protocol (dosage and frequency) can be established by standard clinical procedures.

The vaccine compositions are administered in any conventional manner which will introduce the vaccine into the animal, usually by injection. For oral administration the vaccine composition can be administered in a form similar to those used for the oral administration of other proteinaceous materials. As discussed above, the precise amounts and formulations for use in either prevention or therapy can vary depending on the circumstances of the inherent purity and activity of the antigen, any additional ingredients or carriers, the method of administration and the like.

By way of non-limiting illustration, the vaccine dosages administered will typically be, with respect to the antigen, a minimum of about 0.1 mg/dose, more typically a minimum of about 1 mg/dose, and often a minimum of about 10 mg/dose. The maximum dosages are typically not as critical. Usually, however, the dosage will be no more than 500 mg/dose, often no more than 250 mg/dose. These dosages can be suspended in any appropriate pharmaceutical vehicle or carrier in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

In an alternative format, vaccine or immunogenic compositions may be prepared as vaccine vectors which express the HIV-1 envelope protein or fragment thereof in the host animal. Any available vaccine vector may be used, including Venezuelan Equine Encephalitis virus (see U.S. Pat. No. 5,643,576), poliovirus (see U.S. Pat. No. 5,639,649), pox virus (see U.S. Pat. No. 5,770,211) and vaccina virus (see U.S. Pat. Nos. 4,603,112 and 5,762,938). Alternatively, naked nucleic acid encoding the protein or fragment thereof may be administered directly to effect expression of the antigen (see U.S. Pat. No. 5,739,118).

The HIV-1 envelope proteins or fragments thereof may be used as immunogens in various combinations. For example, an envelope protein that is expected to induce antibodies against one or more epitopes in gp41, such as 14/00/4, may be used in combination with an envelope glycoprotein that is expected to induce antibodies against epitopes in gp120, such as R2. Additional envelope glycoproteins may be combined in the immunization regimen, particularly envelopes that induce antibodies against additional epitopes or that represent variant forms of the same epitopes expressed by different subtypes of HIV-1. Different segments of these envelope glycoproteins may be used, such as gp120 from one strain of HIV-1 and gp41 from other strains of HIV-1.

Antibodies and Methods of Use

This invention further provides a human monoclonal antibody directed to an expressed epitope on the isolated or modified HIV-1 envelope proteins of the invention and capable of blocking the binding of multiple subtypes of HIV-1 to human cells and capable preventing infection of human cells by HIV-1 both in vitro and/or in vivo. In one embodiment, these antibodies to a known epitope which has been modified by one or more substitutions or deletions of amino acids in the epitope. Examples of known antibody epitopes include, but are not limited to, the 2F5 and 4E10 monoclonal antibody epitopes. Amino acid substitutions in the 2F5 epitope include, but are not limited to, threonine for alanine at a position corresponding to residue 659 of SEQ ID NO: 2.

The monoclonal antibodies of the invention may be labeled with a detectable marker. Detectable markers useful in the practice of this invention are well known to those of ordinary skill in the art and may be, but are not limited to radioisotopes, dyes or enzymes such as peroxidase or alkaline phosphatase. In addition, the monoclonal antibodies of the invention may be conjugated with a cytotoxic agent.

This invention also concerns an anti-idiotypic antibody directed against the human monoclonal antibodies which bind to the envelope proteins of the invention. This anti-idiotypic antibody may also be labeled with a detectable marker. Suitable detectable markers are well known to those of ordinary skill in the art and may be, but are not limited to radioisotopes, dyes or enzymes such as peroxidase or alkaline phosphatase.

The anti-idiotypic antibody is produced when an animal is injected with a monoclonal antibody which binds to the HIV-1 envelope proteins of the invention. The animal will then produce antibodies directed against the idiotypic determinants of the injected antibody (Wasserman et al. (1982) Proc. Natl. Acad. Sci. 79, 4810-4814).

Alternatively, the anti-idiotypic antibody is produced by contacting lymphoid cells of an animal with an effective-antibody raising amount of the antigen (i.e., the monoclonal antibody which binds to the envelope proteins of the invention); collecting the resulting lymphoid cells; fusing the collected lymphoid cells with myeloma cells to produce a series of hybridoma cells, each of which produces a monoclonal antibody; screening the series of hybridoma cells to identify those which secrete a monoclonal antibody capable of binding; culturing the resulting hybridoma cell so identified and separately recovering the anti-idiotypic antibody produced by this cell (Cleveland et al. (1983) Nature 305, 56-57). Animals which may be used for the production of anti-idiotypic antibodies in either of the two above-identified methods include, but are not limited to humans, primates, mice, rats, or rabbits. Another aspect of the present invention provides a monoclonal antibody-producing hybridoma produced by this fusion of a human-mouse myeloma analog and a human antibody-producing cell. In the preferred embodiments, the antibody-producing cell is a human peripheral blood mononuclear cell (PBM), a mitogen stimulated PBM such as a Pokeweed Mitogen (PWM) or a phytohemagglutinin stimulated normal PBM (PHAS) or an Epstein-Barr Virus (EBV) transformed B cell. The human-mouse myeloma analog described above has-an average fusion efficiency for growth of antibody-secreting hybridomas of greater than 1 out of 25,000 fused cells when fused with human PBM, mitogen stimulated PBM and EBV transformed B cells. Especially useful antibody-producing hybridomas of the present invention are those hybridomas which produce monoclonal antibodies specific for the HIV-1 envelope proteins of the invention.

The invention also concerns a method for producing a monoclonal antibody-producing hybridoma which comprises fusing the human-mouse analog with an antibody-producing cell, especially those antibody-producing cells listed hereinabove, and the monoclonal antibody which said hybridoma produces.

The invention further concerns a method of blocking binding of HIV-1 to human cells (both in vitro and in vivo) and a method of preventing infection of human cells by HIV-1 which comprises contacting HIV-1 with an amount of the human monoclonal antibody directed to a modified epitope in the envelope proteins of the invention, effective to block binding of HIV-1 to human cells and preventing infection of human cells by HIV-1. In one embodiment, the modified epitope is the 2F5 monoclonal antibody epitope while in another embodiment the 4E10 monoclonal antibody epitope as described herein.

Diagnostic Reagents

The HIV-1 envelope proteins of the present invention may be used as diagnostic reagents in immunoassays to detect anti-HIV-1 antibodies, particularly anti-envelope protein antibodies. Many HIV-1 immunoassay formats are available. Thus, the following discussion is only illustrative, not inclusive. See generally, however, U.S. Pat. No. 4,753,873 and EP 0161150 and EP 0216191.

Immunoassay protocols may be based, for example, upon composition, direct reaction, or sandwich-type assays. Protocols may also, for example, be heterogeneous and use solid supports, or may be homogeneous and involve immune reactions in solution. Most assays involved the use of labeled antibody or polypeptide. The labels may be, for example, fluorescent, chemiluminescent, radioactive, or dye molecules. Assays which amplify the signals from the probe are also known, examples of such assays are those which utilize biotin and avidin, and enzyme-labeled and mediated immunoassays, such as ELISA assays.

Typically, an immunoassay for anti-HIV-1 antibody will involve selecting and preparing the test sample, such as a biological sample, and then incubating it with an HIV-1 envelope protein of the present invention under conditions that allow antigen-antibody complexes to form. Such conditions are well known in the art. In a heterogeneous format, the protein or peptide is bound to a solid support to facilitate separation of the sample from the polypeptide after incubation. Examples of solid supports that can be used are nitrocellulose, in membrane or microtiter well form, polyvinylchloride, in sheets or microtiter wells, polystyrene latex, in beads or microtiter plates, polyvinylidine fluoride, diazotized paper, nylon membranes, activated beads, and Protein A beads. Most preferably, Dynatech, Immulon® microtiter plates or 0.25 inch polystyrene beads are used in the heterogeneous format. The solid support is typically washed after separating it from the test sample.

In homogeneous format, on the other hand, the test sample is incubated with the envelope protein in solution, under conditions that will precipitate any antigen-antibody complexes that are formed, as is known in the art. The precipitated complexes are then separated from the test sample, for example, by centrifugation. The complexes formed comprising anti-HIV antibody are then detected by any number of techniques. Depending on the format, the complexes can be detected with labeled anti-xenogeneic immunoglobulin or, if a competitive format is used, by measuring the amount of bound, labeled competing antibody. These and other formats are well known in the art.

Diagnostic probes useful in such assays of the invention include antibodies to the HIV-1 envelope protein. The antibodies to may be either monoclonal or polyclonal, produced using standard techniques well known in the art (See Harlow & Lane (1988), Antibodies: A Laboratory Manual, Cold Spring Harbor Laboratory Press. They can be used to detect HIV-1 envelope protein by specifically binding to the protein and subsequent detection of the antibody-protein complex by ELISA, Western blot or the like. The isolated or modified HIV-1 envelope protein used to elicit these antibodies can be any of the variants discussed above. Antibodies are also produced from peptide sequences of HIV-1 envelope proteins using standard techniques in the art (Harlow & Lane, supra). Fragments of the monoclonals or the polyclonal antisera which contain the immunologically significant portion can also be prepared.

EXAMPLES

The following working examples specifically point out preferred embodiments of the present invention, and are not to be construed as limiting in any way the remainder of the disclosure. Other generic configurations will be apparent to one skilled in the art. All references, including U.S. or foreign patents, referred to in this application are herein incorporated by reference in their entirety.

Example 1

Materials and Methods

HIV-1 BCN Donors

HIV-1 group M infected donors whose sera were demonstrated to possess potent broad cross neutralizing antibody (BCN) responses (Beirnaert et al. (2000) J. Med. Virol. 62, 14-24) are part of the clinical cohort of the AIDS Reference Center at the Institute of Tropical Medicine (ITM) in Antwerp, Belgium. Peripheral blood mononuclear cells (PBMC) were collected and stored from 6 anti-retroviral (ARV) naïve HIV-1 BCN Donors. The virus envelope subtype, geographic origin and date of sample collection are represented in table 1. For comparison, the previously cloned and characterized R2 envelope (Quinnan et al. (1999) AIDS Res. Hum Retroviruses 15, 561-570; Zhang et al. (2002) J. Virol. 76, 644-655) was included in this study.

HIV-1 Non-BCN Donors

DNA extracts from co-cultured PBMCs of 4 HIV-1 non-BCN donors (NYU1423, CA1, LY109 and 93BR029) were obtained from the Veterans Administration Medical Center. Archived PBMCs from donors VI1399 and VI1273 were obtained from the ITM. Cloning of donor MACS#4, GXC-44 GXE-14 and Z2Z6 has been previously described (Quinnan et al. (1998) AIDS Res. Hum. Retroviruses 14, 939-949; Zhang et al. (1999) J. Virol. 73, 5225-5230). The primary subtype A isolate 93RW20.5 (Gao et al. (1998) J. Virol. 72, 5680-5698) was obtained from the NIH ARRRP. The virus envelope subtype and geographic origin of new donor samples used in this study are represented in table 1.

PCR Amplification and Cloning

Envelope genes were amplified by a nested PCR using the high fidelity rTth DNA polymerase and the cycling parameters as recommended by manufacturers (Applied Biosystems). As template, DNA extracted from uncultured PBMC of all donors except for VI1249, VI843, VI1793, CA1, 93Br029, NYU1423, LY109 in which template DNA for PCR was extracted from co cultured PBMCs. The pSV111$_{93RW20.5}$ was used as a template in the PCR to sub-clone this isolate in pSV7d. Primers used for the first round PCR were designed including the Rev start codon and were based on consensus subtype B sequence. In some cases for the second round PCR, new primers were redesigned and used for amplification of gp160 regardless of HIV-1 subtype. All primers used in the second round PCR were designed with restriction enzyme sites for cloning into appropriate sites in the pSV7d expression vector. The primers used in the nested PCR are as follows:

```
First round primers
Forward:
                                      (SEQ ID NO: 9)
5'atggagccagtagatcctagactagagccctggaagcatccaggaagt
cagcc-3'

Reverse:
                                     (SEQ ID NO: 10)
5'gtcattggtcttaaaggtacctgaggtctgtctggaaaaccc-3'

Second round primers
Forward:
                                     (SEQ ID NO: 11)
5'aaaaggcttaggcatctcctatggcaggaagaagcgg-3'

Reverse:
                                     (SEQ ID NO: 12)
5'ctcgagatactgctcccacccatctgctgctggc-3'

Forward:
                                     (SEQ ID NO: 13)
5'ataagagaaagagcagaagacagtggcaatgagag-3'

Reverse:
                                     (SEQ ID NO: 14)
5'gtcattggtcttaaaggtacctgaggtctgactgg-3'
```

PCR products were visualized on a 0.7% agarose gel and purified with the Qiagen gel extraction kit. Purified envelope and the pSV7d expression vector (Chiron Corporation) were digested with appropriate restriction enzymes. The digested products were purified and ligated with T4 DNA ligase (New England Biolabs). Transformation of DH5α competent *E. Coli* cells with the ligation products was done according to the manufacturers recommendations (Invitrogen). Clones were then screened for insertion of the envelope gene using an "in house" quick miniprep protocol and by gel electrophoresis. Clones screened ranged from 72 to 350 for each primary isolate. Briefly, clones were grown overnight in 2 ml agar broth supplemented with ampicillin (Gibco). After overnight cultures, bacterial cells were lysed and plasmid was analyzed based on size of DNA by gel electrophoresis.

Human Osteosarcoma (HOS) Cells

The Human Osteosarcoma (HOS) cell lines constitutively expressing CD4 and co-receptors for HIV-1 CCR5 or CXCR4 were obtained from the NIH AIDS Research and Reference Reagent Program (ARRRP) (Zhang et al. (2002) J. Virol. 76, 644-55). To test for CD4 independent infection, HOS cells expressing either co-receptor without CD4 were used. HOS cells were maintained in Dulbecco's minimal essential medium (DMEM) (Gibco) supplemented with 10% fetal bovine serum, L-glutamine, and penicillin-streptomycin (Gibco), Tylosin (Sigma) and puromycin for maintenance of plasmid stability.

293T Cells

The human embryonic kidney cell lines (293T) were obtained from the American Type Culture Collection (ATCC). Cells were maintained in Dulbecco's minimal essential medium (Gibco) supplemented with 10%/, fetal bovine serum, L-glutamine and penicillin-streptomycin (Gibco).

Screening and Selection of Functional Envelope Clones

Correct size clones were then screened for function in a 24 well plate co-transfection of 70% to 80%-confluent 293T cells (ATTC) with pNL4-3.luc.E-R-(ARRRP) and pSV7d-env plasmid using the calcium phosphate/HEPES buffer technique, according to manufacturers instruction (Promega). Positive and negative control plasmids were included in each experiment. Eighteen hours after transfection, the media was removed and replaced with media supplemented with 0.1 mM sodium butyrate (Sigma). Cells were allowed to grow for an additional 24 hrs. The supernatant was harvested, centrifuged at 16,000 rpm for five minutes at 4° C. and filtered through a 0.45 μm sterile pore filter (Millipore).

Infectivity Assays

Infectivity assays were carried out in triplicate wells as previously described (Quinnan et al. (1998) AIDS Res. Hum. Retroviruses 14, 939-949). Briefly, 50 μl of two-fold serial dilutions of the filtered pseudovirus supernatant were incubated at 37° C. with 1-2×10$^4$ HOS CD4$^+$ CCR5$^+$ or CXCR4$^+$ cells in 150 μl volume. Infectivity titers were determined on the basis of luminescence measurements at three days post infection of the cells by the pseudotyped viruses. To determine endpoints for infectivity, an individual well was considered positive if the luciferase activity was at least 10-fold greater than that of the negative control. The actual titers of functional clones were then determined by co-transfection of pNL4-3.luc.E-R-(ARRRP) and pSV7d-env plasmid using a 25 cm$^3$ flask followed by an infectivity assay as described above.

Sequencing and BLAST Search of Functional Envelope Clones

After confirmation of infectious clones, gp160 sequencing was done on clones not previously described. Sequencing was initially done on both strands using a total of fourteen forward and reverse primers designed based on consensus subtype B sequences in the Los Alamos National Laboratory HIV sequence database, which is available on the world wide web at www.hiv.lanl.gov. However, new primers were designed as necessary to sequence regions that were not successful with the subtype B consensus primers. Following the sequencing reaction, products were purified using the Performa DTR gel filtration cartridge (Edge BioSystems) to remove excess dNTP and salts. Nucleotide sequencing was performed using the di-deoxy cycle sequencing technique on an Applied Systems Model 3100 Genetic Analyzer. Sequence alignment was performed using the Editseq and Seqman programs in DNA Star (Higgins et al. (1988) Gene 73, 237-244). Confirmation of unique sequence was accessed through the National Center for Biotechnology Information (NCBI) website, which is available on the world wide web at www.ncbi.nlm.nih.gov and the Los Alamos National Laboratory HIV databases, which is available on the world wide web at www.hiv.lanl.gov gov.

Antibodies

Panels of eleven broadly cross-reactive monoclonal antibodies and two-domain soluble CD4 were used in this study (Table 2) and were obtained from various sources and are available through the ARRRP. Polyclonal sera from six BCN donors and eight non-BCN donors were shipped in dry ice from the ITM. The HNS2 serum was obtained from the ARRRP. To inactivate complement sera were incubated at 56° C. for thirty minutes then stored at −20° C. until use.

Neutralization Assays

The envelopes used in the present study were representative of HIV-1 envelope subtypes A, B, C, D, F, CRF01_AE, CRF02_AG, CRF11_cpx, and a B/F recombinant. Neutralization assays were performed as described previously (Zhang et al. (2002) J. Virol. 76, 644-655). Briefly, neutralization assays were carried out in triplicate wells by preincubation of two-fold serial dilutions of human Mabs or polyclonal serum with 25 μl pseudovirus supernatant for one hour at 4° C. followed by infection of 150 μl volume 1-2×10$^4$ HOS CD4$^+$ CCR5$^+$ or CXCR4$^+$ cells in a 96 well tissue culture plate. The plates were incubated at 37° C. in 5% carbon dioxide for three days then washed with phosphate-buffered saline and lysed with 15 μl of 1× Luciferase Assay System cell lysis buffer (Promega) for thirty minutes. Luciferase activity was read using a MicroLumat Plus luminometer. Infectivity or neutralization titers were determined on the basis of luminescence measurements and the endpoint was considered to be the last dilution of sera or human Mab at which the mean results from the test samples were less than 50% of the non-neutralized control mean. The sera or human MAbs concentration that resulted in 90% neutralization was always two to eight (usually four) fold greater than that which produces 50% neutralization. Neutralization assays for each envelope clone against the MAbs were carried out at least in two independent experiments. However due to limitation of serum samples, experiments with sera were only done once for most of the envelope clones and twice if the data was inconclusive.

Example 2

Mutagenesis of A659T

To study the effects of a threonine at position 659 in gp41, we selected two non-BCN envelopes with sensitivity (LY109) or resistance (NYU1423) to 2F5 and 4E10. In these envelopes we mutated the conserved alanine at position corresponding to residue 659 to threonine using the Strategene site directed mutagenesis kit following the manufacturer's recommendations. The mutagenesis reaction was subjected to Dpn1 digestion and transformation using DH5α competent cells. To screen and confirm clones with the desired mutations, five clones were selected from each envelope for sequencing of the region bearing the A662T mutation. The clones with the desired A659T mutation were compared with the wild type clones in an infectivity and neutralization experiment with huMab IgG1 b12, 2F5, 4E10 and sCD4.

Example 3

Neutralization of Viruses Pseudotyped with Functional HIV-1 env Genes

Neutralization of viruses pseudotyped with envelope proteins from BCN and non-BCN donors by sera is shown in FIG. 1. Neutralization by sera from BCN donors is shown in the upper panels, and by sera from non-BCN donors is shown in the lower panels. Serum HNS2 is the reference serum from the donor of the R2 envelope protein. The BCN sera were more frequently neutralizing against both the BCN and non-BCN viruses than were the non-BCN sera. The frequency of neutralization of viruses pseudotyped with envelope proteins from BCN and non-BCN donors did not differ significantly. These results did confirm the cross-reactivity of the BCN sera, but did not demonstrate differences between the viruses expressing envelope proteins from the two different types of donors.

For each donor, approximately 10% of the Env clones screened mediated infection of Human Osteosarcoma (HOS) cells expressing CD4 and either CCR5 or CXCR4, as measured by luciferase activity. Among those that were functional, the majority had similar levels of infectivity (data not shown), and a clone with the highest apparent infectivity was selected for further characterization. The Envs generated in this study were CCR5-tropic, except for Z2Z6 and VI 1249, which displayed dual-tropism for CCR5 and CXCR4 (Quinnan et al. (1999) AIDS Res. Hum. Retroviruses 15, 561-70). The luciferase units detected in CCR5$^+$ and CXCR4$^+$ HOS cells infected with undiluted virus pseudotyped with Env Z2Z6 were 113, 379 and 693, 122 respectively. The luciferase units detected in CCR5$^+$ and CXCR4$^+$ HOS cells infected with undiluted virus pseudotyped with VI 1249 were 85,000 and 238,477 LU respectively. Unlike the R2Env, none of the novel BCN Envs mediated CD4-independent infection (data not shown).

Figure 2A:
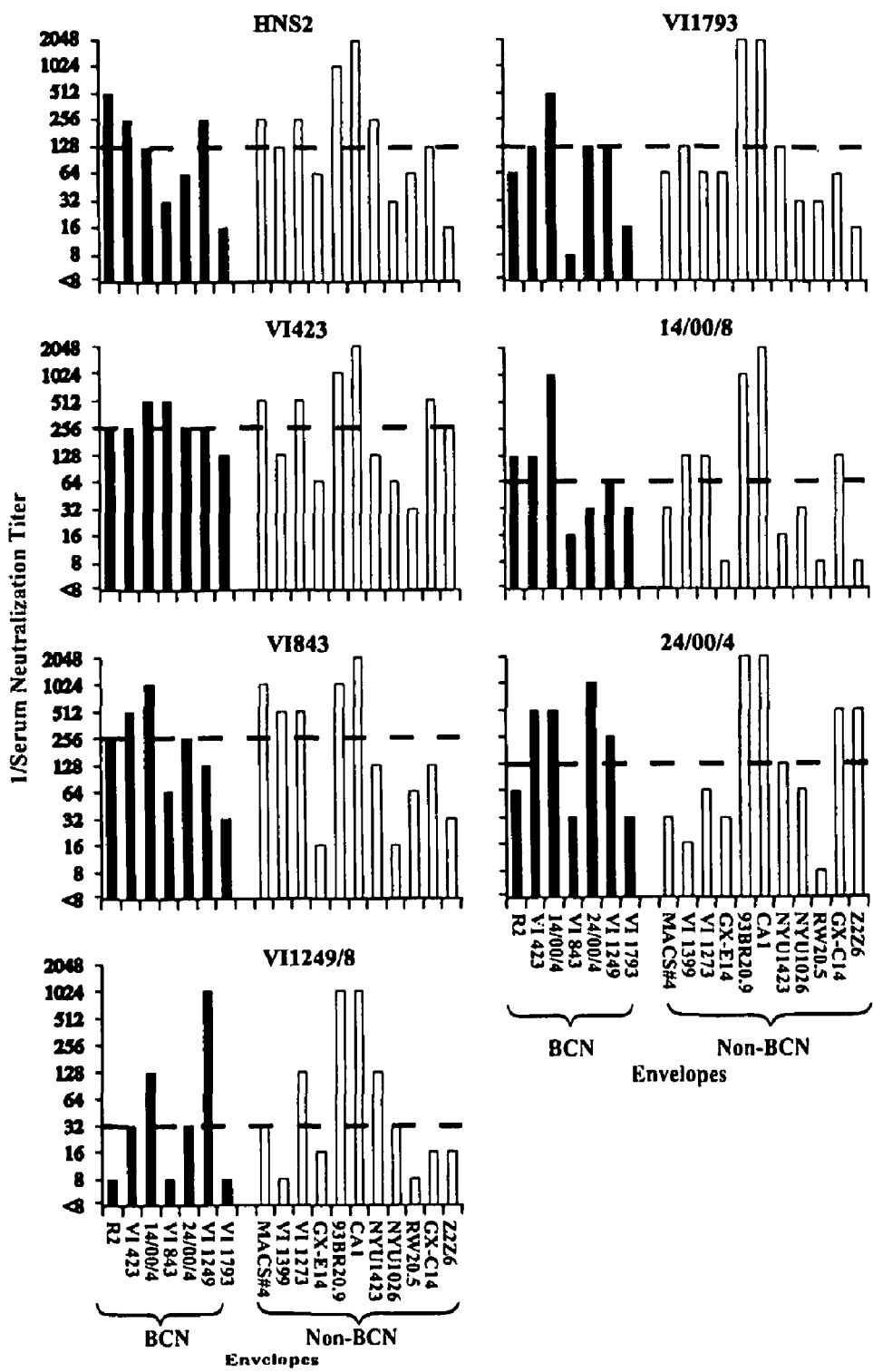
FIG. 2: Neutralization of viruses pseudotyped with Envs of BCN (■) and Non-BCN (□) donors by sera from BCN donors (Panel A) and Non-BCN donors (Panel B). Assays were performed in triplicate. Results are from single experiments, or are averages from two experiments in a few cases. Neutralization titers were defined as the highest serum dilution that resulted in greater than or equal to 50% inhibition of luciferase activity. Pseudotyped viruses VI 843, VI 1249, VI 1793, 93BR20.9 and NYU1026 were not tested for neutralization by serum from donor VI 0747. The horizontal dashed lines demonstrate the geometric mean titers of each serum against the panel of pseudotyped viruses tested. GMT of BCN sera 1:109 and GMT of non-BCN sera=1:45; p=0.01
Figure 2B:
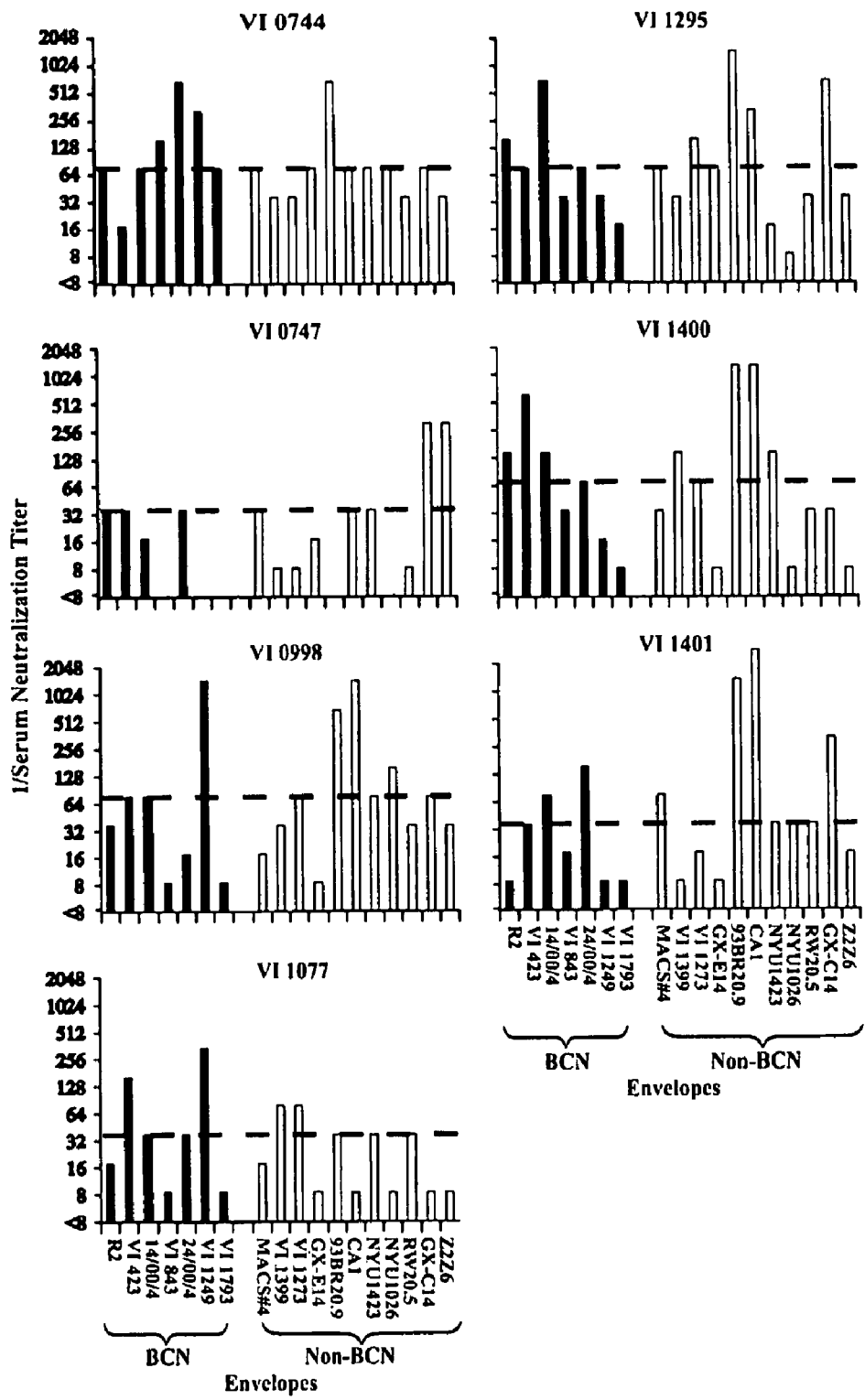
Figure 3:
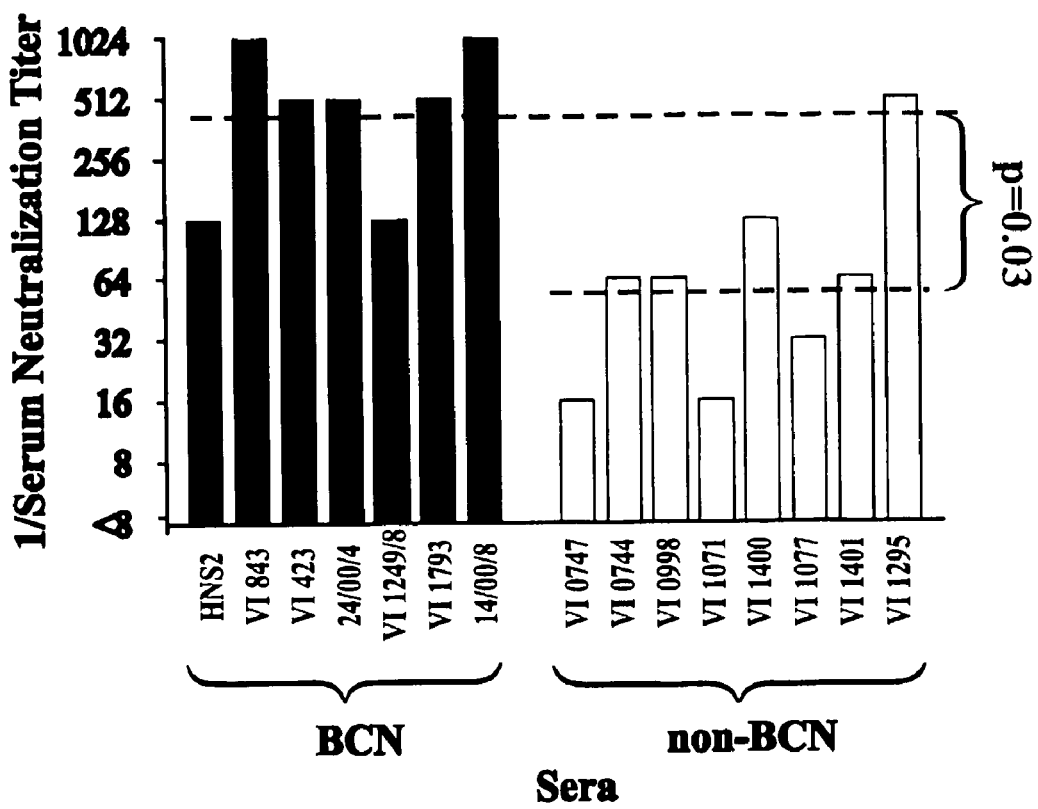
FIG. 3: Comparative neutralization of virus pseudotyped with 14/00/4 Env by BCN and Non-BCN sera. Horizontal dashed lines indicate the geometric mean titers (GMT) obtained for neutralization of 14/00/4 Env by the BCN and Non-BCN sera, respectively. The geometric means and standard deviations of the titers obtained for neutralization of 14/00/4 Env by BCN and non-BCN sera were compared by two-tailed Student t test (p=0.03 with correction factor applied for multiple comparisons).

BCN and non-BCN sera previously identified in studies by Beirnaert et. al. (2000) and Donners et. al. (2002) (Beirnaert et al. (2000) J. Med. Virol. 62, 14-24); Donners et al. (2002) AIDS 16, 501-503) were tested for neutralization of viruses pseudotyped with Envs from the seven BCN and 11 non-BCN donors. The BCN sera were samples collected 6 months after the sample used in the generation of the BCN envelope clones, except in the cases of Envs 24/00/4 and VI 423, for which the sera corresponded to the same times of the PBMC collections. Sera corresponding to the specific non-BCN Env donors used in this study were unavailable. However, the non-BCN sera used in this study were selected from a panel of serum samples classified based on low-to-absent neutralizing potency against primary isolates CA 4 (subtype F), CA 13 (subtype H) and VI 686 (group O) (Donners et al. (2002) Aids 16, 501-503). The Env subtypes of the viruses infecting the non-BCN serum donors were unavailable. As shown in FIG. 2, Panel A, the HNS2 serum and each of the other BCN sera neutralized each of the BCN and non-BCN Env pseudotyped viruses at titers ranging from 1:8 to 1:2048 (overall geometric mean titer (GMT) of the BCN sera from the ITM study=1: 109). Among the BCN sera, the one with the lowest GMT was VI 1249/8. An earlier serum from this donor was previously classified by Beirnaert et al. (2000) as having lower levels of cross-reactive neutralizing activity than sera from the other BCN donors used in the present study (Beirnaert et al. (2000) J. Med. Virol. 62, 14-24). Moreover, this donor was infected with a subtype CRF01_AE strain, and cross-reactive neutralization of non-CRF01_AE strains by such sera is expected to be low (Mascola et al. (1999) J. Virol. 73, 4009-4018). In comparison, as shown in FIG. 2, panel B, six of the seven non-BCN sera failed to neutralize one or more Env pseudotyped viruses, and the GMT for these sera was 1:45, which was significantly less than the GMT of the BCN sera (p=0.01 by Student t test). The differences in titers of the BCN and non-BCN sera remained significant if the titers against the homologous pseudotyped viruses were not included in the comparison (p=0.02). BCN and non-BCN sera neutralized two non-BCN Envs, notably CA1 and 93Br029 at titers ≧1024y. The low specificity of Env CA1 to neutralization by 14 diverse HIV-1 sera was previously observed (Nyambi et al. (1996) J. Virol. 72, 10270-102704). Virus pseudotyped with Env 14/00/4 was neutralized significantly more by the BCN than the non-BCN sera (p=0.03 by student t test, with correction for multiple comparisons), as shown in FIG. 3. None of the other Env pseudotypes was neutralized significantly more by BCN than non-BCN sera. These results suggest that the 14/00/4 Env may be sensitive to neutralizing antibodies with specificities that are more prevalent in the BCN than non-BCN sera. Serum of donor 14/00/4 was the most potent of the BCN sera described by Beirnaert et. al. (reported as serum VI 1805 in their study) (Beirnaert et al. (2000) J. Med. Virol. 62, 14-24).

Example 4

Envelope Clones from BCN and Non-BCN Donors

The sources of the HIV-1 envelope proteins used in this study are shown in Table 1. The R2 envelope protein, previously described, was included for comparison to envelope proteins derived from other BCN donors. Envelope proteins were cloned from six other donors and include two sampling dates each from Donors 14 and 24. In each case the paired samples were collected about 6 months apart. These donors were from Europe and Africa, and included envelope proteins that were of the predominant subtypes A, B, E, F, and G. The non-BCN envelope proteins were of subtypes B, A, C, D, E, F (93BR029), G (LY109), and complex (CA1), and were obtained from donors from the United States, South America, Europe, Africa, and China. All of the envelope proteins used, except R2, were CD4-dependent for infection of the reporter cells used in the assay. Infectivity shown in the Table in terms of luciferase units reflects the infectivity for HOS cells expressing both CD4 and CCR5. Cells expressing only CCR5, or CD4 and other potential coreceptors, yielded luciferase signals similar to background (i.e., approximately 100-200 luciferase units).

Example 5

Comparative Neutralization of Viruses Pseudotyped with Envelope Proteins from BCN and Non-BCN Donors by Monoclonal Antibodies and Soluble CD4 (sCD4)

Figure 4:
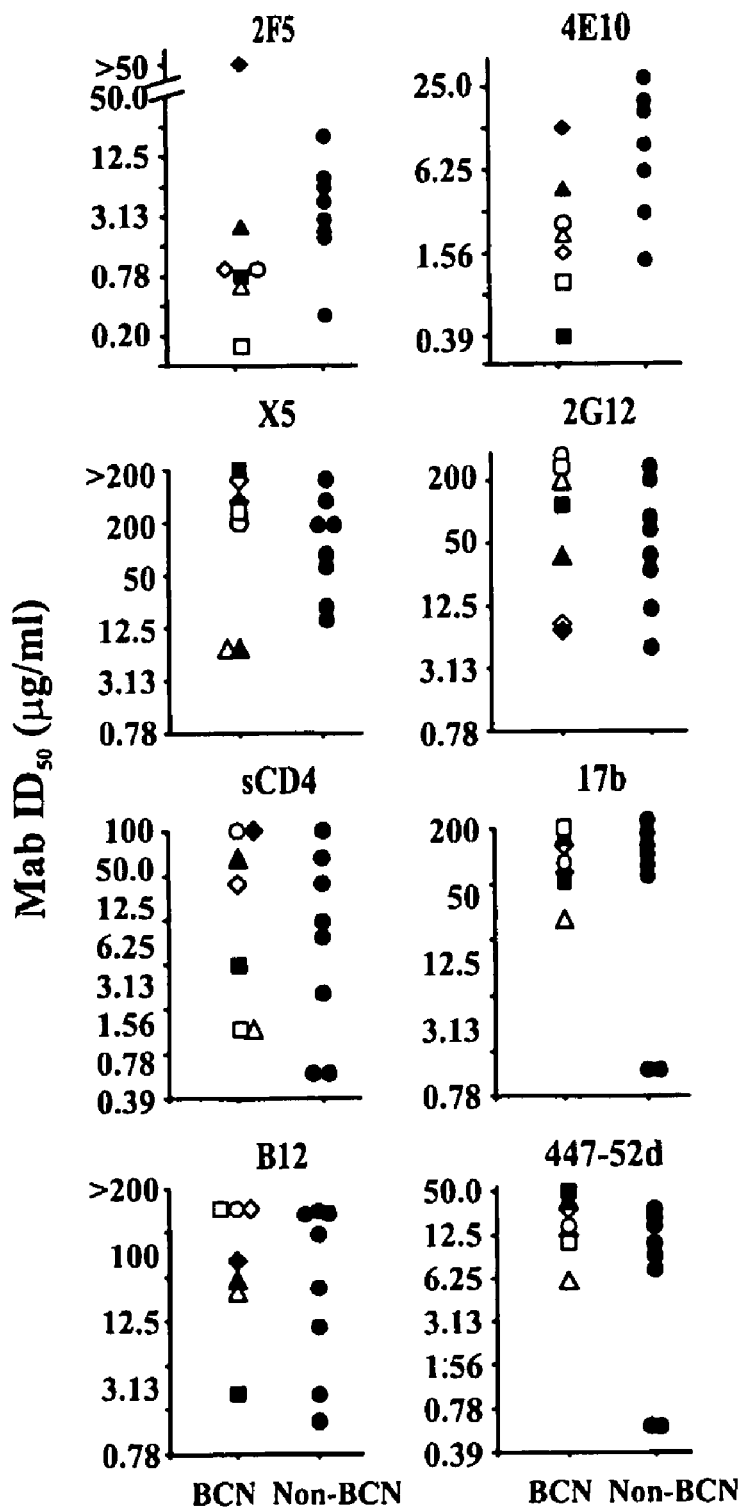
FIG. 4: Neutralization of viruses pseudotyped with BCN and Non-BCN Envs by Mabs and sCD4. Results are shown for viruses pseudotyped with the BCN and non-BCN Envs, as follows: R2 (Δ); 14/00/4 (□); 24/00/4 (○); VI 423 (▲); VI 843 (♦); VI 1249 (■); and VI 1793 (◇); all Non-BCN Env are shown as (●). Neutralization assays were performed in triplicate, and results shown are geometric means of two independent experiments. Mabs were tested for neutralization in serial two-fold dilutions. The 50% inhibitory dose ($ID_{50}$) was defined as the lowest concentration that resulted in greater than or equal to 50% inhibition of viral infectivity.

Neutralization of viruses pseudotyped with the various envelope proteins by Mabs is shown in Table 2 and FIG. 4. The sensitivity of the R2 strain to neutralization by the monoclonal antibodies and sCD4 was similar to results reported previously. Specifically, R2 virus was neutralized by sCD4 and the Mab against the CD4 binding site, and Mabs against CD4i epitopes and V3 region epitopes. It was also neutralized by the gp41 Mabs 2F5 and 4E10. In contrast, viruses pseudotyped with envelope proteins from other BCN donors were neutralized poorly, if at all by Mab against the CD4 binding site, CD4i epitopes or V3 region epitopes.

Thus, none of the other BCN envelope proteins appeared to have the CD4-independent, CD4i Mab-sensitivity phenotype of R2. Viruses pseudotyped with the envelope proteins from the non-BCN donors were variably sensitive to the various ligands.

The distribution of neutralization sensitivities of the BCN envs to the Mabs 2F5 and 4E10 was dichotomous. Viruses pseudotyped with the BCN envelope proteins were highly sensitive to neutralization by these Mabs, except for the envelope protein from donor VI843 and the envelope protein from the later sample from donor 24 (2400/8). The envelope protein from donor VI843 and the late sample from donor 24 were much more resistant than the other BCN envelope protein. The majority of the envelope protein from the non-BCN donors were more resistant to neutralization by the 2F5 and 4E10 Mabs than the group of BCN envelope proteins that were sensitive to neutralization. 2F5 neutralized six BCN Envs at $ID_{50}$ titers ranging from 0.2-3 µg/ml (FIG. 4). R2 Env assayed in parallel was also sensitive to 2F5 neutralization, consistent with a previous report (Zhang et al. (2002) J. Virol. 76, 644-655). Virus pseudotyped with BCN Env, VI 843, was resistant to neutralization by Mab 2F5 at 50 µg/ml. Meanwhile, 2F5 neutralized viruses pseudotyped with the non-BCN Envs at $ID_{50}$'s ranging from 0.39-25 µg/ml. The sensitivity of viruses pseudotyped with the non-BCN Envs to Mab 2F5 neutralization was similar to that observed in previous studies of primary HIV-1 isolates (Conley et al. (1994) Proc. Natl. Acad. Sci. 91, 3348-3352; Muster et al. (1994) J. Virol. 68, 4031-4034; Trkola et al. (1995) J. Virol. 69, 6609-6617). Most of the viruses pseudotyped with the BCN Envs were also sensitive to neutralization by Mab 4E10, with $ID_{50}$s ranging from $\leq 0.2$ to $<6.25$ µg/ml. Env VI 843, which was resistant to 2F5, displayed intermediate resistant to neutralization by Mab 4E10, with $ID_{50}=12.5$ µg/ml. The sensitivity to neutralization by 4E10 of viruses pseudotyped with the non-BCN Envs ranged from 1.56 to 25 µg/ml. One of the globally sensitive non-BCN Env 93BR029 was the most sensitive of the non-BCN Envs to neutralization by the gp41 Mabs, while the other, CA1 displayed intermediate resistance to the gp41 Mabs.

Figure 5:
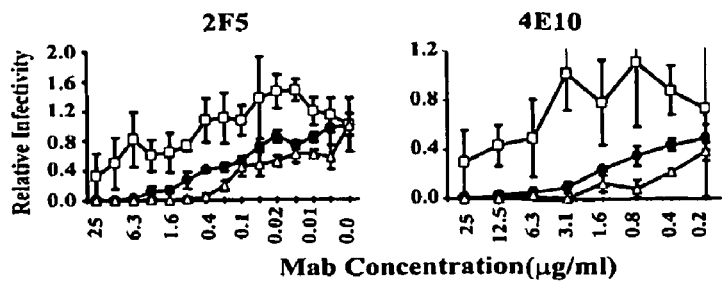
FIG. 5: Effects of Thr 662 on sensitivity to neutralization by gp41 Mabs and polyclonal serum. A: Variable sensitivity of viruses pseudotyped with early 14/00/4 (●), and late 14/00/8-33 (Δ) and 14/00/8-83 (□), Env clones from donors 14/00 to neutralization by Mabs 2F5 and 4E10. Relative infectivity is the ratio of luciferase units obtained in the presence of Mab compared to medium B: Comparative Effects of T662 and A662 on sensitivity to neutralization by the Mabs 2F5 and 4E10. Viruses pseudotyped with the 14/00/4, NYU1026, and NYU1423 Envs were compared for neutralization by the 2F5 and 4E10 Mabs. Site directed mutagenesis was used to construct the 14/00/4 (A662), NYU1026 (T662), and NYU1423 (T662) mutant Envs. Viruses pseudotyped with the wild type Envs are shown as ■, and viruses pseudotyped with the mutant Envs are shown as □. C: Comparative neutralization of virus pseudotyped with 14/00/4 (T662) (■) and 14/00/4 (A662) (□) Envs by BCN and non-BCN polyclonal serum. Serum was tested for neutralization in serial two-fold dilutions. The 50% inhibitory dose ($ID_{50}$) was defined as the lowest serum dilution that resulted in greater than or equal to 50% inhibition of viral infectivity. The $ID_{50}$ for each serum was determined by linear regression. Numbers above each bar are the differences in $ID_{50}$ of virus pseudotyped with 14/00/4 (T662) and 14/00/4 (A662) by each polyclonal serum.
Figure 5:
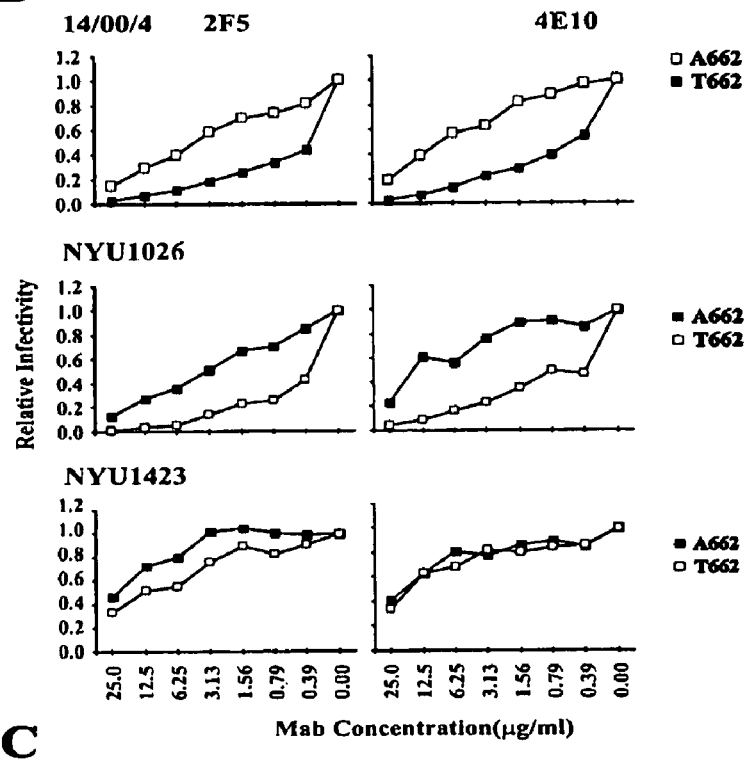
Figure 5:
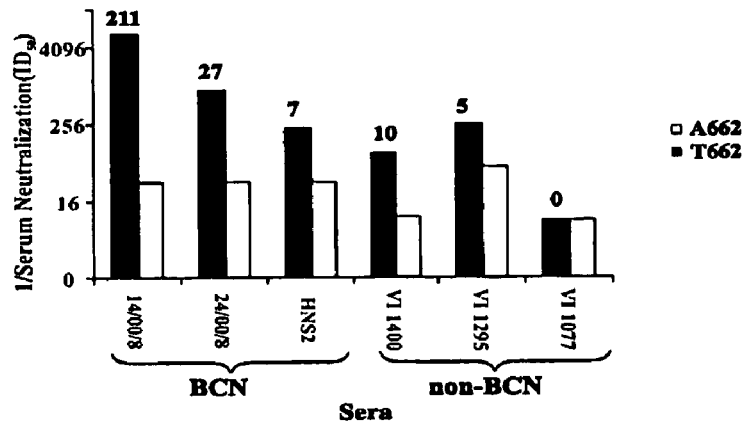
Figure 6:
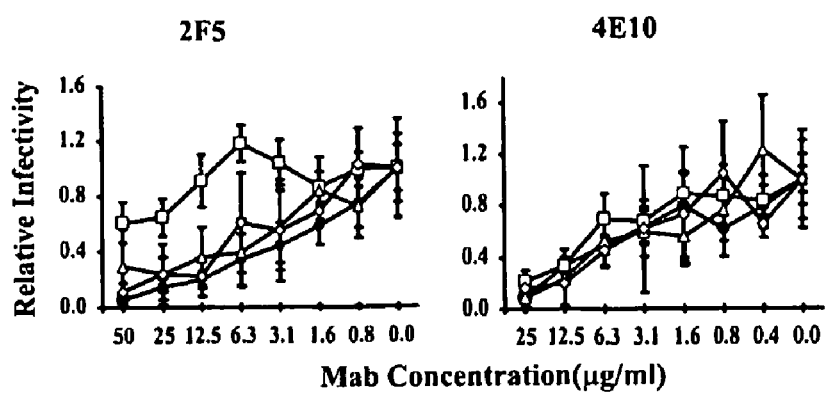
FIG. 6: Effects of the K665T mutation in Env clones of donor 2400 to neutralization by Mabs 2F5 and 4E10. A: Variable sensitivity of early 24/00/4 (●), and late 24/00/8-46 (Δ), 24/00/8-275 (◇) and 24/00/8-258 (□) Envs clones from donors 24/00 to neutralization by Mabs 2F5 and 4E10. Viruses pseudotyped with these Envs were tested for neutralization by the two Mabs. Each result shown is from one experiment, and is essentially the same as those from two replicate experiments. All experiments were performed in triplicate. B: The K665T mutation in Env 24/00/8 determines resistance to neutralization by Mab 2F5. Viruses pseudotyped with the 24/00/4 (K665) (■) and 24/00/4 (T665) (□) Env were tested for neutralization by the Mabs 2F5 and 4E10. Assays were carried out in triplicate, and results shown are averages of two independent experiments.
Figure 6:
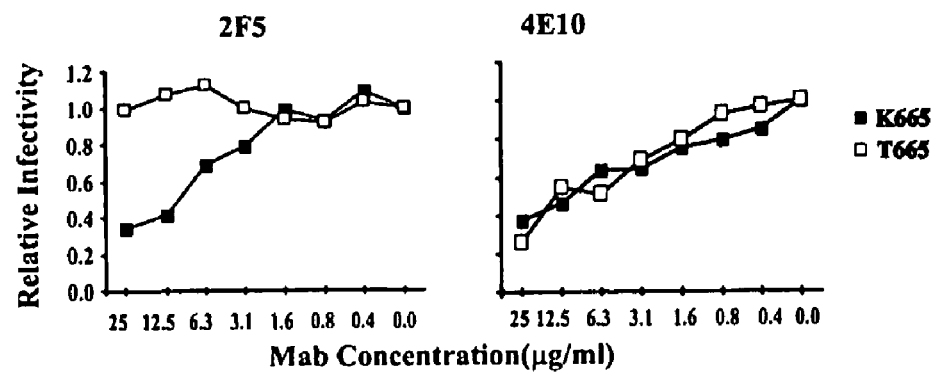

Two BCN Envs that were highly sensitive to neutralization by Mab 2F5, 14/00/4 and 24/00/4 respectively, were derived from uncultured PBMC samples of two donors with the most potent BCN antibodies as defined by Beirnaert et al. (Beirnaert et al. (2000) J. Med. Virol. 62, 14-24). These two Env were resistant to all Mabs targeting gp120 epitopes, and 24/00/4 was resistant to sCD4. Likewise, uncultured PBMC samples obtained 6 months after the sample that yielded Env clones 14/00/4 and 24/00/4 were source of additional Env clones. FIGS. 5A and 6A illustrates 2F5 and 4E10 sensitivities of viruses pseudotyped with the early and late Envs from these donors. Of two late clones from donor 14/00, designated 14/00/8-33 and 14/00/8-83, 14/00/8-33 was sensitive to neutralization by the Mabs 2F5 and 4E10, while 14/00/8-83 was relatively resistant to both monoclonal antibodies (2F5 $ID_{50}=0.01$ vs. $>12.5$ µg/ml, 4E10 $ID_{50}=0.2$ vs. 7.8 µg/ml; FIG. 5A). Of three Env clones obtained from the late sample from donor 24/00, two clones designated 24/00/8-46 and 24/00/8-275, were sensitive to neutralization by Mab 2F5, similar to Env 24/00/4 while the late clone designated 24/00/8-258 was relatively resistant (FIG. 6A). The early and late Env clones from this donor displayed similar sensitivity to Mab 4E10.

Based on these results we considered the possibility that envelope proteins from certain BCN donors may be both sensitive to neutralization by these anti-gp41 Mabs, and may induce cross-reactive neutralizing antibodies against these epitopes more efficiently than envelope protein from non-BCN donors. The late envelope protein from donor 24 (2400/8) may represent an escape mutant, which would be further evidence supporting the possibility that the donor had developed a neutralizing response directed against the 2F5/4E10 region.

Example 6

Amino Acid Sequences of the BCN Envelope Proteins

The amino acid sequences of the envelope proteins 1400/4 and 2400/4, as deduced from the results of nucleotide sequence analysis, are shown in the sequence listing as SEQ ID NO: 2 and 3. The sequences of the two proteins are generally similar to other HIV-1 envelope protein, with sequences corresponding to the predicted variable loop structures, and important landmarks in gp120 and gp41. The CD4-independence, broad neutralization sensitivity phenotype of the R2 envelope protein clone is dependent upon its unique V3 region sequence, particularly including a proline-methionine motif just proximal to the tip of the V3 loop. The locations of these residues correspond to positions 356 to 357 in clone 14/004 and 300 to 301 in clone 2400/4. The sequences of each of these clones corresponds to the two most common sequences at these positions, HI or RI. In addition, none of the other envelope protein clones from BCN donors had PM sequences at these positions (data not shown).

The sequences of the BCN envelope proteins at the 2F5 and 4E10 epitopes are shown in Table 3. The sequence recognized by the 2F5 Mab was originally mapped to the seven amino acid sequence ELDKWAS (SEQ ID NO: 1), corresponding to positions 659 to 665 (which correspond to positions 662 to 668 of the sequence of the HXB strain of HIV-1 (Reitz et al. (1994) AIDS Res. Hum. Retroviruses 10, 1143-55)) in clone 1400/4 (SEQ ID NO: 2) and 654 to 660 (which correspond to positions 662 to 668 of the sequence of the HXB strain of HIV-1 (Reitz et al. (1994) AIDS Res. Hum. Retroviruses 10, 1143-55)) in clone 2400/4 (SEQ ID NO: 3) (Muster et al. (1994) J. Virol. 68, 4031-4034; Muster et al. (1993) J. Virol. 67, 6642-6647). Subsequent additional studies have shown that binding of the Mab is influenced by sequences corresponding to the 13 amino acid sequence encompassing the primary epitope, and corresponding to positions 709 to 722 and 649 to 662 in the two clones. The sequence recognized by the Mab 4E10 has been mapped to the six amino acid sequence just distal to the 2F5 epitope, comprising the amino acids NWFDIS (SEQ ID NO: 8) at positions 668 to 673 and 663 to 668 in the two clones, respectively. The sequences of each of the BCN and non-BCN clones at these positions is shown in Table 3. A mutation in the first position of the canonical 2F5 epitope sequence (e.g., T/A) was not associated with resistance to neutralization. Mutations at the fourth position of the epitope (i.e., K/T in clone 2400/8), the 3 to 6 positions (i.e., DKWA (SEQ ID NO: 15); GKWD (SEQ ID NO: 16) in clone VI843), and the seventh position (i.e., S/G in clone NYU1423) were potentially associated with resistance to 2F5 neutralization. None of the mutations observed in the 4E10 epitope were consistently associated with resistance to neutralization by that Mab.

The significance of the K/T mutation in the 2400/8 clone at position four of the 2F5 core epitope was investigated further. Sequences corresponding to gp41 coding nucleotides were cloned using PCR from genomic DNA extracted from lymphocytes obtained on the 2400/4 and 2400/8 sampling dates. Ten or eleven clones from each sample date were sequenced in the 2F5 region, as shown in Table 4. Eight of eleven clones from the 2400/4 sample date had lysine at this position, and three had threonine. In comparison, seven of ten clones from the 2400/8 sample date had threonine at this position, and each of the other three clones had additional mutations in the 2F5 core epitope. These results indicate that the K/T mutation was common at the later date among the quasispecies present, and support the likelihood that neutralization escape mutation occurred at this epitope. The occurrence of escape mutation would indicate that donor 24 had neutralizing antibodies directed against the epitope.

The sequence of the 1400/4 clone at the 2F5 epitope was compared to other sequences in the HIV database. The E/T substitution at position 1 (corresponding to position 662 of the sequence of the HXB strain of HIV-1 (Reitz et al. (1994) AIDS Res. Hum. Retroviruses 10, 1143-55)) of the 1400/4 clone was found in only one other sequence of more than 600 in the database. The significance of this mutation was further evaluated by introduction of E/T substitutions into the NYU1423 and LY109 clones. As shown in Table 5, this substitution increased sensitivity of the clones to neutralization by the 2F5 and 4E10 Mabs, although the magnitude of the effect differed substantially between the two clones. Late envelope protein clones from the 14 donor, clones 1400/8, were prepared and evaluated for changes in 2F5 amino acid sequence. As shown in Table 6, the predominant amino acid sequence of the 2F5 epitope on each of these sample dates was TLDKWAS (SEQ ID NO: 17).

Example 7

Contribution of A662T Substitution

The 662T sequence in the Envs 14/00/4 and 14/00/8-33 is very unusual. We found one other sequence with this substitution in the HIV and GenBank databases (HIV-1 ARMA037; Accession No. AY037277) (Carr et al. (2001) Aids 15, F41-F47). To investigate whether this unusual mutation confers susceptibility to Mab 2F5 neutralization we used site directed mutagenesis to introduce the T662A mutation into clone 14/00/4, and to introduce the reverse mutation (A662T) into the non-BCN clones, NYU1026 and NYU1423, which were sensitive and resistant to Mab 2F5 neutralization, respectively. The alanine substitution into Env 14/00/4 changed it from highly sensitive to relatively resistant to neutralization by Mabs 2F5 ($ID_{50}$=0.45 vs. 6.25 µg/ml) and 4E10 ($ID_{50}$=0.9 vs. 9.34 µg/ml). Introduction of threonine at the same position of Env NYU1026 had the reverse effect on sensitivity to neutralization by Mabs 2F5 ($ID_{50}$=3.13 vs. 0.31 µg/ml) and 4E10 ($ID_{50}$=10.41 vs. 0.78 µg/ml). The magnitude of the effects of these substitutions in Envs 14/00/4 and NYU1026 are similar to the relative differences in sensitivity to neutralization by Mabs 2F5 and 4E10 of the Env clones 14/00/4 and 14/00/8-33 compared to 14/00/8-83. Introduction of threonine at the same position of Env NYU1423 caused a small, but consistent increase in sensitivity to neutralization by Mab 2F5 ($ID_{50}$=17.7 versus 10.4 µg/ml), and no significant change in sensitivity to neutralization by Mab 4E10. The results demonstrated that the presence of threonine at residue 662 is associated with increased sensitivity to neutralization by both of these Mabs, to an extent that depends on the particular Env evaluated.

Example 8

Thr662 Significantly Contributes to BCN

To further test the possible relationship of Thr 662 to induction of antibodies against the MPER of gp41, we compared sensitivity of virus pseudotyped with Envs 14/00/4 and 14/00/4 T662A mutant to neutralization by BCN (14/00/8, 24/00/8, HNS2) and non-BCN (VI 1077, VI 1295, VI 1400) sera. The T662A mutation resulted in 211 and 27-fold resistance to neutralization by serum 14/00/8 and 24/00/8, respectively. In comparison, the mutation had a lesser effect on neutralization by HNS2 serum and the non-BCN sera VI 1295, VI 1400 and VI 1077, with relative resistance of this mutant ranging from 1-10 fold. Thus, reduced sensitivity of the 14/00/4 T662A mutant to neutralization by the BCN sera 14/00/8 and 24/00/8, but not by the non-BCN sera supports the possibility that the BCN sera have relatively high neutralizing activity directed against the membrane proximal region (MPER) of gp41.

Example 9

Contribution of K665T Substitution

Previous studies have reported that the K665N mutation results in poor binding and resistance to 2F5 neutralization of HIV-1 primary isolates (Conley et al. (1994) Proc. Natl. Acad. Sci. 91, 3348-3352; Steigler et al. (2001) AIDS 17, 1757-1765). Of three late envelope clones derived from donor 24/00, one (24/00/8-258) was resistant to neutralization by Mabs 2F5, and displayed a single mutation within the 2F5 epitope sequence, K665T. To confirm the relevance of this mutation to neutralization by 2F5 we introduced the K665T point mutation into Env 24/00/4. This mutation caused resistance to 2F5, but had no effect on 4E10 sensitivity.

Example 10

Quasispecies Variations in the 2F5 and 4E10 Epitopes of BCN

To determine whether the late Envs 14/00/8-83 and 24/00/8-258, which were relatively resistant to neutralization by Mab 2F5, represented emergence of neutralization resistant escape variants in these donors, we examined quasispecies variation at the 2F5 and 4E10 epitopes in each of these donors. For this purpose, using PBMC genomic DNA as template for PCR, we cloned and analyzed amino acid sequences of the membrane proximal region of gp41 from early and late PBMC samples from these two donors. The presence of the neutralization sensitive 662T sequence in nine of 10 early and all the late gp41 clones is an indication that no dominant, neutralization resistant variant had emerged in donor 14/00. However, in donor 24/00, eight of 11 early, but only three of 10 late gp41 clones were found to have the 665 K sequence. These results indicate that neutralization resistant variants represented by clone 24/00/8-258 had emerged as the dominant populations in this donor, consistent with the emergence of neutralization escape mutants.

Example 11

Generation of BCN Response In Vivo

To study the effects of HIV-1 Env protein immunizations in mammals, including primates, administration of the antigen can be accomplished either by DNA expression vectors that produce the desired HIV Env protein or a composition comprising a purified HIV Env protein.

For a DNA expression vaccine, the DNA expression regiment and booster immunizations comprise either modified vaccinia Ankara (MVA) or VEE-RP that express the desired HIV Env protein. Similar regimens have been shown by others to induce potent CD8 T-cell responses (Horton et al. (2002) J. Virol. 76, 7187-7202; McConkey et al. (2003) Nat. Med. 9, 729-735).

For In-vivo expression vectors, VEE-RP-HIV-lenv$_{R2}$ vectors are prepared as described previously, by using pREPX-R2gp160ΔCT, pCV, and pGPm as templates for in vitro transcription of RNA (Dong et al. (2003) J. Virol. 77, 3119-3130). VEE-RP-HIV-lenv$_{R2}$ is administered in doses of $10^{6.5}$ focus forming units (FFU) at weeks 0, 1, 2, 10, 12 and 14 of the study. VEE-RP-SIVEnv is prepared by cloning of the SIV$_{mac251}$ Env protein (or variant thereof) in pRepX and then processing as for VEE-RP-HIV-lenv$_{R2}$. Dosing includes $10^{6.0}$ or $10^{7.0}$ FFU, with half to be given intravenously and half to be given subcutaneously. MVA is prepared as previously described (Horton et al. (2002) J. Virol. 76, 7187-7202). The dose of $5\times10^8$ PFU in 0.5 ml is administered intradermally in the lateral thigh. The DNA plasmid vaccine VR-SIVEnv is constructed by inserting a codon optimized SIV Env gene into VR1012 vector (Hartikka et al. (1996) Hum Gen. Ther., 7, 1205-1217). The plasmid is amplified in TOP10 cells (Invitrogen) and by using an endotoxin-free DNA purification kit (Qiagen).

Production of gp140$_{R2}$ or derivatives thereof. The gp140$_{R2}$ coding sequence is prepared by inserting two translational termination codons following the lysine residue at amino acid position 692, just prior to the predicted gp41 transmembrane region, and of arginine to serine substitutions at 517 and 520 to disrupt the protease cleavage signal (Cherpelis et al. (2001) J. Virol 75, 1547-1550; Quinnan et al. (1999) AIDS Res. Hum Retrovir. 14, 939-949). The gene is subcloned into the vaccinia vector pMCO2, linking it to a strong synthetic vaccinia virus early-late promoter (Carroll et al. (1995) Biotechniques 19, 352-354). A recombinant vaccinia virus encoding gp140$_{R2}$ (vAC4) is generated by using standard methodology (Broder et al. (1994) Mol. Biotechnol. 13, 223-245). Recombinant gp140$_{R2}$ glycoprotein is produced by infecting BS-C-1 cells, and oligomeric gp140$_{R2}$ is purified from culture supernatant by using lentil lectin Sepharose 4B affinity and size exclusion chromatography (Earl et al. (1990) J. Viol. 68, 3015-3026; Earl et al. (2001) J. Viol. 75, 645-653). The gp140$_{R2}$ is analyzed for binding activity and size.

For initial immunizations, gp140$_{R2}$, is prepared in QS-21 adjuvant (Antigenics). Each animal is given 300 μg of gp140$_{R2}$ and 150 μg of QS-21 in a total volume of one ml in two divided doses intramuscularly in the hind legs. For the final immunizations, 400 μg of oligomeric gp140$_{R2}$ is combined with 1 ml of RiBi adjuvant (Corixa) and then administered in divided doses intramuscularly in the hind legs. Control monkeys receive identical volumes of adjuvant without gp140$_{R2}$. Although gp140$_{R2}$ is cloned, purified and administered in the above example, the same procedure can be followed for any Env protein, including any desired derivatives thereof.

To summarize, genes encoding envelopes protein from donors with BCN antibodies were cloned. All of these genes were unique compared to other HIV-1 genes previously described. None of these genes shared the properties of the previously described R2 envelope protein that make it unique. The envelope proteins from the BCN donors had the common property of being relatively resistant to neutralization by Mabs against gp120 epitopes, while most were sensitive to neutralization by Mabs directed against the two gp41 epitopes, 2F5 and 4E10.

These results provide evidence of dependency of the neutralization epitopes in this region on complex structural interactions in Env. The capacity of HIV-1 Env to induce antibodies targeting these epitopes depends upon the conformation of these epitopes, and perhaps the manner in which conformational changes occur during the virus-cell interaction process. Env from donors with BCN antibodies directed against these epitopes exist in a native state, or readily assume, upon receptor/co-receptor interaction, conformations that present these MPER epitopes to B cells in immunogenic form. The capacity of a particular Env to present these epitopes likely depends upon both the specific sequence of this region of gp41, as well as the interactions between this region and other domains of the Env complex. The most direct evidence from our study that an Env from BCN donors induced neutralizing antibodies against MPER epitopes came from study of comparative serum neutralization of 14/00/4 and 14/00/4 (T662A) pseudotyped viruses. The effect of the 2F5 epitope mutation on sensitivity to neutralization was substantially greater for sera from the BCN donor 14/00 and 24/00 than from other donors. The most likely interpretation of this result is that these two sera contained relatively high levels of MPER-specific neutralizing antibodies. A converse interpretation and hypothesis are also possible. The retention of sensitivity of Envs from BCN donors to neutralization by monoclonal antibodies against the MPER, but not gp120 monoclonal antibodies, could reflect the lack of immunological selection of escape mutants in the MPER but occurrence of gp120 escape mutations. If such is the case, the sera should poses neutralizing antibodies directed predominantly against gp120 epitopes. Furthermore, the dramatic effect of the T662A mutation on neutralization by BCN sera might then reflect effects of the mutation on neutralization by antibodies directed against gp120.

Although the present invention has been described in detail with reference to examples above, it is understood that various modifications can be made without departing from the spirit of the invention. All cited patents, patent applications and publications referred to in this application are herein incorporated by reference in their entirety.

TABLE 1

Samples from Broadly Cross-Neutralizing (BCN) and Non-BCN Donors

| Donor Type | Sample | Virus subtype | Origin | date | Titers (LU) |
|---|---|---|---|---|---|
| BCN | R2 | B | U.S. | Spring 1989 | |
| | VI423 | B | Europe | May 28, 1990 | 99,690 |
| | VI843 | B | Europe | Jan. 13, 1993 | 60,102 |
| | VI1793 | A | Africa | Feb. 15, 1996 | 557,826 |
| | VI1249 | CRF01_AE | Africa | Mar. 8, 1994 | 270,937 |
| | 14/004 | F | Africa | Sep. 29, 1994 | 1,310,517 |
| | 24/004 | CRF02_AG | Africa | Nov. 15, 1994 | 778,223 |
| | 24/008 | | | May 11, 1995 | 238,477 |
| Non-BCN | MACS #4 | B | USA | | |
| | VI1273 | B | Europe | | 343,540 |
| | VI1399 | B | Europe | | 1,483,216 |
| | 93RW20.5 | A | Africa | | |
| | NYU1423 | A | Africa | | 1,124,994 |
| | GXC-44 | C | China | | |
| | Z2Z6 | D | Africa | | |
| | GXE-14 | CRF01_AE | China | | |
| | 93BR029 | B/F | S. America | | 142,795 |
| | LY109 | CRF02_AG | Africa | | 683,004 |
| | CA1 | CRF_cpx11 | Africa | | 4,225,479 |

TABLE 2

Neutralization of BCN and non-BCN strains by monoclonal antibody and soluble CD4*

| | | CD4 Binding Site | | CD4-Induced (CD4i) | | V3 | | Gp120 Surface | | | Gp41 Epitopes | |
|---|---|---|---|---|---|---|---|---|---|---|---|---|
| Envelope | Virus Subtype | sCD4 | IgG1B12 | 17b | X5 | 447-52d | 19b | 4KG5 | 2G12 | 2F5 | 4E10 | Z13 |
| BCN | | | | | | | | | | | | |
| R2 | B | 0.78 | 25 | 9.38 | <6.25 | 9.38 | 6.25 | >50 | >50 | 0.78 | 3.13 | >25 |
| VI423 | B | 50 | 31.2 | >25 | <6.25 | >25 | >50 | >50 | 25 | 1.96 | 6.25 | >25 |
| VI843 | B | >50 | 50 | >25 | >25 | >25 | >50 | >25 | 6.25 | >50 | 12.5 | >25 |
| VI1793 | A | 25 | >100 | >25 | >25 | >25 | >25 | >25 | 6.25 | 1.17 | 3.13 | >25 |
| VI1249 | AE | 3.13 | 1.56 | 25 | 25 | >25 | >50 | >50 | >50 | 0.98 | 0.98 | >25 |
| 14/004 | F | 0.59 | >100 | >25 | >25 | 18.8 | 25 | >25 | >50 | <0.39 | 1.96 | >25 |
| 24/004 | AG | >50 | >100 | >25 | >25 | >25 | >25 | >25 | >50 | 1.17 | 3.91 | >25 |
| 24/008 | AG | 4.69 | >100 | >25 | >25 | >25 | >25 | >25 | 0.78 | >50 | 25 | >25 |
| Non-BCN | | | | | | | | | | | | |
| MACS#4 | B | 1.56 | 1.56 | >25 | 25 | 18.8 | 25 | >50 | 4.69 | 3.13 | 7.82 | >25 |
| VI1273 | B | >50 | 9.38 | >25 | >25 | 12.5 | >50 | >50 | 9.38 | 3.13 | 6.25 | >25 |
| VI1399 | B | 6.25 | 0.78 | >25 | <25 | >25 | >25 | >25 | 50 | 1.56 | 3.13 | >25 |
| NYU1423 | A | 25 | >100 | >25 | 25 | >25 | >50 | >50 | 25 | 25 | 25 | ND |
| GXE-14 | AE | 9.34 | 25 | >25 | >25 | >25 | >25 | >25 | >50 | 3.13 | 13.3 | >25 |
| 93BR029 | BF | <0.39 | >100 | <0.39 | <25 | <0.39 | >50 | >50 | 18.8 | 0.39 | 0.39 | >25 |
| LY109 | AG | >25 | 100 | >25 | >25 | >25 | >25 | >25 | >25 | 6.64 | 18.8 | >25 |
| CA1 | Cpx11 | <0.39 | >100 | <0.39 | >25 | <0.39 | >50 | >50 | >50 | >12.5 | 12.5 | >25 |

*Neutralization results are shown as 50% inhibitory concentrations, given in ug/ml.

TABLE 3

Sequence analysis of the gp41 region of the 2F5 and 4E10 epitopes

| Donor | | | | Gp41 AA SEQ 657-677 | |
|---|---|---|---|---|---|
| Group | # | Subtype | SEQ ID | 2F5 | 4E10 |
| BCN | VI1793 | A | 18 | EQDLL*LDKWASLWNWFDIS | |
| | 24/004 | AG | 19 | EQDLL*LDKWASLWNWF*IS | |
| | 224/008 | AG | 20 | EQDLL*LD*WASLWNWF*IS | |
| | VI423 | B | 21 | EQELLELDKWASLWNWFDIT | |
| | VI843 | B | 22 | EQELLEL*KW*SLWSWFDIS | |
| | R2 | B | 23 | EQELLELDKWA*LWNWFDIS | |
| | VI1429 | AE | 24 | EKDLLELDKWASLWNWFDI* | |
| | 14/004 | F | 25 | EQELL*LDKWASLWNWFDIS | |
| Non-BCN | NYU1423 | A | 26 | EQDLL*LDKWA*LWNWFDIS | |
| | LY109 | AG | 27 | EQDLL*LDKWASLWNWFDI* | |
| | CA1 | Cpx11 | 28 | EQELL*LDKWASLW*WF*IS | |
| | VI1723 | B | 29 | EQELLELDKWASLWNWFDI* | |
| | VI1399 | B | 29 | EQELLELDKWASLWNWF*I* | |
| | MACS4 | B | 30 | EQELL*LDKWASLWNWFDI* | |
| | 93BR029 | BF | 31 | EKDLLELDKWASLWNWFDI* | |
| | GXE-14 | AE | 32 | | |

*Residue numbers are according to the sequence of the HXB strain of HIV-1 (Reitz et al. (1994) AIDS Res. Hum. Retroviruses 10, 1143-55).

TABLE 4

Amino acid sequences of 2F5 epitope region in envelope protein clones from samples 24/004 and 24/008

| Clones | aa 659-676 | SEQ ID |
|---|---|---|
| 2400/4 | DLLALDK-WASLWN | 33 |
| 2400/4-1 | DLLALDK-WASLWN | 33 |
| 2400/4-2 | DLLALDKW*SLWN | 34 |
| 2400/4-5 | DLLALD*WASLWN | 35 |
| 2400/4-7 | DLLALD*WASLWN | 35 |
| 2400/4-8 | DLLALDKW*SLWN | 34 |
| 2400/4-9 | DLLALDK-WASLWN | 33 |
| 2400/4-10 | DLLALDK-WASLWN | 33 |
| 2400/4-12 | DLLALDK-WASLWN | 33 |
| 2400/4-13 | DLLALD*WASLWN | 35 |
| 2400/4-14 | DLLALDKWASLWN | 33 |
| 2400/4-15 | DLLALD*WASLWN | 33 |
| 2400/8-1 | DLLALD*WASLWN | 35 |
| 2400/8-3 | DLLALDKWA*LWN | 36 |
| 2400/8-4 | DLLALD*WASLWN | 35 |
| 2400/8-6 | DLLALD*WASLWN | 35 |
| 2400/8-7 | DLLALDKW**LWN | 37 |
| 2400/8-8 | DLLALDKW**LWN | 37 |
| 2400/8-10 | DLLALD*WASLWN | 35 |
| 2400/8-11 | DLLALD*WASLWN | 35 |
| 2400/8-13 | DLLALD*WASLWN | 35 |
| 2400/8-16 | DLLALD*WASLWN | 35 |

TABLE 5

Effects of the N662T Mutation in the 2F5 Core Epitope on Sensitivity to Neutralization by the 2F5 and 4E10 Mabs

| | Mab ID$_{50}$ | |
|---|---|---|
| Envelope protein | 2F5 | 4E10 |
| NYU1423 | 25 | 25 |
| NYU1423(N662T) | 12.5 | 12.5 |
| LY109 | 3.1 | 12.5 |
| LY109(N662T) | 0.39 | 0.78 |

TABLE 6

Amino acid sequences of 2F5 epitope region in envelope clones from samples 1400/4 and 1400/8

| Clones | aa 659-676 | SEQ ID |
|---|---|---|
| 14/004-3 | ELLTLDK-WASLWN | 38 |
| 14/004-4 | ELLTLDKWA*LWN | 39 |
| 14/004-5 | ELL*LDKWASLWN | 40 |
| 14/004-6 | ELLTLDK-WASLWN | 38 |
| 14/004-7 | ELLTLDK-WASLWN | 38 |
| 14/004-8 | ELLTLDK-WASLWN | 38 |
| 14/008-1 | ELLTLDK-WASLWN | 38 |
| 14/008-2 | ELLTLDK-WASLWN | 38 |
| 14/008-3 | ELLTLDK-WASLWN | 38 |
| 14/008-4 | ELLTLDK-WASLWN | 38 |
| 14/008-5 | ELLTLDK-WASLWN | 38 |
| 14/008-6 | ELLTLDK-WASLWN | 38 |
| 14/008-7 | ELLTLDK-WASLWN | 38 |
| 14/008-8 | ELLTLDK-WASLWN | 38 |
| 14/008-9 | ELLTLDK-WASLWN | 38 |
| 14/008-10 | ELLTLDK-WASLWN | 38 |
| 14/008-11 | ELLTLDK-WASLWN | 38 |
| 14/008-12 | ELLTLDK-WASLWN | 38 |
| 14/008-13 | ELLTLDK-WASLWN | 38 |

What is claimed:

1. An isolated HIV-1 envelope protein comprising SEQ ID NO:2, comprising at least one epitope which induces a broadly cross reactive antibody response following administration in a human.

2. The isolated HIV-1 envelope protein of claim 1 consisting of SEQ ID NO:2.

3. An isolated nucleic acid molecule encoding the isolated HIV-1 envelope protein of claim 1.

4. The isolated nucleic acid molecule of claim 3 comprising SEQ ID NO:50.

5. The isolated nucleic acid molecule of claim 3 consisting of SEQ ID NO:50.

6. The isolated nucleic acid molecule of claim 3 wherein said nucleic acid molecule is operably linked to one or more expression control elements.

7. A vector comprising an isolated nucleic acid molecule of claim 3.

8. An isolated host cell transformed to contain the nucleic acid molecule of claim 3.

9. An isolated host cell comprising the vector of claim 7.

10. The isolated host cell of claim 9, wherein said host cell is selected from the group consisting of prokaryotic host cells and eukaryotic host cells.

11. A method for producing a polypeptide comprising culturing an isolated host cell transformed with the nucleic acid molecule of claim 3 under conditions in which the polypeptide encoded by said nucleic acid molecule is expressed.

12. A composition comprising the isolated HIV-1 envelope protein of claim 1 and a pharmaceutically acceptable carrier.

13. The composition of claim 12 wherein the composition is an immunogenic composition.

14. A fusion protein comprising the isolated HIV-1 envelope protein of claim 1.

15. A method of generating antibodies in a mammal comprising administering one or more of the isolated HIV-1 envelope proteins of claim 1 in an amount sufficient to induce the production of the antibodies.

16. A method of generating antibodies in a mammal comprising administering the isolated nucleic acid molecule of claim 3 in an amount sufficient to express levels of the HIV-1 envelope protein to induce the production of the antibodies.

* * * * *

SEQUENCE LISTING

<160> NUMBER OF SEQ ID NOS: 55

<210> SEQ ID NO 1
<211> LENGTH: 7
<212> TYPE: PRT

-continued

<213> ORGANISM: Human immunodeficiency virus type 1

<400> SEQUENCE: 1

Glu Leu Asp Lys Trp Ala Ser
1               5

<210> SEQ ID NO 2
<211> LENGTH: 853
<212> TYPE: PRT
<213> ORGANISM: Human immunodeficiency virus type 1

<400> SEQUENCE: 2

```
Met Arg Val Arg Gly Met Gln Arg Asn Trp Gln His Leu Gly Lys Trp
1               5                   10                  15

Gly Leu Leu Phe Leu Gly Ile Leu Ile Ile Cys Asn Ala Ala Asp Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Gly Tyr Glu Lys Glu Val
    50                  55                  60

His Asn Val Trp Ala Thr His Ala Cys Val Pro Thr Asp Pro Asn Pro
65                  70                  75                  80

Gln Glu Val Val Leu Lys Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Phe Asn Gly Asn Thr Thr Asp Gln Asn Ser Thr Leu
    130                 135                 140

Lys Glu Glu Ser Gly Ala Ile Gln Asp Cys Ser Phe Asn Met Thr Thr
145                 150                 155                 160

Glu Val Arg Asp Lys Glu Leu Gln Val His Ala Leu Phe Tyr Arg Leu
                165                 170                 175

Asp Ile Val Pro Ile Ser Gly Ser Asn Asp Ser Ser Gly Asn Gly Lys
            180                 185                 190

Tyr Arg Leu Ile Asn Cys Asn Thr Ser Thr Ile Arg Gln Ala Cys Pro
        195                 200                 205

Lys Val Ser Trp Asp Pro Ile Pro Ile His Tyr Cys Ala Pro Ala Gly
    210                 215                 220

Tyr Ala Ile Leu Lys Cys Asn Asp Lys Lys Phe Asn Gly Thr Gly Pro
225                 230                 235                 240

Cys Gln Asn Val Ser Thr Val Gln Cys Thr His Gly Ile Lys Pro Val
                245                 250                 255

Val Ser Thr Gln Leu Leu Leu Asn Gly Ser Leu Ala Glu Glu Ser Ile
            260                 265                 270

Ile Ile Arg Ser Gln Asn Ile Ser Asp Asn Thr Lys Thr Ile Ile Val
        275                 280                 285

His Leu Asn Glu Ser Ile Gln Ile Asn Cys Thr Arg Pro Asn Asn Asn
    290                 295                 300

Thr Arg Lys Gly Ile His Ile Gly Pro Gly Gln Ala Phe Tyr Ala Thr
305                 310                 315                 320

Gly Glu Ile Ile Gly Asp Ile Arg Lys Ala His Cys Asn Ile Ser Arg
                325                 330                 335

Gly Gln Trp Arg Lys Thr Leu Lys Gln Val Glu Ala Glu Leu Lys Pro
            340                 345                 350
```

```
His Phe Asn Asn Asn Thr Ile Glu Phe Lys Pro Pro Pro Gly Gly
            355                 360                 365

Asp Leu Glu Ile Thr Met His Ser Phe Asn Cys Arg Gly Glu Phe Phe
        370                 375                 380

Tyr Cys Asn Thr Ser Gly Leu Phe Asn Thr Asn Thr Ser Gly Gln Phe
385                 390                 395                 400

Asn Thr Thr Gly Ser Asn Glu Thr Ile Val Leu Pro Cys Lys Ile Lys
                405                 410                 415

Gln Ile Val Arg Met Trp Gln Gly Val Gly Gln Ala Met Tyr Ala Pro
            420                 425                 430

Pro Ile Ala Gly Asn Ile Thr Cys Asn Ser Asn Ile Thr Gly Leu Leu
                435                 440                 445

Leu Thr Arg Asp Gly Gly Asn Ser Ser Asn Ala Asn Ala Asn Glu Thr
            450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Glu Pro Leu Gly Val Ala Pro Thr
                485                 490                 495

Gly Ala Lys Arg Gln Val Val Lys Arg Glu Lys Arg Ala Val Gly Met
            500                 505                 510

Gly Ala Leu Phe Leu Gly Phe Leu Gly Ala Ala Gly Ser Thr Met Gly
            515                 520                 525

Ala Ala Ser Ile Thr Leu Thr Val Gln Ala Arg Gln Leu Leu Ser Gly
            530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Leu
            580                 585                 590

Trp Gly Cys Ser Gly Lys Leu Ile Cys Thr Thr Asn Val Pro Trp Asn
            595                 600                 605

Ser Ser Trp Ser Asn Lys Ser Gln Glu Glu Ile Trp Glu Asn Met Thr
610                 615                 620

Trp Met Glu Trp Glu Arg Glu Ile Ser Asn Tyr Ser Asp Glu Ile Tyr
625                 630                 635                 640

Arg Leu Ile Glu Leu Ser Gln Asn Gln Gln Glu Lys Asn Glu Gln Glu
                645                 650                 655

Leu Leu Thr Leu Asp Lys Trp Ala Ser Leu Trp Asn Trp Phe Asp Ile
            660                 665                 670

Ser His Trp Leu Trp Tyr Ile Arg Ile Phe Ile Met Ile Val Gly Gly
            675                 680                 685

Leu Ile Gly Leu Arg Ile Ile Phe Ala Val Leu Ser Ile Val Asn Arg
        690                 695                 700

Val Arg Lys Gly Tyr Ser Pro Val Ser Leu Gln Thr Leu Ile Pro Ser
705                 710                 715                 720

Pro Arg Glu Pro Ala Arg Pro Glu Gly Ile Glu Gly Asp Gly Glu
                725                 730                 735

Glu Asp Lys Asp Arg Ser Val Arg Leu Val Asn Gly Phe Leu Ala Leu
            740                 745                 750

Val Trp Asp Asp Leu Arg Asn Leu Cys Leu Phe Ser Tyr Arg Arg Leu
        755                 760                 765

Arg Asp Phe Ile Leu Ile Ala Ala Arg Ile Val Asp Arg Gly Leu Thr
```

```
                    770                 775                 780
Arg Gly Trp Glu Ala Leu Lys Tyr Leu Trp Asn Leu Ala Gln Tyr Trp
785                 790                 795                 800

Ser Arg Glu Leu Lys Asn Ser Ala Ile Ser Leu Phe Asp Thr Ile Ala
                805                 810                 815

Ile Ile Val Ala Glu Gly Thr Asp Arg Val Ile Glu Ala Leu Gln Arg
            820                 825                 830

Ala Gly Arg Ala Val Leu Asn Val Pro Arg Arg Ile Arg Gln Gly Leu
        835                 840                 845

Glu Arg Ala Leu Leu
    850

<210> SEQ ID NO 3
<211> LENGTH: 856
<212> TYPE: PRT
<213> ORGANISM: Human immunodeficiency virus type 1

<400> SEQUENCE: 3

Met Arg Val Met Gly Ile Gln Arg Asn Tyr Pro Leu Leu Trp Arg Trp
1               5                   10                  15

Gly Met Thr Ile Phe Trp Leu Met Met Ile Cys Asn Ala Glu Asn Leu
            20                  25                  30

Trp Val Thr Val Tyr Tyr Gly Val Pro Val Trp Lys Asp Ala Lys Thr
        35                  40                  45

Thr Leu Phe Cys Ala Ser Asp Ala Lys Ala Tyr Asp Thr Glu Val His
    50                  55                  60

Asn Val Trp Ala Thr His Ala Cys Val Pro Thr Asp Pro Asn Pro Gln
65                  70                  75                  80

Glu Met Asp Leu Lys Asn Val Thr Glu Asn Phe Asn Met Trp Lys Asn
                85                  90                  95

Asn Met Val Glu Gln Met His Glu Asp Ile Ile Ser Leu Trp Asp Gln
            100                 105                 110

Ser Leu Lys Pro Cys Val Gln Leu Thr Pro Leu Cys Val Thr Leu Asp
        115                 120                 125

Cys His Asn Tyr Asn Ser Ser Asn Asp Asn Pro Pro Gly Gln Glu Val
    130                 135                 140

Lys Asn Cys Ser Phe Asn Met Thr Thr Glu Leu Arg Asp Lys Arg Gln
145                 150                 155                 160

Lys Val Tyr Ala Leu Phe Tyr Arg Ile Asp Val Val Pro Leu Ser Asn
                165                 170                 175

Ser Ser Asn Ser Ser Gln Tyr Ser Leu Ile Asn Cys Asn Thr Ser Ala
            180                 185                 190

Ile Thr Gln Ala Cys Pro Lys Val Ser Phe Asp Pro Ile Pro Ile His
        195                 200                 205

Tyr Cys Ala Pro Ala Gly Phe Ala Ile Leu Lys Cys Lys Asp Lys Lys
    210                 215                 220

Phe Asn Gly Ala Gly Pro Cys Asn Asn Val Ser Thr Val Gln Cys Thr
225                 230                 235                 240

His Gly Ile Lys Pro Val Val Ser Thr Gln Leu Leu Leu Asn Gly Ser
                245                 250                 255

Leu Ala Glu Gly Glu Val Val Ile Arg Ser Glu Asn Ile Ser Asn Asn
            260                 265                 270

Ala Lys Thr Ile Ile Val Gln Leu Val Glu Pro Ile Arg Ile Asn Cys
        275                 280                 285

Thr Arg Pro Gly Asn Asn Thr Arg Lys Ser Val Arg Ile Gly Pro Gly
```

```
                       290                 295                 300
Gln Thr Phe Tyr Ala Asn Glu Val Ile Gly Asn Ile Arg Gln Ala His
305                 310                 315                 320

Cys Asn Val Ser Arg Ser Asp Trp Asn Lys Thr Leu Gln Gln Val Ala
                325                 330                 335

Val Gln Leu Gly Lys Gln Phe Glu Asn Lys Thr Ile Ile Phe Lys Glu
            340                 345                 350

His Ser Gly Gly Asp Val Glu Ile Thr Thr His Ser Phe Asn Cys Arg
        355                 360                 365

Gly Glu Phe Phe Tyr Cys Asn Thr Pro Ile Leu Phe Asn Ser Thr Trp
370                 375                 380

Glu Tyr Asn Ser Thr Trp Gly Asn Tyr Ser Ser Asn Tyr Thr Gly Ser
385                 390                 395                 400

Asn Asp Ile Ile Thr Leu Gln Cys Lys Ile Lys Gln Ile Val Asn Met
                405                 410                 415

Trp Gln Lys Val Gly Gln Ala Met Tyr Ala Pro Pro Ile Pro Gly Glu
            420                 425                 430

Leu Arg Cys Glu Ser Asn Ile Thr Gly Leu Leu Leu Thr Arg Asp Gly
        435                 440                 445

Gly Thr Asn Ser Thr Asn Glu Thr Phe Glu Thr Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr His Ala Lys Arg Arg
                485                 490                 495

Val Val Gln Arg Glu Lys Arg Ala Val Gly Leu Gly Ala Val Phe Leu
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
530                 535                 540

Asn Asn Leu Leu Arg Ala Ile Glu Ala Gln Gln His Leu Leu Lys Leu
545                 550                 555                 560

Thr Val Trp Gly Ile Lys Gln Leu Gln Ala Arg Val Leu Ala Leu Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Thr Val Pro Trp Asn Ser Thr Trp Ser Asn
        595                 600                 605

Lys Thr Tyr Lys Glu Ile Trp Asp Asn Met Thr Trp Leu Glu Trp Asp
610                 615                 620

Lys Glu Ile Ser Arg Tyr Thr Asn Ile Ile Tyr Asp Leu Ile Glu Glu
625                 630                 635                 640

Ser Gln Asn Gln Gln Glu Lys Asn Glu Gln Asp Leu Leu Ala Leu Asp
                645                 650                 655

Lys Trp Ala Ser Leu Trp Asn Trp Phe Asn Ile Ser Asn Trp Leu Trp
            660                 665                 670

Tyr Ile Arg Ile Phe Ile Met Ile Val Gly Gly Leu Ile Gly Leu Arg
        675                 680                 685

Ile Val Phe Ala Val Leu Ala Ile Ile Asn Arg Val Arg Gln Gly Tyr
690                 695                 700

Ser Pro Leu Ser Phe Gln Thr Leu Thr His Gln Gln Arg Glu Gln Pro
705                 710                 715                 720
```

```
Asp Arg Pro Glu Arg Ile Glu Glu Gly Gly Glu Gln Asp Arg Asp
            725                 730                 735

Arg Ser Val Arg Leu Val Ser Gly Phe Leu Ala Leu Ala Trp Asp Asp
        740                 745                 750

Leu Arg Ser Leu Cys Leu Phe Ser Tyr His Arg Leu Arg Asp Phe Val
        755                 760                 765

Leu Ile Ala Thr Arg Thr Val Glu Leu Leu Gly His Ser Ser Leu Lys
        770                 775                 780

Gly Leu Arg Leu Gly Trp Glu Ala Leu Lys Tyr Leu Trp Ser Leu Leu
785                 790                 795                 800

Ser Tyr Trp Gly Gln Glu Leu Lys Asn Ser Ala Ile Ser Leu Leu Asp
            805                 810                 815

Thr Thr Ala Ile Ala Val Ala Asn Trp Thr Asp Arg Val Ile Glu Ile
        820                 825                 830

Gly Gln Arg Ile Gly Arg Ala Ile Trp Asn Ile Pro Thr Arg Ile Arg
        835                 840                 845

Gln Gly Ile Glu Arg Ala Leu Leu
        850                 855

<210> SEQ ID NO 4
<211> LENGTH: 848
<212> TYPE: PRT
<213> ORGANISM: Human immunodeficiency virus type 1

<400> SEQUENCE: 4

Met Arg Val Arg Gly Ile Arg Arg Asn Cys Gln His Leu Trp Lys Trp
1               5                   10                  15

Gly Thr Met Leu Leu Gly Ile Leu Met Ile Cys Asn Ala Thr Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Met Glu Leu Lys Asn Val Thr Glu Asn Phe Asn Met Trp Lys
            85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Thr Ser Ser Ser Gly
    130                 135                 140

Glu Thr Met Glu Gly Gly Glu Met Lys Asn Cys Ser Phe Asn Ile Thr
145                 150                 155                 160

Thr Ser Ile Arg Asp Lys Leu Gln Lys Val Tyr Ala Leu Phe Tyr Lys
            165                 170                 175

Leu Asp Val Thr Pro Ile Glu Asn Asp Thr Thr Ser Tyr Arg Leu Ile
        180                 185                 190

Ser Cys Asn Thr Ser Val Ile Thr Gln Ala Cys Pro Lys Ile Ser Phe
        195                 200                 205

Glu Pro Ile Pro Ile His Tyr Cys Ala Pro Ala Gly Phe Ala Ile Leu
    210                 215                 220

Lys Cys Lys Asp Thr Lys Phe Asn Gly Thr Gly Pro Cys Thr Asn Val
225                 230                 235                 240
```

```
Ser Thr Val Gln Cys Thr His Gly Ile Lys Pro Val Ser Thr Gln
            245                 250                 255

Leu Leu Leu Asn Gly Ser Leu Ala Glu Glu Val Val Ile Arg Ser
            260                 265                 270

Ser Asn Phe Thr Asp Asn Thr Val Ile Ile Val Gln Leu Asn Asn
            275                 280                 285

Val Glu Ile Asn Cys Thr Arg Pro Asn Asn Asn Lys Thr Arg Lys Ser
            290                 295                 300

Ile Pro Ile Gly Pro Gly Arg Ala Phe Tyr Thr Thr Gly Glu Ile Ile
305                 310                 315                 320

Gly Asp Ile Arg Gln Ala His Cys Asn Leu Ser Gly Ala Lys Trp Asn
                325                 330                 335

Asp Ala Leu Lys Gln Ile Val Thr Lys Leu Arg Glu Gln Phe Lys Asn
            340                 345                 350

Lys Thr Ile Ile Phe Asn Gln Ser Ser Gly Gly Asp Pro Glu Ile Val
            355                 360                 365

Thr His Ser Phe Asn Cys Gly Gly Glu Phe Phe Tyr Cys Asn Thr Thr
    370                 375                 380

Lys Leu Phe Asn Ser Thr Trp Asn Gly Thr Glu Gly Ser Asn Asn Thr
385                 390                 395                 400

Gly Gly Glu Asn Asp Thr Ile Thr Leu Pro Cys Arg Ile Lys Gln Ile
                405                 410                 415

Val Asn Met Trp Gln Glu Val Gly Lys Ala Met Tyr Ala Pro Pro Ile
            420                 425                 430

Arg Gly Gln Ile Arg Cys Ser Ser Asn Ile Thr Gly Leu Ile Leu Thr
            435                 440                 445

Arg Asp Gly Gly Asn Asn Asn Thr Asn Glu Thr Phe Arg Pro Gly
450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Ala Lys Arg
                485                 490                 495

Arg Val Val Gln Arg Glu Lys Arg Ala Ile Ala Gly Ala Val Phe Leu
            500                 505                 510

Gly Phe Leu Gly Ala Ala Gly Ser Thr Met Gly Ala Ala Ser Val Ala
        515                 520                 525

Leu Thr Val Gln Ala Arg Leu Leu Leu Ser Gly Ile Val Gln Gln Gln
    530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
            565                 570                 575

Arg Tyr Leu Arg Asp Gln Gln Leu Leu Gly Ile Trp Gly Cys Ser Gly
        580                 585                 590

Lys Leu Ile Cys Thr Thr Thr Val Pro Trp Asn Thr Ser Trp Ser Asn
            595                 600                 605

Lys Ser Val Asp Tyr Ile Trp Lys Asn Met Thr Trp Met Gln Trp Glu
        610                 615                 620

Lys Glu Ile Asp Asn Tyr Thr Ser Leu Ile Tyr Thr Leu Ile Glu Glu
625                 630                 635                 640

Ser Gln Tyr Gln Gln Glu Lys Asn Glu Gln Glu Leu Leu Glu Leu Asp
                645                 650                 655

Lys Trp Ala Ser Leu Trp Asn Trp Phe Asp Ile Thr Asn Trp Leu Trp
            660                 665                 670
```

```
Tyr Ile Lys Leu Phe Ile Met Ile Val Gly Gly Leu Val Gly Leu Arg
            675                 680                 685

Ile Val Phe Ala Val Leu Ser Ile Val Asn Arg Val Arg Gln Gly Tyr
        690                 695                 700

Ser Pro Leu Ser Phe Gln Thr Arg Pro Pro Ala Pro Arg Gly Pro Asp
705                 710                 715                 720

Arg Pro Glu Gly Ile Glu Glu Gly Gly Glu Arg Asn Arg Asp Arg
                725                 730                 735

Ser Glu Gln Leu Val Asp Gly Phe Leu Ala Leu Ile Trp Ile Asp Leu
                740                 745                 750

Arg Ser Leu Cys Leu Phe Ile Tyr His Arg Leu Arg Asp Leu Leu Leu
            755                 760                 765

Ile Val Thr Arg Ile Val Glu Leu Leu Gly Arg Arg Gly Trp Glu Ile
        770                 775                 780

Leu Lys Tyr Trp Trp Asn Leu Leu Gln Tyr Trp Ser Gln Glu Leu Lys
785                 790                 795                 800

Asn Ser Ala Val Ser Leu Phe Asn Ala Thr Ala Ile Ala Val Ala Glu
                805                 810                 815

Gly Thr Asp Arg Val Ile Glu Ile Leu Gln Arg Ala Phe Arg Ala Thr
                820                 825                 830

Leu His Ile Pro Thr Arg Ile Arg Gln Gly Leu Glu Arg Ala Leu Leu
            835                 840                 845

<210> SEQ ID NO 5
<211> LENGTH: 851
<212> TYPE: PRT
<213> ORGANISM: Human immunodeficiency virus type 1

<400> SEQUENCE: 5

Met Lys Val Lys Glu Ile Arg Lys Asn Cys Arg His Leu Trp Arg Trp
1               5                   10                  15

Gly Thr Met Leu Leu Gly Met Leu Met Ile Cys Ser Ala Thr Glu Lys
                20                  25                  30

Leu Trp Val Thr Val Tyr Tyr Gly Val Pro Val Trp Lys Glu Thr Asp
            35                  40                  45

Thr Thr Leu Phe Cys Ala Ser Asp Ala Lys Ala Tyr Asp Arg Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met Gln Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Ala Pro Asn Val Thr Asn Thr Asn Ser Thr Asn Thr
        130                 135                 140

Asn Asn Ser Ser Leu Asp Glu Gly Glu Met Lys Asn Cys Ser Phe Asn
145                 150                 155                 160

Ile Thr Thr Ser Ile Lys Asp Lys Ile Gln Arg Glu Tyr Ala Leu Phe
                165                 170                 175

Tyr Arg Leu Asp Ile Val Pro Ile Asp Gly Ser Asn Ser Ser Tyr Arg
                180                 185                 190

Leu Thr Lys Cys Asn Thr Ser Val Ile Thr Gln Ala Cys Pro Lys Val
            195                 200                 205
```

```
Thr Phe Glu Pro Ile Pro Ile His Tyr Cys Ala Pro Ala Gly Phe Ala
    210                 215                 220
Ile Leu Lys Cys Asn Asp Lys Lys Phe Asn Gly Thr Gly Pro Cys Lys
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Val Ile Ile
            260                 265                 270
Arg Ser Glu Asn Phe Ser Asp Asn Ala Lys Asn Ile Ile Val His Leu
        275                 280                 285
Asn Glu Ser Val Glu Ile Asn Cys Thr Arg Pro Ser Asn Asn Thr Arg
    290                 295                 300
Lys Ser Ile His Met Gly Pro Gly Gly Ala Ile Tyr Ala Thr Gly Lys
305                 310                 315                 320
Ile Ile Gly Asp Ile Arg Gln Ala His Cys Asn Ile Ser Glu Lys Lys
                325                 330                 335
Trp Gly Glu Ala Leu Glu Arg Ile Val Lys Lys Leu Arg Lys Gln Tyr
            340                 345                 350
Asn Asn Thr Ile Ile Phe Thr Gln Pro Ser Gly Gly Asp Pro Glu Ile
        355                 360                 365
Val Met His Ser Phe Asn Cys Gly Gly Glu Phe Phe Tyr Cys Asn Thr
    370                 375                 380
Ser Gln Leu Phe Asn Thr Thr Trp Ser Asp Thr Thr Trp Asn Asn
385                 390                 395                 400
Thr Asn Asn Thr Asn Gly Asn Ile Thr Leu Pro Cys Arg Ile Lys Gln
                405                 410                 415
Ile Ile Asn Met Trp Gln Gly Val Gly Lys Ala Met Tyr Ala Pro Pro
            420                 425                 430
Ile Ser Gly Gln Ile Arg Cys Ser Ser Asn Ile Thr Gly Leu Ile Leu
        435                 440                 445
Thr Arg Asp Gly Gly Leu Ala Asn Arg Thr Lys Glu Thr Phe Arg Pro
    450                 455                 460
Gly Gly Gly Asp Met Arg Asp Asn Trp Arg Ser Glu Leu Tyr Lys Tyr
465                 470                 475                 480
Lys Val Val Lys Ile Glu Pro Leu Gly Val Ala Pro Thr Lys Ala Lys
                485                 490                 495
Arg Arg Val Val Gln Arg Glu Lys Arg Ala Val Gly Met Leu Gly Ala
            500                 505                 510
Val Phe Leu Gly Phe Leu Gly Ala Ala Gly Ser Thr Met Gly Ala Ala
        515                 520                 525
Ser Ile Thr Leu Thr Val Gln Ala Arg Gln Leu Leu Ser Gly Ile Val
    530                 535                 540
Gln Gln Gln Asn Asn Leu Leu Lys Ala Ile Glu Ala Gln Gln His Leu
545                 550                 555                 560
Leu Gln Leu Thr Val Trp Gly Ile Lys Gln Leu Gln Ala Arg Val Leu
                565                 570                 575
Ala Val Glu Arg Tyr Leu Gln Asp Gln Leu Leu Gly Ile Trp Gly
            580                 585                 590
Cys Ser Gly Lys Leu Ile Cys Thr Thr Val Pro Trp Asn Ala Ser
        595                 600                 605
Trp Ser Asn Lys Ser Leu Glu Lys Ile Trp Asn Asn Met Thr Trp Met
    610                 615                 620
Glu Trp Glu Lys Glu Ile Asp Asn Tyr Thr Asn Leu Ile Tyr Thr Leu
```

```
                       625                 630                 635                 640
Ile Glu Glu Ser Gln Asn Gln Gln Glu Lys Asn Glu Gln Glu Leu Leu
                    645                 650                 655

Glu Leu Gly Lys Trp Asp Ser Leu Trp Ser Trp Phe Asp Ile Ser Gln
                660                 665                 670

Trp Leu Trp Tyr Ile Lys Ile Phe Ile Met Ile Val Gly Gly Leu Val
            675                 680                 685

Gly Leu Arg Ile Val Phe Ala Val Leu Ser Ile Val Asn Arg Val Arg
        690                 695                 700

Gln Gly Tyr Ser Pro Leu Ser Phe Gln Thr Arg Phe Pro Ala Pro Arg
705                 710                 715                 720

Gly Pro Asp Arg Pro Glu Gly Ile Glu Glu Gly Gly Glu Arg Asp
                725                 730                 735

Arg Asp Arg Ser Asp Arg Leu Val Asn Gly Phe Leu Ala Leu Ile Trp
                740                 745                 750

Asn Asp Leu Gly Ser Leu Cys Leu Phe Ser Tyr His Arg Leu Arg Asp
                755                 760                 765

Leu Leu Leu Ile Ala Ala Arg Ile Val Glu Leu Leu Gly Arg Arg Gly
        770                 775                 780

Trp Glu Val Leu Lys Tyr Trp Trp Asn Leu Leu Gln Tyr Trp Ser Gln
785                 790                 795                 800

Glu Leu Lys Asn Ser Ala Val Ser Leu Leu Asn Ala Thr Ala Ile Ala
                805                 810                 815

Val Ala Glu Gly Thr Asp Arg Val Ile Glu Val Val Gln Arg Ala Gly
                820                 825                 830

Arg Ala Ile Leu His Ile Pro Arg Arg Ile Arg Gln Gly Ala Glu Arg
            835                 840                 845

Ala Leu Ile
    850

<210> SEQ ID NO 6
<211> LENGTH: 858
<212> TYPE: PRT
<213> ORGANISM: Human immunodeficiency virus type 1

<400> SEQUENCE: 6

Met Arg Val Lys Glu Thr Gln Met Asn Trp Pro Asn Leu Trp Lys Trp
1               5                  10                  15

Gly Thr Leu Ile Ile Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile Tyr Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Thr Cys Thr Asn Ala Thr Ala Lys Asn Ile Thr Asn Phe Ser Asn Ile
    130                 135                 140

Thr Gly Thr Ile Thr Asp Glu Val Arg Asn Cys Ser Phe Asn Met Thr
```

-continued

```
            145                 150                 155                 160
        Thr Glu Ile Arg Asp Lys Gln Gln Lys Val His Ala Leu Phe Tyr Lys
                            165                 170                 175

Leu Asp Leu Val Gln Met Glu Gly Ser Asn Ser Ser Lys Gly Ser Asn
                            180                 185                 190

Ser Ser Glu Tyr Arg Leu Ile Asn Cys Asn Thr Ser Val Ile Lys Gln
                            195                 200                 205

Ala Cys Pro Lys Ile Ser Phe Asp Pro Ile Pro Ile His Tyr Cys Thr
                            210                 215                 220

Pro Ala Gly Tyr Ala Met Leu Lys Cys Asn Asp Arg Asn Phe Asn Gly
        225                 230                 235                 240

Thr Gly Pro Cys Asn Asn Val Ser Ser Val Gln Cys Thr His Gly Ile
                            245                 250                 255

Lys Pro Val Val Ser Thr Gln Leu Leu Leu Asn Gly Ser Leu Ala Glu
                            260                 265                 270

Glu Glu Ile Ile Ile Arg Ser Glu Asn Leu Thr Asn Asn Ala Lys Thr
                            275                 280                 285

Ile Ile Val His Leu Asn Lys Ser Val Glu Ile Asn Cys Thr Arg Pro
                            290                 295                 300

Ser Asn Asn Ile Arg Arg Ser Ile Thr Ile Gly Pro Gly Gln Val Phe
        305                 310                 315                 320

Tyr Lys Thr Gly Ser Ile Met Gly Asp Ile Arg Lys Ala Tyr Cys Glu
                            325                 330                 335

Ile Asn Gly Thr Lys Trp Tyr Glu Ala Leu Lys Lys Val Lys Glu Arg
                            340                 345                 350

Leu Glu Glu His Phe Thr Asn Lys Thr Ile Thr Phe Gln Pro Pro Ser
                            355                 360                 365

Gly Gly Asp Leu Glu Ile Thr Met His His Phe Asn Cys Arg Gly Glu
                            370                 375                 380

Phe Phe Tyr Cys Asn Thr Thr Gln Leu Phe Asn Asn Thr Cys Ile Gly
        385                 390                 395                 400

Asn Lys Thr Cys Asn Ser Thr Ile Thr Leu Pro Cys Lys Ile Lys Gln
                            405                 410                 415

Ile Ile Asn Met Trp Gln Gly Val Gly Gln Ala Met Tyr Ala Pro Pro
                            420                 425                 430

Ile Ser Gly Lys Ile Asn Cys Val Ser Asn Ile Thr Gly Ile Leu Leu
                            435                 440                 445

Thr Arg Asp Gly Gly Ala Asn Asn Thr Asn Asp Glu Thr Phe Arg
        450                 455                 460

Pro Gly Gly Gly Asn Ile Lys Asp Asn Trp Arg Ser Glu Leu Tyr Lys
        465                 470                 475                 480

Tyr Lys Val Val Glu Ile Glu Pro Leu Gly Ile Ala Pro Thr Arg Ala
                            485                 490                 495

Lys Arg Arg Val Val Glu Arg Glu Lys Arg Ala Val Gly Ile Gly Ala
                            500                 505                 510

Met Ile Phe Gly Phe Leu Gly Ala Ala Gly Ser Thr Met Gly Ala Ala
                            515                 520                 525

Ser Ile Thr Leu Thr Val Gln Ala Arg Gln Leu Leu Ser Gly Ile Val
                            530                 535                 540

Gln Gln Gln Ser Asn Leu Leu Arg Ala Ile Glu Ala Gln His Met
        545                 550                 555                 560

Leu Gln Leu Thr Val Trp Gly Ile Lys Gln Leu Gln Ala Arg Val Leu
                            565                 570                 575
```

-continued

```
Ala Val Glu Arg Tyr Leu Lys Asp Gln Lys Phe Leu Gly Leu Trp Gly
            580                 585                 590

Cys Ser Gly Lys Thr Ile Cys Thr Thr Ala Val Pro Trp Asn Ser Thr
        595                 600                 605

Trp Ser Asn Lys Ser Phe Glu Glu Ile Trp Asn Asn Met Thr Trp Ile
    610                 615                 620

Glu Trp Glu Arg Glu Ile Ser Asn Tyr Thr Ser Gln Ile Phe Glu Ile
625                 630                 635                 640

Leu Thr Glu Ser Gln Asn Gln Gln Glu Arg Asn Glu Lys Asp Leu Leu
                645                 650                 655

Glu Leu Asp Lys Trp Ala Ser Leu Trp Asn Trp Phe Asp Ile Thr Lys
            660                 665                 670

Trp Leu Trp Tyr Ile Lys Ile Phe Ile Met Ile Val Gly Gly Leu Ile
        675                 680                 685

Gly Leu Arg Ile Ile Phe Ala Val Leu Ser Ile Val Asn Arg Val Arg
    690                 695                 700

Gln Gly Tyr Ser Pro Leu Ser Phe Gln Thr Pro Thr His His Gln Arg
705                 710                 715                 720

Glu Pro Asp Arg Pro Glu Arg Ile Glu Glu Gly Gly Glu Gln Gly
                725                 730                 735

Arg Asp Arg Ser Val Arg Leu Val Ser Gly Phe Leu Ala Leu Ala Trp
            740                 745                 750

Asp Asp Leu Arg Ser Leu Cys Leu Phe Ser Tyr His Arg Leu Arg Asp
        755                 760                 765

Phe Ile Leu Ile Ala Ala Arg Thr Val Glu Leu Leu Gly His Ser Ser
    770                 775                 780

Leu Lys Gly Leu Arg Arg Gly Trp Glu Gly Leu Lys Tyr Leu Gly Asn
785                 790                 795                 800

Leu Leu Val Tyr Trp Gly Gln Glu Leu Lys Ile Ser Ala Ile Ser Leu
                805                 810                 815

Leu Asp Ala Thr Ala Ile Ala Val Ala Gly Arg Thr Asp Arg Val Ile
            820                 825                 830

Glu Val Ala Gln Gly Ala Trp Arg Ala Ile Leu His Ile Pro Arg Arg
        835                 840                 845

Ile Arg Gln Gly Leu Glu Arg Ala Leu Leu
    850                 855

<210> SEQ ID NO 7
<211> LENGTH: 851
<212> TYPE: PRT
<213> ORGANISM: Human immunodeficiency virus type 1

<400> SEQUENCE: 7

Met Arg Val Lys Gly Ile Gln Lys Asn Trp Gln His Leu Trp Lys Trp
1               5                   10                  15

Gly Thr Leu Ile Leu Gly Leu Val Ile Val Cys Ser Ala Ser Asn Asn
            20                  25                  30

Leu Trp Val Thr Val Tyr Tyr Gly Val Pro Val Trp Glu Asp Ala Asp
        35                  40                  45

Thr Ile Leu Phe Cys Ala Ser Asp Ala Lys Ala Tyr Ser Thr Glu Lys
    50                  55                  60

His Asn Val Trp Ala Thr His Ala Cys Val Pro Thr Asp Pro Asn Pro
65                  70                  75                  80

Gln Glu Ile Thr Leu Glu Asn Val Thr Glu Lys Phe Asn Met Trp Asp
                85                  90                  95
```

-continued

```
Asn His Met Val Asp Gln Met Asn Glu Asp Ile Ile Ser Leu Trp Asp
            100                 105                 110

Glu Ser Leu Lys Pro Cys Val Lys Leu Thr Pro Leu Cys Val Thr Leu
            115                 120                 125

Ser Cys Thr Asn Val Thr Lys Asn Ser Thr Ala Asn Asn Gly Thr Val
        130                 135                 140

Asp Asp Lys Ile Gly Met Lys Asn Cys Ser Phe Asn Ile Thr Thr Glu
145                 150                 155                 160

Ile Arg Asp Lys Lys Lys Thr Glu Tyr Ala Leu Phe Tyr Lys Leu Asp
                165                 170                 175

Ile Glu Pro Ile Asp Lys Asn Asp Thr Thr Tyr Arg Leu Ile Asn Cys
            180                 185                 190

Asn Val Ser Thr Ile Lys Gln Ala Cys Pro Lys Val Thr Phe Glu Pro
        195                 200                 205

Ile Pro Ile His Tyr Cys Ala Pro Ala Gly Phe Ala Ile Leu Lys Cys
    210                 215                 220

Arg Asp Arg Asn Phe Asn Gly Thr Gly Leu Cys Lys Asn Val Ser Thr
225                 230                 235                 240

Val Gln Cys Thr His Gly Ile Lys Pro Val Val Ser Thr Gln Leu Leu
                245                 250                 255

Leu Asn Gly Ser Leu Ala Glu Gly Asp Val Met Ile Arg Ser Glu Asn
            260                 265                 270

Leu Thr Asp Asn Lys Lys Ile Ile Ile Val Gln Phe Asn Glu Ser Val
        275                 280                 285

Ser Ile Asn Cys Thr Arg Pro Asn Asn Asn Thr Arg Arg Ser Val His
    290                 295                 300

Ile Ala Pro Gly Gln Ala Phe Tyr Ala Thr Gly Asp Ile Ile Gly Asp
305                 310                 315                 320

Ile Arg Gln Ala His Cys Asn Val Ser Glu Ser Lys Trp Asn Glu Met
                325                 330                 335

Leu Gln Lys Val Ala Val Gln Leu Arg Gln His Phe Asn Lys Thr Ala
            340                 345                 350

Ile Lys Phe Thr Asn Ser Ser Gly Gly Asp Leu Glu Ile Thr Thr His
        355                 360                 365

Ser Phe Asn Cys Gly Gly Glu Phe Phe Tyr Cys Asn Thr Ser Gly Leu
    370                 375                 380

Phe Asn Ser Thr Trp Tyr Arg Asn Gly Thr Ala Ile Arg Gln Asn Gly
385                 390                 395                 400

Thr Gly Leu Asn Asp Thr Ile Thr Leu Pro Cys Arg Ile Arg Gln Ile
                405                 410                 415

Val Arg Thr Trp Gln Arg Val Gly Gln Ala Met Tyr Ala Pro Pro Ile
            420                 425                 430

Gln Gly Val Ile Lys Cys Glu Ser Asn Ile Thr Gly Leu Leu Leu Thr
        435                 440                 445

Arg Asp Gly Gly Asn Asn Ser Ser Asn Asn Asp Thr Glu Thr Phe Arg
    450                 455                 460

Pro Gly Gly Gly Asp Met Glu Asp Asn Trp Arg Ser Glu Leu Tyr Asn
465                 470                 475                 480

Tyr Lys Val Val Lys Ile Lys Pro Leu Gly Ile Ala Pro Thr Lys Ala
                485                 490                 495

Arg Arg Arg Val Val Gly Arg Glu Lys Arg Ala Val Gly Leu Gly Ala
            500                 505                 510

Val Phe Leu Gly Phe Leu Gly Thr Ala Gly Ser Thr Met Gly Ala Ala
        515                 520                 525
```

```
Ser Ile Thr Leu Thr Val Gln Val Arg Gln Leu Leu Ser Gly Ile Val
    530                 535                 540
His Gln Gln Ser Asn Leu Leu Arg Ala Ile Glu Ala Gln Gln His Leu
545                 550                 555                 560
Leu Gln Leu Thr Val Trp Gly Ile Lys Gln Leu Gln Ala Arg Val Leu
                565                 570                 575
Ala Leu Glu Arg Tyr Leu Lys Asp Gln Gln Leu Leu Gly Ile Trp Gly
            580                 585                 590
Cys Ser Gly Lys Leu Ile Cys Pro Thr Asn Val Pro Trp Asn Ala Ser
        595                 600                 605
Trp Ser Asn Lys Thr Phe Asn Glu Ile Trp Asp Asn Met Thr Trp Ile
610                 615                 620
Glu Trp Asp Arg Glu Ile Asn Asn Tyr Thr Gln Gln Ile Tyr Arg Leu
625                 630                 635                 640
Ile Glu Glu Ser Gln Gly Gln Gln Glu Lys Asn Glu Gln Asp Leu Leu
                645                 650                 655
Ala Leu Asp Lys Trp Ala Ser Leu Trp Asn Trp Phe Asp Ile Ser Asn
            660                 665                 670
Trp Leu Trp Tyr Ile Arg Ile Phe Ile Met Ile Val Gly Gly Leu Ile
        675                 680                 685
Gly Leu Arg Ile Val Phe Ala Val Leu Ser Ile Val Asn Arg Val Arg
690                 695                 700
Gln Gly Tyr Ser Pro Leu Ser Leu Gln Thr Leu Ile Pro Asn Pro Thr
705                 710                 715                 720
Gly Ala Asp Arg Pro Gly Glu Ile Glu Glu Gly Gly Gly Glu Gln Gly
                725                 730                 735
Arg Thr Arg Ser Ile Arg Leu Val Asp Arg Phe Leu Ala Leu Ala Trp
            740                 745                 750
Asp Asp Leu Arg Ser Leu Cys Leu Cys Ser Tyr His Arg Leu Arg Asp
        755                 760                 765
Phe Val Leu Ile Ala Ala Arg Thr Val Glu Thr Leu Gly Arg Arg Gly
770                 775                 780
Trp Glu Ile Leu Lys Tyr Leu Gly Asn Leu Val Trp Tyr Trp Gly Gln
785                 790                 795                 800
Glu Leu Lys Asn Ser Ala Ile Asn Leu Val Asp Thr Ile Ala Ile Ala
                805                 810                 815
Val Ala Asn Trp Thr Asp Arg Val Ile Glu Val Ile Gln Arg Val Val
            820                 825                 830
Arg Ala Phe Leu His Ile Pro Arg Arg Ile Arg Gln Gly Phe Glu Arg
        835                 840                 845
Ala Leu Leu
    850

<210> SEQ ID NO 8
<211> LENGTH: 6
<212> TYPE: PRT
<213> ORGANISM: Human immunodeficiency virus type 1

<400> SEQUENCE: 8

Asn Trp Phe Asp Ile Thr
1               5

<210> SEQ ID NO 9
<211> LENGTH: 53
<212> TYPE: DNA
<213> ORGANISM: Artificial Sequence
```

```
<220> FEATURE:
<223> OTHER INFORMATION: PCR primer for gp160

<400> SEQUENCE: 9
atggagccag tagatcctag actagagccc tggaagcatc caggaagtca gcc          53

<210> SEQ ID NO 10
<211> LENGTH: 42
<212> TYPE: DNA
<213> ORGANISM: Artificial Sequence
<220> FEATURE:
<223> OTHER INFORMATION: PCR primer for gp160

<400> SEQUENCE: 10
gtcattggtc ttaaaggtac ctgaggtctg tctggaaaac cc                      42

<210> SEQ ID NO 11
<211> LENGTH: 37
<212> TYPE: DNA
<213> ORGANISM: Artificial Sequence
<220> FEATURE:
<223> OTHER INFORMATION: PCR primer for gp160

<400> SEQUENCE: 11
aaaaggctta ggcatctcct atggcaggaa gaagcgg                            37

<210> SEQ ID NO 12
<211> LENGTH: 35
<212> TYPE: DNA
<213> ORGANISM: Artificial Sequence
<220> FEATURE:
<223> OTHER INFORMATION: PCR primer for gp160

<400> SEQUENCE: 12
ctcgagatac tgctcccacc ccatctgctg ctggc                              35

<210> SEQ ID NO 13
<211> LENGTH: 35
<212> TYPE: DNA
<213> ORGANISM: Artificial Sequence
<220> FEATURE:
<223> OTHER INFORMATION: PCR primer for gp160

<400> SEQUENCE: 13
ataagagaaa gagcagaaga cagtggcaat gagag                              35

<210> SEQ ID NO 14
<211> LENGTH: 35
<212> TYPE: DNA
<213> ORGANISM: Artificial Sequence
<220> FEATURE:
<223> OTHER INFORMATION: PCR primer for gp160

<400> SEQUENCE: 14
gtcattggtc ttaaaggtac ctgaggtctg actgg                              35

<210> SEQ ID NO 15
<211> LENGTH: 4
<212> TYPE: PRT
<213> ORGANISM: Human immunodeficiency virus type 1

<400> SEQUENCE: 15

Asp Lys Trp Ala
1

<210> SEQ ID NO 16
```

```
<211> LENGTH: 4
<212> TYPE: PRT
<213> ORGANISM: Human immunodeficiency virus type 1

<400> SEQUENCE: 16

Gly Lys Trp Asp
1

<210> SEQ ID NO 17
<211> LENGTH: 7
<212> TYPE: PRT
<213> ORGANISM: Human immunodeficiency virus type 1

<400> SEQUENCE: 17

Thr Leu Asp Lys Trp Ala Ser
1               5

<210> SEQ ID NO 18
<211> LENGTH: 20
<212> TYPE: PRT
<213> ORGANISM: Human immunodeficiency virus type 1

<400> SEQUENCE: 18

Glu Gln Asp Leu Leu Ala Leu Asp Lys Trp Ala Ser Leu Trp Asn Trp
1               5                   10                  15

Phe Asp Ile Ser
            20

<210> SEQ ID NO 19
<211> LENGTH: 20
<212> TYPE: PRT
<213> ORGANISM: Human immunodeficiency virus type 1

<400> SEQUENCE: 19

Glu Gln Asp Leu Leu Ala Leu Asp Lys Trp Ala Ser Leu Trp Asn Trp
1               5                   10                  15

Phe Asn Ile Ser
            20

<210> SEQ ID NO 20
<211> LENGTH: 20
<212> TYPE: PRT
<213> ORGANISM: Human immunodeficiency virus type 1

<400> SEQUENCE: 20

Glu Gln Asp Leu Leu Ala Leu Asp Thr Trp Ala Ser Leu Trp Asn Trp
1               5                   10                  15

Phe Asn Ile Ser
            20

<210> SEQ ID NO 21
<211> LENGTH: 20
<212> TYPE: PRT
<213> ORGANISM: Human immunodeficiency virus type 1

<400> SEQUENCE: 21

Glu Gln Glu Leu Leu Glu Leu Asp Lys Trp Ala Ser Leu Trp Asn Trp
1               5                   10                  15

Phe Asp Ile Thr
            20

<210> SEQ ID NO 22
<211> LENGTH: 20
<212> TYPE: PRT
```

<213> ORGANISM: Human immunodeficiency virus type 1

<400> SEQUENCE: 22

Glu Gln Glu Leu Leu Glu Leu Gly Lys Trp Asp Ser Leu Trp Ser Trp
1               5                   10                  15

Phe Asp Ile Ser
            20

<210> SEQ ID NO 23
<211> LENGTH: 20
<212> TYPE: PRT
<213> ORGANISM: Human immunodeficiency virus type 1

<400> SEQUENCE: 23

Glu Gln Glu Leu Leu Glu Leu Asp Lys Trp Ala Asn Leu Trp Asn Trp
1               5                   10                  15

Phe Asp Ile Ser
            20

<210> SEQ ID NO 24
<211> LENGTH: 20
<212> TYPE: PRT
<213> ORGANISM: Human immunodeficiency virus type 1

<400> SEQUENCE: 24

Glu Lys Asp Leu Leu Gly Leu Asp Lys Trp Ala Ser Leu Trp Asn Trp
1               5                   10                  15

Phe Asp Ile Thr
            20

<210> SEQ ID NO 25
<211> LENGTH: 20
<212> TYPE: PRT
<213> ORGANISM: Human immunodeficiency virus type 1

<400> SEQUENCE: 25

Glu Gln Glu Leu Leu Thr Leu Asp Lys Trp Ala Ser Leu Trp Asn Trp
1               5                   10                  15

Phe Asp Ile Ser
            20

<210> SEQ ID NO 26
<211> LENGTH: 20
<212> TYPE: PRT
<213> ORGANISM: Human immunodeficiency virus type 1

<400> SEQUENCE: 26

Glu Gln Asp Leu Leu Ala Leu Asp Lys Trp Ala Gly Leu Trp Asn Trp
1               5                   10                  15

Phe Asp Ile Ser
            20

<210> SEQ ID NO 27
<211> LENGTH: 20
<212> TYPE: PRT
<213> ORGANISM: Human immunodeficiency virus type 1

<400> SEQUENCE: 27

Glu Gln Asp Leu Leu Ala Leu Asp Lys Trp Ala Ser Leu Trp Asn Trp
1               5                   10                  15

Phe Asp Ile Thr
            20

```
<210> SEQ ID NO 28
<211> LENGTH: 20
<212> TYPE: PRT
<213> ORGANISM: Human immunodeficiency virus type 1

<400> SEQUENCE: 28

Glu Gln Glu Leu Leu Ser Leu Asp Lys Trp Ala Ser Leu Trp Ser Trp
1               5                   10                  15

Phe Glu Ile Ser
            20

<210> SEQ ID NO 29
<211> LENGTH: 20
<212> TYPE: PRT
<213> ORGANISM: Human immunodeficiency virus type 1

<400> SEQUENCE: 29

Glu Gln Glu Leu Leu Glu Leu Asp Lys Trp Ala Ser Leu Trp Asn Trp
1               5                   10                  15

Phe Asp Ile Thr
            20

<210> SEQ ID NO 30
<211> LENGTH: 20
<212> TYPE: PRT
<213> ORGANISM: Human immunodeficiency virus type 1

<400> SEQUENCE: 30

Glu Gln Glu Leu Leu Glu Leu Asp Lys Trp Ala Ser Leu Trp Asn Trp
1               5                   10                  15

Phe Ser Ile Thr
            20

<210> SEQ ID NO 31
<211> LENGTH: 20
<212> TYPE: PRT
<213> ORGANISM: Human immunodeficiency virus type 1

<400> SEQUENCE: 31

Glu Gln Glu Leu Leu Ala Leu Asp Lys Trp Ala Ser Leu Trp Asn Trp
1               5                   10                  15

Phe Asp Ile Ser
            20

<210> SEQ ID NO 32
<211> LENGTH: 20
<212> TYPE: PRT
<213> ORGANISM: Human immunodeficiency virus type 1

<400> SEQUENCE: 32

Glu Lys Asp Leu Leu Glu Leu Asp Lys Trp Ala Ser Leu Trp Asn Trp
1               5                   10                  15

Phe Asp Ile Thr
            20

<210> SEQ ID NO 33
<211> LENGTH: 13
<212> TYPE: PRT
<213> ORGANISM: Human immunodeficiency virus type 1

<400> SEQUENCE: 33

Asp Leu Leu Ala Leu Asp Lys Trp Ala Ser Leu Trp Asn
1               5                   10
```

```
<210> SEQ ID NO 34
<211> LENGTH: 13
<212> TYPE: PRT
<213> ORGANISM: Human immunodeficiency virus type 1

<400> SEQUENCE: 34

Asp Leu Leu Ala Leu Asp Lys Trp Glu Ser Leu Trp Asn
1               5                   10

<210> SEQ ID NO 35
<211> LENGTH: 13
<212> TYPE: PRT
<213> ORGANISM: Human immunodeficiency virus type 1

<400> SEQUENCE: 35

Asp Leu Leu Ala Leu Asp Thr Trp Ala Ser Leu Trp Asn
1               5                   10

<210> SEQ ID NO 36
<211> LENGTH: 13
<212> TYPE: PRT
<213> ORGANISM: Human immunodeficiency virus type 1

<400> SEQUENCE: 36

Asp Leu Leu Ala Leu Asp Lys Trp Ala Gly Leu Trp Asn
1               5                   10

<210> SEQ ID NO 37
<211> LENGTH: 13
<212> TYPE: PRT
<213> ORGANISM: Human immunodeficiency virus type 1

<400> SEQUENCE: 37

Asp Leu Leu Ala Leu Asp Lys Trp Glu Asn Leu Trp Asn
1               5                   10

<210> SEQ ID NO 38
<211> LENGTH: 13
<212> TYPE: PRT
<213> ORGANISM: Human immunodeficiency virus type 1

<400> SEQUENCE: 38

Glu Leu Leu Thr Leu Asp Lys Trp Ala Ser Leu Trp Asn
1               5                   10

<210> SEQ ID NO 39
<211> LENGTH: 13
<212> TYPE: PRT
<213> ORGANISM: Human immunodeficiency virus type 1

<400> SEQUENCE: 39

Glu Leu Leu Thr Leu Asp Lys Trp Ala Gly Leu Trp Asn
1               5                   10

<210> SEQ ID NO 40
<211> LENGTH: 13
<212> TYPE: PRT
<213> ORGANISM: Human immunodeficiency virus type 1

<400> SEQUENCE: 40

Glu Leu Leu Ala Leu Asp Lys Trp Ala Ser Leu Trp Asn
1               5                   10

<210> SEQ ID NO 41
```

```
<211> LENGTH: 866
<212> TYPE: PRT
<213> ORGANISM: Human immunodeficiency virus type 1

<400> SEQUENCE: 41
```

| | | | | | | | | | | | | | | |
|---|---|---|---|---|---|---|---|---|---|---|---|---|---|---|
| Met | Arg | Val | Lys | Gly | Ile | Arg | Arg | Asn | Tyr | Gln | His | Trp | Trp | Gly | Trp |
| 1 | | | | 5 | | | | | 10 | | | | | 15 | |

| Gly | Thr | Met | Leu | Leu | Gly | Leu | Leu | Met | Ile | Cys | Ser | Ala | Thr | Glu | Lys |
|---|---|---|---|---|---|---|---|---|---|---|---|---|---|---|---|
| | | | 20 | | | | | 25 | | | | | 30 | | |

| Leu | Trp | Val | Thr | Val | Tyr | Tyr | Gly | Val | Pro | Val | Trp | Lys | Glu | Ala | Thr |
|---|---|---|---|---|---|---|---|---|---|---|---|---|---|---|---|
| | | | 35 | | | | | 40 | | | | | 45 | | |

| Thr | Thr | Leu | Phe | Cys | Ala | Ser | Asp | Ala | Lys | Ala | Tyr | Asp | Thr | Glu | Ala |
|---|---|---|---|---|---|---|---|---|---|---|---|---|---|---|---|
| | 50 | | | | | 55 | | | | | 60 | | | | |

| His | Asn | Val | Trp | Ala | Thr | His | Ala | Cys | Val | Pro | Thr | Asp | Pro | Asn | Pro |
|---|---|---|---|---|---|---|---|---|---|---|---|---|---|---|---|
| 65 | | | | | 70 | | | | | 75 | | | | | 80 |

| Gln | Glu | Val | Glu | Leu | Val | Asn | Val | Thr | Glu | Asn | Phe | Asn | Met | Trp | Lys |
|---|---|---|---|---|---|---|---|---|---|---|---|---|---|---|---|
| | | | | 85 | | | | | 90 | | | | | 95 | |

| Asn | Asn | Met | Val | Glu | Gln | Met | His | Glu | Asp | Ile | Ile | Ser | Leu | Trp | Asp |
|---|---|---|---|---|---|---|---|---|---|---|---|---|---|---|---|
| | | | 100 | | | | | 105 | | | | | 110 | | |

| Gln | Ser | Leu | Lys | Pro | Cys | Val | Lys | Leu | Thr | Pro | Leu | Cys | Val | Thr | Leu |
|---|---|---|---|---|---|---|---|---|---|---|---|---|---|---|---|
| | | | 115 | | | | | 120 | | | | | 125 | | |

| Asn | Cys | Thr | Asp | Leu | Arg | Asn | Thr | Thr | Asn | Thr | Asn | Asn | Ser | Thr | Asp |
|---|---|---|---|---|---|---|---|---|---|---|---|---|---|---|---|
| | 130 | | | | | 135 | | | | | 140 | | | | |

| Asn | Asn | Asn | Ser | Asn | Ser | Glu | Gly | Thr | Ile | Lys | Gly | Gly | Glu | Met | Lys |
|---|---|---|---|---|---|---|---|---|---|---|---|---|---|---|---|
| 145 | | | | | 150 | | | | | 155 | | | | | 160 |

| Asn | Cys | Ser | Phe | Asn | Ile | Ala | Thr | Ser | Ile | Gly | Asp | Lys | Met | Gln | Lys |
|---|---|---|---|---|---|---|---|---|---|---|---|---|---|---|---|
| | | | | 165 | | | | | 170 | | | | | 175 | |

| Glu | Tyr | Ala | Leu | Leu | Tyr | Lys | Leu | Asp | Ile | Glu | Pro | Ile | Asp | Asn | Asp |
|---|---|---|---|---|---|---|---|---|---|---|---|---|---|---|---|
| | | | 180 | | | | | 185 | | | | | 190 | | |

| Asn | Thr | Ser | Tyr | Arg | Leu | Ile | Ser | Cys | Asn | Thr | Ser | Val | Ile | Thr | Gln |
|---|---|---|---|---|---|---|---|---|---|---|---|---|---|---|---|
| | | | 195 | | | | | 200 | | | | | 205 | | |

| Ala | Cys | Pro | Lys | Ile | Ser | Phe | Glu | Pro | Ile | Pro | Ile | His | Tyr | Cys | Ala |
|---|---|---|---|---|---|---|---|---|---|---|---|---|---|---|---|
| | 210 | | | | | 215 | | | | | 220 | | | | |

| Pro | Ala | Gly | Phe | Ala | Ile | Leu | Lys | Cys | Asn | Asp | Lys | Lys | Phe | Ser | Gly |
|---|---|---|---|---|---|---|---|---|---|---|---|---|---|---|---|
| 225 | | | | | 230 | | | | | 235 | | | | | 240 |

| Lys | Gly | Ser | Cys | Lys | Asn | Val | Ser | Thr | Val | Gln | Cys | Thr | His | Gly | Ile |
|---|---|---|---|---|---|---|---|---|---|---|---|---|---|---|---|
| | | | | 245 | | | | | 250 | | | | | 255 | |

| Arg | Pro | Val | Val | Ser | Thr | Gln | Leu | Leu | Leu | Asn | Gly | Ser | Leu | Ala | Glu |
|---|---|---|---|---|---|---|---|---|---|---|---|---|---|---|---|
| | | | 260 | | | | | 265 | | | | | 270 | | |

| Glu | Glu | Val | Val | Ile | Arg | Ser | Glu | Asn | Phe | Thr | Asn | Asn | Ala | Lys | Thr |
|---|---|---|---|---|---|---|---|---|---|---|---|---|---|---|---|
| | | | 275 | | | | | 280 | | | | | 285 | | |

| Ile | Ile | Val | Gln | Leu | Arg | Glu | Pro | Val | Lys | Ile | Asn | Cys | Ser | Arg | Pro |
|---|---|---|---|---|---|---|---|---|---|---|---|---|---|---|---|
| | 290 | | | | | 295 | | | | | 300 | | | | |

| Asn | Asn | Asn | Thr | Arg | Lys | Ser | Ile | Pro | Met | Gly | Pro | Gly | Arg | Ala | Phe |
|---|---|---|---|---|---|---|---|---|---|---|---|---|---|---|---|
| 305 | | | | | 310 | | | | | 315 | | | | | 320 |

| Tyr | Thr | Thr | Gly | Gln | Ile | Ile | Gly | Asp | Ile | Arg | Gln | Ala | His | Cys | Asn |
|---|---|---|---|---|---|---|---|---|---|---|---|---|---|---|---|
| | | | | 325 | | | | | 330 | | | | | 335 | |

| Ile | Ser | Lys | Thr | Asn | Trp | Thr | Asn | Ala | Leu | Lys | Gln | Val | Val | Glu | Lys |
|---|---|---|---|---|---|---|---|---|---|---|---|---|---|---|---|
| | | | 340 | | | | | 345 | | | | | 350 | | |

| Leu | Gly | Glu | Gln | Phe | Asn | Lys | Thr | Lys | Ile | Val | Phe | Thr | Asn | Ser | Ser |
|---|---|---|---|---|---|---|---|---|---|---|---|---|---|---|---|
| | | | 355 | | | | | 360 | | | | | 365 | | |

| Gly | Gly | Asp | Pro | Glu | Ile | Val | Thr | His | Ser | Phe | Asn | Cys | Ala | Gly | Glu |
|---|---|---|---|---|---|---|---|---|---|---|---|---|---|---|---|
| | 370 | | | | | 375 | | | | | 380 | | | | |

| Phe | Phe | Tyr | Cys | Asn | Thr | Thr | Gln | Leu | Phe | Asp | Ser | Ile | Trp | Asn | Ser |
|---|---|---|---|---|---|---|---|---|---|---|---|---|---|---|---|
| 385 | | | | | 390 | | | | | 395 | | | | | 400 |

```
Glu Asn Gly Thr Trp Asn Ile Thr Arg Gly Leu Asn Asn Thr Gly Arg
                405                 410                 415
Asn Asp Thr Ile Thr Leu Pro Cys Arg Ile Lys Gln Ile Ile Asn Arg
            420                 425                 430
Trp Gln Glu Val Gly Lys Ala Met Tyr Ala Pro Pro Ile Lys Gly Asn
        435                 440                 445
Ile Ser Cys Ser Ser Asn Ile Thr Gly Leu Leu Leu Thr Arg Asp Gly
450                 455                 460
Gly Lys Asp Asp Asn Ser Arg Asp Gly Asn Glu Thr Phe Arg Pro Gly
465                 470                 475                 480
Gly Gly Asp Met Arg Asp Asn Trp Arg Ser Glu Leu Tyr Lys Tyr Lys
                485                 490                 495
Val Val Lys Ile Glu Pro Leu Gly Val Ala Pro Thr Lys Ala Lys Arg
            500                 505                 510
Arg Val Val Gln Arg Glu Glu Arg Ala Val Gly Leu Gly Ala Met Phe
        515                 520                 525
Phe Gly Phe Leu Gly Ala Ala Gly Ser Thr Met Gly Ala Ala Ser Val
530                 535                 540
Thr Leu Thr Val Gln Ala Arg Gln Leu Leu Ser Gly Ile Val Gln Gln
545                 550                 555                 560
Gln Ser Asn Leu Leu Arg Ala Ile Glu Ala Gln Gln His Leu Leu Gln
                565                 570                 575
Leu Thr Val Trp Gly Ile Lys Gln Leu Gln Ala Arg Ile Leu Ala Val
            580                 585                 590
Glu Arg Tyr Leu Lys Asp Gln Gln Leu Leu Gly Ile Trp Gly Cys Ser
        595                 600                 605
Gly Lys Leu Ile Cys Thr Thr Thr Val Pro Trp Asn Ala Ser Trp Ser
610                 615                 620
Lys Asn Lys Thr Leu Glu Ala Ile Trp Asn Asn Met Thr Trp Met Gln
625                 630                 635                 640
Trp Asp Lys Glu Ile Asp Asn Tyr Thr Ser Leu Ile Tyr Ser Leu Ile
                645                 650                 655
Glu Glu Ser Pro Ile Gln Gln Glu Lys Asn Glu Gln Glu Leu Leu Glu
            660                 665                 670
Leu Asp Lys Trp Ala Asn Leu Trp Asn Trp Phe Asp Ile Ser Asn Trp
        675                 680                 685
Leu Trp Tyr Ile Lys Ile Phe Ile Met Ile Val Gly Gly Leu Val Gly
690                 695                 700
Leu Arg Ile Val Phe Val Val Leu Ser Ile Val Asn Arg Val Arg Gln
705                 710                 715                 720
Gly Tyr Ser Pro Leu Ser Phe Gln Thr Arg Leu Pro Ala Pro Arg Gly
                725                 730                 735
Pro Asp Arg Pro Glu Glu Ile Glu Glu Glu Gly Gly Asp Arg Asp Arg
            740                 745                 750
Asp Arg Ser Gly Leu Leu Val Asp Gly Phe Leu Thr Leu Ile Trp Val
        755                 760                 765
Asp Leu Arg Ser Leu Cys Leu Phe Ser Tyr His Arg Leu Arg Asp Leu
770                 775                 780
Leu Leu Ile Val Thr Arg Ile Val Glu Leu Leu Gly Arg Arg Gly Trp
785                 790                 795                 800
Glu Ile Leu Lys Tyr Trp Trp Asn Leu Leu Gln Tyr Trp Ser Gln Glu
                805                 810                 815
Leu Lys Asn Ser Ala Val Ser Leu Phe Asn Ala Thr Ala Ile Ala Val
```

```
                      820             825                 830
Ala Glu Gly Thr Asp Arg Val Ile Gln Val Leu Gln Arg Val Gly Arg
        835                 840                 845

Ala Leu Leu His Ile Pro Thr Arg Ile Arg Gln Gly Leu Glu Arg Ala
    850                 855                 860

Leu Leu
865

<210> SEQ ID NO 42
<211> LENGTH: 2622
<212> TYPE: DNA
<213> ORGANISM: Human immunodeficiency virus type 1
<220> FEATURE:
<221> NAME/KEY: CDS
<222> LOCATION: (1)..(2622)

<400> SEQUENCE: 42 atg aga gtg gtg ggg ata cag agg aat tat cca ctc cta tgg aga tgg      48
Met Arg Val Val Gly Ile Gln Arg Asn Tyr Pro Leu Leu Trp Arg Trp
1               5                   10                  15 ggt atg aca ata ttt tgg ata atg atg att tgt aat gct gaa aat ttg      96
Gly Met Thr Ile Phe Trp Ile Met Met Ile Cys Asn Ala Glu Asn Leu
                20                  25                  30 tgg gtc acg gtc tat tat ggg gta cct gtg tgg aaa gaa gca aag acc     144
Trp Val Thr Val Tyr Tyr Gly Val Pro Val Trp Lys Glu Ala Lys Thr
            35                  40                  45 acc cta ttt tgt gca tca gat gct aaa gca tat gat aca gaa gta cat     192
Thr Leu Phe Cys Ala Ser Asp Ala Lys Ala Tyr Asp Thr Glu Val His
        50                  55                  60 aat gtt tgg gct aca cat gcc tgt gta ccc aca gac cct aac cca caa     240
Asn Val Trp Ala Thr His Ala Cys Val Pro Thr Asp Pro Asn Pro Gln
65                  70                  75                  80 gaa ata cat ttg gca aat gta aca gaa aat ttt aac atg tgg aaa aat     288
Glu Ile His Leu Ala Asn Val Thr Glu Asn Phe Asn Met Trp Lys Asn
                85                  90                  95 acc atg gta gag cag atg cat gaa gat ata att agc cta tgg gac caa     336
Thr Met Val Glu Gln Met His Glu Asp Ile Ile Ser Leu Trp Asp Gln
                100                 105                 110 agc cta aag cca tgt gta cag tta acc cct ctc tgc gtt act tta aat     384
Ser Leu Lys Pro Cys Val Gln Leu Thr Pro Leu Cys Val Thr Leu Asn
            115                 120                 125 tgt cgt aac tac act aac aac agc acc ata tcc tct aac aac aat acc     432
Cys Arg Asn Tyr Thr Asn Asn Ser Thr Ile Ser Ser Asn Asn Asn Thr
        130                 135                 140 atc aac agt acc gta tct cct aac agc agt acc ata tct agt gac atg     480
Ile Asn Ser Thr Val Ser Pro Asn Ser Ser Thr Ile Ser Ser Asp Met
145                 150                 155                 160 caa gag gtg aaa aac tgc tct ttc aat atg acc aca gaa cta aga gat     528
Gln Glu Val Lys Asn Cys Ser Phe Asn Met Thr Thr Glu Leu Arg Asp
                165                 170                 175 aaa aaa cgg aaa gtg tat gca ctt ttt tat aga ctt gat ata gtg cca     576
Lys Lys Arg Lys Val Tyr Ala Leu Phe Tyr Arg Leu Asp Ile Val Pro
                180                 185                 190 ctc agt aat gat agt gat gag tat agg tta ata aat tgt aat acc tca     624
Leu Ser Asn Asp Ser Asp Glu Tyr Arg Leu Ile Asn Cys Asn Thr Ser
            195                 200                 205 gcc att aca cag gct tgt cca aag gta tcc ttt gat cca att ccc ata     672
Ala Ile Thr Gln Ala Cys Pro Lys Val Ser Phe Asp Pro Ile Pro Ile
        210                 215                 220 cat tat tgt gct cca gct ggt ttt gca att cta aag tgt aag gat aag     720
His Tyr Cys Ala Pro Ala Gly Phe Ala Ile Leu Lys Cys Lys Asp Lys
```

```
                    225                 230                 235                 240 aag ttc aat gga aca ggg cca tgc aat aat gtc agc aca gta caa tgc        768
Lys Phe Asn Gly Thr Gly Pro Cys Asn Asn Val Ser Thr Val Gln Cys
                245                 250                 255 aca cat gga atc aag cca gta gta tca act caa ctg ctg tta aat ggc        816
Thr His Gly Ile Lys Pro Val Val Ser Thr Gln Leu Leu Leu Asn Gly
                260                 265                 270 agt cta gca gaa gaa gag ata gtg atc aga tct gaa gat atc tca aac        864
Ser Leu Ala Glu Glu Glu Ile Val Ile Arg Ser Glu Asp Ile Ser Asn
            275                 280                 285 aat gcc aaa acc ata ata gta cag ttg gtt aac cct gta aga att aat        912
Asn Ala Lys Thr Ile Ile Val Gln Leu Val Asn Pro Val Arg Ile Asn
        290                 295                 300 tgt acc aga cca ggc aac aat aca agg aaa agt gta cgt ata gga cca        960
Cys Thr Arg Pro Gly Asn Asn Thr Arg Lys Ser Val Arg Ile Gly Pro
305                 310                 315                 320 ggg caa aca ttc tat gca aat gag ata ata ggg aat ata aga caa gca       1008
Gly Gln Thr Phe Tyr Ala Asn Glu Ile Ile Gly Asn Ile Arg Gln Ala
                325                 330                 335 cat tgt aat gtc agt aga tca gaa tgg aat aga act tta caa cag gta       1056
His Cys Asn Val Ser Arg Ser Glu Trp Asn Arg Thr Leu Gln Gln Val
                340                 345                 350 gct gta caa tta agg aag ctc tgg aat aaa aca ata atc ttt aat aaa       1104
Ala Val Gln Leu Arg Lys Leu Trp Asn Lys Thr Ile Ile Phe Asn Lys
            355                 360                 365 act tca gga ggg gat gta gaa att aca aca cat agt ttt aat tgt aga       1152
Thr Ser Gly Gly Asp Val Glu Ile Thr Thr His Ser Phe Asn Cys Arg
        370                 375                 380 gga gaa ttt ttc tat tgc aat aca tct aga ctg ttt aat agc act tgg       1200
Gly Glu Phe Phe Tyr Cys Asn Thr Ser Arg Leu Phe Asn Ser Thr Trp
385                 390                 395                 400 gat ggc aat aac acc agg gag gac aat agc act tgg ggt aac aat agc       1248
Asp Gly Asn Asn Thr Arg Glu Asp Asn Ser Thr Trp Gly Asn Asn Ser
                405                 410                 415 tca aat gac att ata act ctc caa tgc aaa ata aag caa att gta aat       1296
Ser Asn Asp Ile Ile Thr Leu Gln Cys Lys Ile Lys Gln Ile Val Asn
                420                 425                 430 atg tgg cag aga gta gga caa gca atg tat gcc ccc ccc atc cca gga       1344
Met Trp Gln Arg Val Gly Gln Ala Met Tyr Ala Pro Pro Ile Pro Gly
            435                 440                 445 gaa tta agg tgt gaa tca aac att aca gga tta cta tta aca aga gat       1392
Glu Leu Arg Cys Glu Ser Asn Ile Thr Gly Leu Leu Leu Thr Arg Asp
        450                 455                 460 gga ggg gga gag aat aag gat cgt cta aat gag acc ttc agg cct gga       1440
Gly Gly Gly Glu Asn Lys Asp Arg Leu Asn Glu Thr Phe Arg Pro Gly
465                 470                 475                 480 gga gga gac atg agg gac aat tgg aga agt gaa tta tat aag tat aag       1488
Gly Gly Asp Met Arg Asp Asn Trp Arg Ser Glu Leu Tyr Lys Tyr Lys
                485                 490                 495 gta gta aaa att gaa cca cta ggt gta gca ccc acc cat gca aaa aga       1536
Val Val Lys Ile Glu Pro Leu Gly Val Ala Pro Thr His Ala Lys Arg
                500                 505                 510 aga gtg gtg cag aga gaa aaa aga gca gtt gga ctg gga gct gtc ttc       1584
Arg Val Val Gln Arg Glu Lys Arg Ala Val Gly Leu Gly Ala Val Phe
            515                 520                 525 ctt ggg ttc tta gga gca gca gga agc act atg ggc gcg gcg tca ata       1632
Leu Gly Phe Leu Gly Ala Ala Gly Ser Thr Met Gly Ala Ala Ser Ile
        530                 535                 540 acg ctg acg gta cag gcc aga caa tta ttg tct ggt ata gtg caa cag       1680
Thr Leu Thr Val Gln Ala Arg Gln Leu Leu Ser Gly Ile Val Gln Gln
```

```
                        -continued
545              550              555              560 cag agt aat ttg ctg agg gct ata gag gct caa caa cat ttg ttg aaa    1728
Gln Ser Asn Leu Leu Arg Ala Ile Glu Ala Gln Gln His Leu Leu Lys
            565              570              575 ctc acg gtc tgg ggc att aaa cag ctc cag gca aga gtc ctg gct ctg    1776
Leu Thr Val Trp Gly Ile Lys Gln Leu Gln Ala Arg Val Leu Ala Leu
        580              585              590 gaa aga tac cta agg gat caa cag ctc cta gga att tgg ggc tgc tct    1824
Glu Arg Tyr Leu Arg Asp Gln Gln Leu Leu Gly Ile Trp Gly Cys Ser
    595              600              605 gga aaa ctc atc tgc acc act act gta ccc tgg aac tct agt tgg agt    1872
Gly Lys Leu Ile Cys Thr Thr Thr Val Pro Trp Asn Ser Ser Trp Ser
610              615              620 aat aaa act tat aag gaa ata tgg gat aac atg acc tgg ctg gaa tgg    1920
Asn Lys Thr Tyr Lys Glu Ile Trp Asp Asn Met Thr Trp Leu Glu Trp
625              630              635              640 gat aaa gaa att agc agg tac aca aac gta ata tat gac cta att gaa    1968
Asp Lys Glu Ile Ser Arg Tyr Thr Asn Val Ile Tyr Asp Leu Ile Glu
            645              650              655 gaa tcg cag aac cag cag gaa aag aat gaa caa gac tta tta gca ttg    2016
Glu Ser Gln Asn Gln Gln Glu Lys Asn Glu Gln Asp Leu Leu Ala Leu
        660              665              670 gac aca tgg gca agt ctg tgg aat tgg ttt aac ata tca aat tgg cta    2064
Asp Thr Trp Ala Ser Leu Trp Asn Trp Phe Asn Ile Ser Asn Trp Leu
    675              680              685 tgg tat ata aga ctc ttt ata atg ata gta gga ggt ttg ata ggt tta    2112
Trp Tyr Ile Arg Leu Phe Ile Met Ile Val Gly Gly Leu Ile Gly Leu
690              695              700 aga ata gtt ttt gct gtg ctt gct ata ata aat aga gtt agg cag gga    2160
Arg Ile Val Phe Ala Val Leu Ala Ile Ile Asn Arg Val Arg Gln Gly
705              710              715              720 tac tca cct ttg tct ttc cag acc ctt acc cac caa cag agg gaa caa    2208
Tyr Ser Pro Leu Ser Phe Gln Thr Leu Thr His Gln Gln Arg Glu Gln
            725              730              735 ccc gac aga ccc gaa aga atc gaa gaa gga ggt gga gag caa gac aga    2256
Pro Asp Arg Pro Glu Arg Ile Glu Glu Gly Gly Gly Glu Gln Asp Arg
        740              745              750 gac aga tcc gtg cga tta gtg agc ggg ttc tta gca ctt gcc tgg gac    2304
Asp Arg Ser Val Arg Leu Val Ser Gly Phe Leu Ala Leu Ala Trp Asp
    755              760              765 gat ctg cgg agc ctg tgc ctc ttc agc tac cac cga ttg aga gac ttt    2352
Asp Leu Arg Ser Leu Cys Leu Phe Ser Tyr His Arg Leu Arg Asp Phe
770              775              780 ctc ttg att gta atc agg act gtg gaa ctt ctg gca cac agc agt ctc    2400
Leu Leu Ile Val Ile Arg Thr Val Glu Leu Leu Ala His Ser Ser Leu
785              790              795              800 aag gga ctg aga ctg ggg tgg gaa gcc ctc aaa tat ctg tgg agc ctt    2448
Lys Gly Leu Arg Leu Gly Trp Glu Ala Leu Lys Tyr Leu Trp Ser Leu
            805              810              815 ctg tca tac tgg ggt cag gaa cta aag aat agt gct att agt ttg ctc    2496
Leu Ser Tyr Trp Gly Gln Glu Leu Lys Asn Ser Ala Ile Ser Leu Leu
        820              825              830 gat aca aca gca ata gca gta gct aac tgg aca gac agg gtt ata gaa    2544
Asp Thr Thr Ala Ile Ala Val Ala Asn Trp Thr Asp Arg Val Ile Glu
    835              840              845 ata gga caa aga att ggt aga gct att tgg aac ata cct aga aga att    2592
Ile Gly Gln Arg Ile Gly Arg Ala Ile Trp Asn Ile Pro Arg Arg Ile
850              855              860 aga cag ggt gtc gaa agg gct ttg cta taa                            2622
Arg Gln Gly Val Glu Arg Ala Leu Leu
```

<210> SEQ ID NO 43
<211> LENGTH: 873
<212> TYPE: PRT
<213> ORGANISM: Human immunodeficiency virus type 1

<400> SEQUENCE: 43

```
Met Arg Val Val Gly Ile Gln Arg Asn Tyr Pro Leu Leu Trp Arg Trp
  1               5                  10                  15
Gly Met Thr Ile Phe Trp Ile Met Met Ile Cys Asn Ala Glu Asn Leu
             20                  25                  30
Trp Val Thr Val Tyr Tyr Gly Val Pro Val Trp Lys Glu Ala Lys Thr
         35                  40                  45
Thr Leu Phe Cys Ala Ser Asp Ala Lys Ala Tyr Asp Thr Glu Val His
     50                  55                  60
Asn Val Trp Ala Thr His Ala Cys Val Pro Thr Asp Pro Asn Pro Gln
 65                  70                  75                  80
Glu Ile His Leu Ala Asn Val Thr Glu Asn Phe Asn Met Trp Lys Asn
                 85                  90                  95
Thr Met Val Glu Gln Met His Glu Asp Ile Ile Ser Leu Trp Asp Gln
            100                 105                 110
Ser Leu Lys Pro Cys Val Gln Leu Thr Pro Leu Cys Val Thr Leu Asn
        115                 120                 125
Cys Arg Asn Tyr Thr Asn Asn Ser Thr Ile Ser Ser Asn Asn Asn Thr
    130                 135                 140
Ile Asn Ser Thr Val Ser Pro Asn Ser Ser Thr Ile Ser Ser Asp Met
145                 150                 155                 160
Gln Glu Val Lys Asn Cys Ser Phe Asn Met Thr Thr Glu Leu Arg Asp
                165                 170                 175
Lys Lys Arg Lys Val Tyr Ala Leu Phe Tyr Arg Leu Asp Ile Val Pro
            180                 185                 190
Leu Ser Asn Asp Ser Asp Glu Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Phe Ala Ile Leu Lys Cys Lys Asp Lys
225                 230                 235                 240
Lys Phe Asn Gly Thr Gly Pro Cys Asn Asn Val Ser Thr Val Gln Cys
                245                 250                 255
Thr His Gly Ile Lys Pro Val Val Ser Thr Gln Leu Leu Asn Gly
            260                 265                 270
Ser Leu Ala Glu Glu Glu Ile Val Ile Arg Ser Glu Asp Ile Ser Asn
        275                 280                 285
Asn Ala Lys Thr Ile Ile Val Gln Leu Val Asn Pro Val Arg Ile Asn
    290                 295                 300
Cys Thr Arg Pro Gly Asn Asn Thr Arg Lys Ser Val Arg Ile Gly Pro
305                 310                 315                 320
Gly Gln Thr Phe Tyr Ala Asn Glu Ile Ile Gly Asn Ile Arg Gln Ala
                325                 330                 335
His Cys Asn Val Ser Arg Ser Glu Trp Asn Arg Thr Leu Gln Gln Val
            340                 345                 350
Ala Val Gln Leu Arg Lys Leu Trp Asn Lys Thr Ile Ile Phe Asn Lys
        355                 360                 365
Thr Ser Gly Gly Asp Val Glu Ile Thr Thr His Ser Phe Asn Cys Arg
```

-continued

```
            370                 375                 380
Gly Glu Phe Phe Tyr Cys Asn Thr Ser Arg Leu Phe Asn Ser Thr Trp
385                 390                 395                 400

Asp Gly Asn Asn Thr Arg Glu Asp Asn Ser Thr Trp Gly Asn Asn Ser
                405                 410                 415

Ser Asn Asp Ile Ile Thr Leu Gln Cys Lys Ile Lys Gln Ile Val Asn
                420                 425                 430

Met Trp Gln Arg Val Gln Ala Met Tyr Ala Pro Pro Ile Pro Gly
                435                 440                 445

Glu Leu Arg Cys Glu Ser Asn Ile Thr Gly Leu Leu Leu Thr Arg Asp
                450                 455                 460

Gly Gly Gly Glu Asn Lys Asp Arg Leu Asn Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Lys Ile Glu Pro Leu Gly Val Ala Pro Thr His Ala Lys Arg
                500                 505                 510

Arg Val Val Gln Arg Glu Lys Arg Ala Val Gly Leu Gly Ala Val Phe
                515                 520                 525

Leu Gly Phe Leu Gly Ala Ala Gly Ser Thr Met Gly Ala Ala Ser Ile
530                 535                 540

Thr Leu Thr Val Gln Ala Arg Gln Leu Leu Ser Gly Ile Val Gln Gln
545                 550                 555                 560

Gln Ser Asn Leu Leu Arg Ala Ile Glu Ala Gln Gln His Leu Leu Lys
                565                 570                 575

Leu Thr Val Trp Gly Ile Lys Gln Leu Gln Ala Arg Val Leu Ala Leu
                580                 585                 590

Glu Arg Tyr Leu Arg Asp Gln Gln Leu Leu Gly Ile Trp Gly Cys Ser
                595                 600                 605

Gly Lys Leu Ile Cys Thr Thr Thr Val Pro Trp Asn Ser Ser Trp Ser
610                 615                 620

Asn Lys Thr Tyr Lys Glu Ile Trp Asp Asn Met Thr Trp Leu Glu Trp
625                 630                 635                 640

Asp Lys Glu Ile Ser Arg Tyr Thr Asn Val Ile Tyr Asp Leu Ile Glu
                645                 650                 655

Glu Ser Gln Asn Gln Gln Lys Asn Glu Gln Asp Leu Leu Ala Leu
                660                 665                 670

Asp Thr Trp Ala Ser Leu Trp Asn Trp Phe Asn Ile Ser Asn Trp Leu
                675                 680                 685

Trp Tyr Ile Arg Leu Phe Ile Met Ile Val Gly Gly Leu Ile Gly Leu
                690                 695                 700

Arg Ile Val Phe Ala Val Leu Ala Ile Ile Asn Arg Val Arg Gln Gly
705                 710                 715                 720

Tyr Ser Pro Leu Ser Phe Gln Thr Leu Thr His Gln Gln Arg Glu Gln
                725                 730                 735

Pro Asp Arg Pro Glu Arg Ile Glu Glu Gly Gly Gly Glu Gln Asp Arg
                740                 745                 750

Asp Arg Ser Val Arg Leu Val Ser Gly Phe Leu Ala Leu Ala Trp Asp
                755                 760                 765

Asp Leu Arg Ser Leu Cys Leu Phe Ser Tyr His Arg Leu Arg Asp Phe
                770                 775                 780

Leu Leu Ile Val Ile Arg Thr Val Glu Leu Leu Ala His Ser Ser Leu
785                 790                 795                 800
```

```
Lys Gly Leu Arg Leu Gly Trp Glu Ala Leu Lys Tyr Leu Trp Ser Leu
            805                 810                 815

Leu Ser Tyr Trp Gly Gln Glu Leu Lys Asn Ser Ala Ile Ser Leu Leu
            820                 825                 830

Asp Thr Thr Ala Ile Ala Val Ala Asn Trp Thr Asp Arg Val Ile Glu
            835                 840                 845

Ile Gly Gln Arg Ile Gly Arg Ala Ile Trp Asn Ile Pro Arg Arg Ile
            850                 855                 860

Arg Gln Gly Val Glu Arg Ala Leu Leu
865                 870

<210> SEQ ID NO 44
<211> LENGTH: 2547
<212> TYPE: DNA
<213> ORGANISM: Human immunodeficiency virus type 1
<220> FEATURE:
<221> NAME/KEY: CDS
<222> LOCATION: (1)..(2547)

<400> SEQUENCE: 44 atg aga gtg agg ggg atc agg agg aat tgt cag cac ttg tgg aaa tgg      48
Met Arg Val Arg Gly Ile Arg Arg Asn Cys Gln His Leu Trp Lys Trp
1               5                   10                  15 ggc acc atg ctc ctt ggg ata ttg atg atc tgt aat gct aca gaa aat      96
Gly Thr Met Leu Leu Gly Ile Leu Met Ile Cys Asn Ala Thr Glu Asn
            20                  25                  30 ttg tgg gtc acc gtc tat tat ggg gta cct gtg tgg aaa gaa gca acc     144
Leu Trp Val Thr Val Tyr Tyr Gly Val Pro Val Trp Lys Glu Ala Thr
        35                  40                  45 acc act cta ttt tgt gca tca gat gcc aaa gca tat gat aca gag gta     192
Thr Thr Leu Phe Cys Ala Ser Asp Ala Lys Ala Tyr Asp Thr Glu Val
    50                  55                  60 cat aat gtc tgg gcc aca cat gcc tgt gta ccc aca gac ccc aac cca     240
His Asn Val Trp Ala Thr His Ala Cys Val Pro Thr Asp Pro Asn Pro
65                  70                  75                  80 caa gaa atg gaa ttg aaa aat gtg aca gaa aat ttt aac atg tgg aaa     288
Gln Glu Met Glu Leu Lys Asn Val Thr Glu Asn Phe Asn Met Trp Lys
                85                  90                  95 aat aac atg gta gaa cag atg cat gag gat ata att agt tta tgg gat     336
Asn Asn Met Val Glu Gln Met His Glu Asp Ile Ile Ser Leu Trp Asp
            100                 105                 110 caa agc cta aag cca tgt gta aaa tta acc cca ctc tgt gtt act tta     384
Gln Ser Leu Lys Pro Cys Val Lys Leu Thr Pro Leu Cys Val Thr Leu
        115                 120                 125 aat tgc act gat ttg aga aat gct act aat acc act agt agt agc ggg     432
Asn Cys Thr Asp Leu Arg Asn Ala Thr Asn Thr Thr Ser Ser Ser Gly
    130                 135                 140 gaa acg atg gag gga gga gaa atg aaa aat tgc tct ttt aat atc acc     480
Glu Thr Met Glu Gly Gly Glu Met Lys Asn Cys Ser Phe Asn Ile Thr
145                 150                 155                 160 aca agc ata aga gat aag ctg cag aaa gta tat gca ctt ttt tat aaa     528
Thr Ser Ile Arg Asp Lys Leu Gln Lys Val Tyr Ala Leu Phe Tyr Lys
                165                 170                 175 ctt gat gta aca cca ata gaa aat gat act act agc tat agg ttg ata     576
Leu Asp Val Thr Pro Ile Glu Asn Asp Thr Thr Ser Tyr Arg Leu Ile
            180                 185                 190 agt tgt aac acc tcg gtc att aca cag gcc tgt cca aag ata tcc ttt     624
Ser Cys Asn Thr Ser Val Ile Thr Gln Ala Cys Pro Lys Ile Ser Phe
        195                 200                 205 gag cca att ccc ata cac tat tgt gcc ccg gct ggt ttt gcg att cta     672
Glu Pro Ile Pro Ile His Tyr Cys Ala Pro Ala Gly Phe Ala Ile Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 210 |     |     |     |     | 215 |     |     |     |     | 220 |     |     |     |      |
| aag | tgt | aag | gat | aca | aag | ttc | aat | gga | aca | gga | cca | tgt | aca | aac | gtc | 720  |
| Lys | Cys | Lys | Asp | Thr | Lys | Phe | Asn | Gly | Thr | Gly | Pro | Cys | Thr | Asn | Val |      |
| 225 |     |     |     | 230 |     |     |     |     | 235 |     |     |     |     | 240 |     |      |
| agc | aca | gta | caa | tgt | aca | cat | gga | att | aaa | cca | gta | gta | tca | act | caa | 768  |
| Ser | Thr | Val | Gln | Cys | Thr | His | Gly | Ile | Lys | Pro | Val | Val | Ser | Thr | Gln |      |
|     |     |     |     | 245 |     |     |     |     | 250 |     |     |     |     | 255 |     |      |
| ctg | ctg | tta | aat | ggc | agt | cta | gca | gaa | gaa | gag | gta | gta | att | aga | tcc | 816  |
| Leu | Leu | Leu | Asn | Gly | Ser | Leu | Ala | Glu | Glu | Glu | Val | Val | Ile | Arg | Ser |      |
|     |     |     | 260 |     |     |     |     | 265 |     |     |     |     | 270 |     |     |      |
| agc | aat | ttc | acg | gac | aat | act | aaa | gtc | ata | ata | gtg | cag | ctg | aat | aac | 864  |
| Ser | Asn | Phe | Thr | Asp | Asn | Thr | Lys | Val | Ile | Ile | Val | Gln | Leu | Asn | Asn |      |
|     |     | 275 |     |     |     |     | 280 |     |     |     |     | 285 |     |     |     |      |
| tct | gta | gaa | atc | aat | tgt | aca | agg | ccc | aac | aac | aat | aca | aga | aaa | agt | 912  |
| Ser | Val | Glu | Ile | Asn | Cys | Thr | Arg | Pro | Asn | Asn | Asn | Thr | Arg | Lys | Ser |      |
| 290 |     |     |     |     | 295 |     |     |     |     | 300 |     |     |     |     |     |      |
| ata | cct | ata | gga | cca | ggc | aga | gca | ttt | tat | aca | aca | gga | gaa | ata | ata | 960  |
| Ile | Pro | Ile | Gly | Pro | Gly | Arg | Ala | Phe | Tyr | Thr | Thr | Gly | Glu | Ile | Ile |      |
| 305 |     |     |     | 310 |     |     |     |     | 315 |     |     |     |     | 320 |     |      |
| gga | gat | ata | aga | caa | gca | cat | tgt | aac | ctt | agt | gga | gca | aaa | tgg | aat | 1008 |
| Gly | Asp | Ile | Arg | Gln | Ala | His | Cys | Asn | Leu | Ser | Gly | Ala | Lys | Trp | Asn |      |
|     |     |     |     | 325 |     |     |     |     | 330 |     |     |     |     | 335 |     |      |
| gac | gct | tta | aaa | cag | ata | gtt | aca | aaa | tta | aga | gaa | caa | ttt | aag | aat | 1056 |
| Asp | Ala | Leu | Lys | Gln | Ile | Val | Thr | Lys | Leu | Arg | Glu | Gln | Phe | Lys | Asn |      |
|     |     |     | 340 |     |     |     |     | 345 |     |     |     |     | 350 |     |     |      |
| aaa | aca | ata | atc | ttt | aat | caa | tcc | tca | gga | ggg | gac | cca | gaa | att | gta | 1104 |
| Lys | Thr | Ile | Ile | Phe | Asn | Gln | Ser | Ser | Gly | Gly | Asp | Pro | Glu | Ile | Val |      |
|     |     | 355 |     |     |     |     | 360 |     |     |     |     | 365 |     |     |     |      |
| acg | cac | agt | ttt | aat | tgt | gga | ggg | gaa | ttt | ttc | tac | tgt | aat | aca | aca | 1152 |
| Thr | His | Ser | Phe | Asn | Cys | Gly | Gly | Glu | Phe | Phe | Tyr | Cys | Asn | Thr | Thr |      |
|     | 370 |     |     |     |     | 375 |     |     |     |     | 380 |     |     |     |     |      |
| aaa | ctg | ttt | aat | agt | act | tgg | aat | ggt | act | gaa | ggg | tca | aac | aac | act | 1200 |
| Lys | Leu | Phe | Asn | Ser | Thr | Trp | Asn | Gly | Thr | Glu | Gly | Ser | Asn | Asn | Thr |      |
| 385 |     |     |     |     | 390 |     |     |     |     | 395 |     |     |     |     | 400 |      |
| gga | gga | gaa | aat | gac | acg | atc | aca | ctc | cca | tgc | aga | ata | aaa | caa | att | 1248 |
| Gly | Gly | Glu | Asn | Asp | Thr | Ile | Thr | Leu | Pro | Cys | Arg | Ile | Lys | Gln | Ile |      |
|     |     |     |     | 405 |     |     |     |     | 410 |     |     |     |     | 415 |     |      |
| gta | aac | atg | tgg | cag | gaa | gta | gga | aaa | gca | atg | tat | gca | cct | ccc | atc | 1296 |
| Val | Asn | Met | Trp | Gln | Glu | Val | Gly | Lys | Ala | Met | Tyr | Ala | Pro | Pro | Ile |      |
|     |     |     | 420 |     |     |     |     | 425 |     |     |     |     | 430 |     |     |      |
| aga | gga | caa | att | aga | tgt | tca | tca | aat | att | aca | ggg | ctg | ata | tta | aca | 1344 |
| Arg | Gly | Gln | Ile | Arg | Cys | Ser | Ser | Asn | Ile | Thr | Gly | Leu | Ile | Leu | Thr |      |
|     |     | 435 |     |     |     |     | 440 |     |     |     |     | 445 |     |     |     |      |
| aga | gat | ggt | ggt | aat | aat | aat | aac | acg | aac | gag | acc | ttc | aga | cct | gga | 1392 |
| Arg | Asp | Gly | Gly | Asn | Asn | Asn | Asn | Thr | Asn | Glu | Thr | Phe | Arg | Pro | Gly |      |
| 450 |     |     |     |     | 455 |     |     |     |     | 460 |     |     |     |     |     |      |
| gga | gga | gat | atg | agg | gac | aat | tgg | aga | agt | gaa | tta | tat | aaa | tat | aaa | 1440 |
| Gly | Gly | Asp | Met | Arg | Asp | Asn | Trp | Arg | Ser | Glu | Leu | Tyr | Lys | Tyr | Lys |      |
| 465 |     |     |     | 470 |     |     |     |     | 475 |     |     |     |     | 480 |     |      |
| gta | gta | aaa | att | gaa | cca | tta | gga | gta | gca | ccc | acc | agg | gca | aag | aga | 1488 |
| Val | Val | Lys | Ile | Glu | Pro | Leu | Gly | Val | Ala | Pro | Thr | Arg | Ala | Lys | Arg |      |
|     |     |     | 485 |     |     |     |     | 490 |     |     |     |     | 495 |     |     |      |
| aga | gtg | gtg | cag | aga | gaa | aaa | aga | gca | ata | gcg | gga | gct | gtg | ttc | ctt | 1536 |
| Arg | Val | Val | Gln | Arg | Glu | Lys | Arg | Ala | Ile | Ala | Gly | Ala | Val | Phe | Leu |      |
|     |     | 500 |     |     |     |     | 505 |     |     |     |     | 510 |     |     |     |      |
| ggg | ttc | ttg | gga | gca | gca | gga | agc | act | atg | ggc | gca | gcg | tca | gtg | gcg | 1584 |
| Gly | Phe | Leu | Gly | Ala | Ala | Gly | Ser | Thr | Met | Gly | Ala | Ala | Ser | Val | Ala |      |
|     | 515 |     |     |     |     | 520 |     |     |     |     | 525 |     |     |     |     |      |
| ctg | acg | gta | cag | gcc | aga | cta | tta | tta | tct | ggt | ata | gtg | caa | cag | cag | 1632 |
| Leu | Thr | Val | Gln | Ala | Arg | Leu | Leu | Leu | Ser | Gly | Ile | Val | Gln | Gln | Gln |      |

```
                                              -continued
       530                  535                 540
aac aat ttg ctg agg gct att gag gcg caa cag cat ctg ttg caa ctc    1680
Asn Asn Leu Leu Arg Ala Ile Glu Ala Gln Gln His Leu Leu Gln Leu
545                 550                 555                 560 aca gtc tgg ggc atc aag cag ctc cag gca aga gtc ctg gct gtg gaa    1728
Thr Val Trp Gly Ile Lys Gln Leu Gln Ala Arg Val Leu Ala Val Glu
                565                 570                 575 aga tac cta agg gat caa cag ctc ctg ggg att tgg ggt tgc tct gga    1776
Arg Tyr Leu Arg Asp Gln Gln Leu Leu Gly Ile Trp Gly Cys Ser Gly
            580                 585                 590 aaa ctc att tgc acc act act gtg cct tgg aat act agt tgg agt aat    1824
Lys Leu Ile Cys Thr Thr Thr Val Pro Trp Asn Thr Ser Trp Ser Asn
        595                 600                 605 aaa tct gtg gat tac att tgg aaa aac atg acc tgg atg cag tgg gaa    1872
Lys Ser Val Asp Tyr Ile Trp Lys Asn Met Thr Trp Met Gln Trp Glu
    610                 615                 620 aaa gaa att gat aat tac aca agc tta ata tac acc tta att gaa gaa    1920
Lys Glu Ile Asp Asn Tyr Thr Ser Leu Ile Tyr Thr Leu Ile Glu Glu
625                 630                 635                 640 tcg caa tac cag caa gaa aag aat gaa caa gaa tta ttg gaa tta gat    1968
Ser Gln Tyr Gln Gln Glu Lys Asn Glu Gln Glu Leu Leu Glu Leu Asp
                645                 650                 655 aaa tgg gca agt ttg tgg aat tgg ttt gac ata aca aac tgg ctg tgg    2016
Lys Trp Ala Ser Leu Trp Asn Trp Phe Asp Ile Thr Asn Trp Leu Trp
            660                 665                 670 tac ata aaa tta ttc ata atg ata gta gga ggc ttg gta ggt tta aga    2064
Tyr Ile Lys Leu Phe Ile Met Ile Val Gly Gly Leu Val Gly Leu Arg
        675                 680                 685 ata gtt ttt gct gta ctt tct ata gtg aat aga gtt agg cag gga tac    2112
Ile Val Phe Ala Val Leu Ser Ile Val Asn Arg Val Arg Gln Gly Tyr
    690                 695                 700 tca cca tta tcg ttc cag acc cgc ccc cca gcc ccg agg gga ccc gac    2160
Ser Pro Leu Ser Phe Gln Thr Arg Pro Pro Ala Pro Arg Gly Pro Asp
705                 710                 715                 720 agg ccc gaa gga atc gaa gaa gaa ggt gga gag cga aac aga gac aga    2208
Arg Pro Glu Gly Ile Glu Glu Glu Gly Gly Glu Arg Asn Arg Asp Arg
                725                 730                 735 tcc gaa caa tta gtg gat gga ttc ttg gca ctt atc tgg atc gac ctg    2256
Ser Glu Gln Leu Val Asp Gly Phe Leu Ala Leu Ile Trp Ile Asp Leu
            740                 745                 750 cgg agc ctg tgc ctc ttc atc tac cac cgc ttg aga gac tta ctc ttg    2304
Arg Ser Leu Cys Leu Phe Ile Tyr His Arg Leu Arg Asp Leu Leu Leu
        755                 760                 765 att gta acg agg att gtg gaa ctt ctg gga cgc agg ggg tgg gaa atc    2352
Ile Val Thr Arg Ile Val Glu Leu Leu Gly Arg Arg Gly Trp Glu Ile
    770                 775                 780 ctc aaa tat tgg tgg aat ctc cta cag tat tgg agt cag gaa cta aag    2400
Leu Lys Tyr Trp Trp Asn Leu Leu Gln Tyr Trp Ser Gln Glu Leu Lys
785                 790                 795                 800 aat agt gct gtt agc ttg ttc aat gcc aca gcc ata gca gta gct gag    2448
Asn Ser Ala Val Ser Leu Phe Asn Ala Thr Ala Ile Ala Val Ala Glu
                805                 810                 815 ggg act gat agg gtt ata gaa ata tta caa aga gct ttt aga gct act    2496
Gly Thr Asp Arg Val Ile Glu Ile Leu Gln Arg Ala Phe Arg Ala Thr
            820                 825                 830 ctc cac ata cct aca cga ata aga cag ggc ttg gaa agg gct ttg cta    2544
Leu His Ile Pro Thr Arg Ile Arg Gln Gly Leu Glu Arg Ala Leu Leu
        835                 840                 845 taa                                                                2547
```

```
<210> SEQ ID NO 45
<211> LENGTH: 848
<212> TYPE: PRT
<213> ORGANISM: Human immunodeficiency virus type 1

<400> SEQUENCE: 45
```

| | | | | | | | | | | | | | |
|---|---|---|---|---|---|---|---|---|---|---|---|---|---|
| Met | Arg | Val | Arg | Gly | Ile | Arg | Arg | Asn | Cys | Gln | His | Leu | Trp | Lys | Trp |
| 1 | | | | 5 | | | | | 10 | | | | | 15 | |

| Gly | Thr | Met | Leu | Leu | Gly | Ile | Leu | Met | Ile | Cys | Asn | Ala | Thr | Glu | Asn |
| 20 | 25 | 30 |

| Leu | Trp | Val | Thr | Val | Tyr | Tyr | Gly | Val | Pro | Val | Trp | Lys | Glu | Ala | Thr |
| 35 | 40 | 45 |

| Thr | Thr | Leu | Phe | Cys | Ala | Ser | Asp | Ala | Lys | Ala | Tyr | Asp | Thr | Glu | Val |
| 50 | 55 | 60 |

| His | Asn | Val | Trp | Ala | Thr | His | Ala | Cys | Val | Pro | Thr | Asp | Pro | Asn | Pro |
| 65 | 70 | 75 | 80 |

| Gln | Glu | Met | Glu | Leu | Lys | Asn | Val | Thr | Glu | Asn | Phe | Asn | Met | Trp | Lys |
| 85 | 90 | 95 |

| Asn | Asn | Met | Val | Glu | Gln | Met | His | Glu | Asp | Ile | Ile | Ser | Leu | Trp | Asp |
| 100 | 105 | 110 |

| Gln | Ser | Leu | Lys | Pro | Cys | Val | Lys | Leu | Thr | Pro | Leu | Cys | Val | Thr | Leu |
| 115 | 120 | 125 |

| Asn | Cys | Thr | Asp | Leu | Arg | Asn | Ala | Thr | Asn | Thr | Ser | Ser | Ser | Gly |
| 130 | 135 | 140 |

| Glu | Thr | Met | Glu | Gly | Gly | Glu | Met | Lys | Asn | Cys | Ser | Phe | Asn | Ile | Thr |
| 145 | 150 | 155 | 160 |

| Thr | Ser | Ile | Arg | Asp | Lys | Leu | Gln | Lys | Val | Tyr | Ala | Leu | Phe | Tyr | Lys |
| 165 | 170 | 175 |

| Leu | Asp | Val | Thr | Pro | Ile | Glu | Asn | Asp | Thr | Thr | Ser | Tyr | Arg | Leu | Ile |
| 180 | 185 | 190 |

| Ser | Cys | Asn | Thr | Ser | Val | Ile | Thr | Gln | Ala | Cys | Pro | Lys | Ile | Ser | Phe |
| 195 | 200 | 205 |

| Glu | Pro | Ile | Pro | Ile | His | Tyr | Cys | Ala | Pro | Ala | Gly | Phe | Ala | Ile | Leu |
| 210 | 215 | 220 |

| Lys | Cys | Lys | Asp | Thr | Lys | Phe | Asn | Gly | Thr | Gly | Pro | Cys | Thr | Asn | Val |
| 225 | 230 | 235 | 240 |

| Ser | Thr | Val | Gln | Cys | Thr | His | Gly | Ile | Lys | Pro | Val | Val | Ser | Thr | Gln |
| 245 | 250 | 255 |

| Leu | Leu | Leu | Asn | Gly | Ser | Leu | Ala | Glu | Glu | Val | Val | Ile | Arg | Ser |
| 260 | 265 | 270 |

| Ser | Asn | Phe | Thr | Asp | Asn | Thr | Lys | Val | Ile | Ile | Val | Gln | Leu | Asn | Asn |
| 275 | 280 | 285 |

| Ser | Val | Glu | Ile | Asn | Cys | Thr | Arg | Pro | Asn | Asn | Asn | Thr | Arg | Lys | Ser |
| 290 | 295 | 300 |

| Ile | Pro | Ile | Gly | Pro | Gly | Arg | Ala | Phe | Tyr | Thr | Thr | Gly | Glu | Ile | Ile |
| 305 | 310 | 315 | 320 |

| Gly | Asp | Ile | Arg | Gln | Ala | His | Cys | Asn | Leu | Ser | Gly | Ala | Lys | Trp | Asn |
| 325 | 330 | 335 |

| Asp | Ala | Leu | Lys | Gln | Ile | Val | Thr | Lys | Leu | Arg | Glu | Gln | Phe | Lys | Asn |
| 340 | 345 | 350 |

| Lys | Thr | Ile | Ile | Phe | Asn | Gln | Ser | Ser | Gly | Gly | Asp | Pro | Glu | Ile | Val |
| 355 | 360 | 365 |

| Thr | His | Ser | Phe | Asn | Cys | Gly | Gly | Glu | Phe | Phe | Tyr | Cys | Asn | Thr | Thr |
| 370 | 375 | 380 |

-continued

```
Lys Leu Phe Asn Ser Thr Trp Asn Gly Thr Glu Gly Ser Asn Asn Thr
385                 390                 395                 400

Gly Gly Glu Asn Asp Thr Ile Thr Leu Pro Cys Arg Ile Lys Gln Ile
            405                 410                 415

Val Asn Met Trp Gln Glu Val Gly Lys Ala Met Tyr Ala Pro Pro Ile
        420                 425                 430

Arg Gly Gln Ile Arg Cys Ser Ser Asn Ile Thr Gly Leu Ile Leu Thr
    435                 440                 445

Arg Asp Gly Gly Asn Asn Asn Thr Asn Glu Thr Phe Arg Pro Gly
450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Arg Ala Lys Arg
            485                 490                 495

Arg Val Val Gln Arg Glu Lys Arg Ala Ile Ala Gly Ala Val Phe Leu
        500                 505                 510

Gly Phe Leu Gly Ala Ala Gly Ser Thr Met Gly Ala Ala Ser Val Ala
    515                 520                 525

Leu Thr Val Gln Ala Arg Leu Leu Ser Gly Ile Val Gln Gln
530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
            565                 570                 575

Arg Tyr Leu Arg Asp Gln Gln Leu Leu Gly Ile Trp Gly Cys Ser Gly
        580                 585                 590

Lys Leu Ile Cys Thr Thr Thr Val Pro Trp Asn Thr Ser Trp Ser Asn
    595                 600                 605

Lys Ser Val Asp Tyr Ile Trp Lys Asn Met Thr Trp Met Gln Trp Glu
610                 615                 620

Lys Glu Ile Asp Asn Tyr Thr Ser Leu Ile Tyr Thr Leu Ile Glu Glu
625                 630                 635                 640

Ser Gln Tyr Gln Gln Glu Lys Asn Glu Gln Glu Leu Leu Glu Leu Asp
            645                 650                 655

Lys Trp Ala Ser Leu Trp Asn Trp Phe Asp Ile Thr Asn Trp Leu Trp
        660                 665                 670

Tyr Ile Lys Leu Phe Ile Met Ile Val Gly Gly Leu Val Gly Leu Arg
    675                 680                 685

Ile Val Phe Ala Val Leu Ser Ile Val Asn Arg Val Arg Gln Gly Tyr
690                 695                 700

Ser Pro Leu Ser Phe Gln Thr Arg Pro Pro Ala Pro Arg Gly Pro Asp
705                 710                 715                 720

Arg Pro Glu Gly Ile Glu Glu Glu Gly Gly Glu Arg Asn Arg Asp Arg
            725                 730                 735

Ser Glu Gln Leu Val Asp Gly Phe Leu Ala Leu Ile Trp Ile Asp Leu
        740                 745                 750

Arg Ser Leu Cys Leu Phe Ile Tyr His Arg Leu Arg Asp Leu Leu Leu
    755                 760                 765

Ile Val Thr Arg Ile Val Glu Leu Leu Gly Arg Arg Gly Trp Glu Ile
770                 775                 780

Leu Lys Tyr Trp Trp Asn Leu Leu Gln Tyr Trp Ser Gln Glu Leu Lys
785                 790                 795                 800

Asn Ser Ala Val Ser Leu Phe Asn Ala Thr Ala Ile Ala Val Ala Glu
            805                 810                 815
```

```
Gly Thr Asp Arg Val Ile Glu Ile Leu Gln Arg Ala Phe Arg Ala Thr
            820                 825                 830

Leu His Ile Pro Thr Arg Ile Arg Gln Gly Leu Glu Arg Ala Leu Leu
            835                 840                 845

<210> SEQ ID NO 46
<211> LENGTH: 2541
<212> TYPE: DNA
<213> ORGANISM: Human immunodeficiency virus type 1
<220> FEATURE:
<221> NAME/KEY: CDS
<222> LOCATION: (1)..(2541)
<220> FEATURE:
<221> NAME/KEY: misc_feature
<222> LOCATION: (300)..(300)
<223> OTHER INFORMATION: r is g or a
<220> FEATURE:
<221> NAME/KEY: misc_feature
<222> LOCATION: (2495)..(2495)
<223> OTHER INFORMATION: m is a or c

<400> SEQUENCE: 46 atg aga gtg agg ggg atg cag agg aat tgg cag cac ttg ggg aaa tgg        48
Met Arg Val Arg Gly Met Gln Arg Asn Trp Gln His Leu Gly Lys Trp
 1               5                  10                  15 ggc ctt tta ttc ctg ggg ata tta ata atc tgt aat gct gca gac aac        96
Gly Leu Leu Phe Leu Gly Ile Leu Ile Ile Cys Asn Ala Ala Asp Asn
             20                  25                  30 ttg tgg gtc aca gtc tat tat ggg gta cct gtg tgg aaa gaa gca acc       144
Leu Trp Val Thr Val Tyr Tyr Gly Val Pro Val Trp Lys Glu Ala Thr
         35                  40                  45 act act cta ttt tgt gca tca gat gct aaa gga tat gag aaa gag gta       192
Thr Thr Leu Phe Cys Ala Ser Asp Ala Lys Gly Tyr Glu Lys Glu Val
     50                  55                  60 cat aat gtc tgg gct aca cat gcc tgt gta ccc aca gac ccc aac cca       240
His Asn Val Trp Ala Thr His Ala Cys Val Pro Thr Asp Pro Asn Pro
 65                  70                  75                  80 caa gaa gta gtt ctg gaa aat gta aca gaa aat ttt aat atg tgg aaa       288
Gln Glu Val Val Leu Glu Asn Val Thr Glu Asn Phe Asn Met Trp Lys
                 85                  90                  95 aat aac atg gtr gaa caa atg cat gaa gat ata atc agt tta tgg gat       336
Asn Asn Met Xaa Glu Gln Met His Glu Asp Ile Ile Ser Leu Trp Asp
            100                 105                 110 caa agc cta aag cca tgt gta aag cta acc cca ctc tgt gtt act tta       384
Gln Ser Leu Lys Pro Cys Val Lys Leu Thr Pro Leu Cys Val Thr Leu
        115                 120                 125 agc tgt aat aat gtc aat ggc act gcc act gat caa aac agc acc ctg       432
Ser Cys Asn Asn Val Asn Gly Thr Ala Thr Asp Gln Asn Ser Thr Leu
    130                 135                 140 aag gaa gag tca gga gca ata caa aac tgt tct ttc aat atg acc aca       480
Lys Glu Glu Ser Gly Ala Ile Gln Asn Cys Ser Phe Asn Met Thr Thr
145                 150                 155                 160 gaa gta aga gat aag aag ctg caa gta cat gca ctt ttt tat aga ctt       528
Glu Val Arg Asp Lys Lys Leu Gln Val His Ala Leu Phe Tyr Arg Leu
                165                 170                 175 gat ata gta cca atc agc aat agc aat ggc agt gat ggc aat agg gaa       576
Asp Ile Val Pro Ile Ser Asn Ser Asn Gly Ser Asp Gly Asn Arg Glu
            180                 185                 190 tat agg cta ata aat tgt aat acc tca acc att aaa cag gct tgt cca       624
Tyr Arg Leu Ile Asn Cys Asn Thr Ser Thr Ile Lys Gln Ala Cys Pro
        195                 200                 205 aag gta tct tgg gat cca att ccc ata cat tat tgt gct ccg gct ggt       672
Lys Val Ser Trp Asp Pro Ile Pro Ile His Tyr Cys Ala Pro Ala Gly
```

```
              210                 215                 220
tat gcg att cta aaa tgt aat aat aaa aag ttc aat ggg aca ggg cca       720
Tyr Ala Ile Leu Lys Cys Asn Asn Lys Lys Phe Asn Gly Thr Gly Pro
225                 230                 235                 240 tgc cag aat gtc agc aca gta caa tgt aca cat gga att aag cca gtg       768
Cys Gln Asn Val Ser Thr Val Gln Cys Thr His Gly Ile Lys Pro Val
                245                 250                 255 gta tca act caa ttg ctg tta aat ggc agc cta gca gaa gaa agt ata       816
Val Ser Thr Gln Leu Leu Leu Asn Gly Ser Leu Ala Glu Glu Ser Ile
            260                 265                 270 ata ata aga tct caa aat atc tca gat aat aca aaa act ata ata gta       864
Ile Ile Arg Ser Gln Asn Ile Ser Asp Asn Thr Lys Thr Ile Ile Val
        275                 280                 285 cac ctt aat gaa tct gta cag att aat tgt aca aga ccc aac aac aat       912
His Leu Asn Glu Ser Val Gln Ile Asn Cys Thr Arg Pro Asn Asn Asn
    290                 295                 300 aca aga aaa ggt ata cat tta gga cca gga caa gca ttc tat gca aca       960
Thr Arg Lys Gly Ile His Leu Gly Pro Gly Gln Ala Phe Tyr Ala Thr
305                 310                 315                 320 ggt gac ata ata gga gac ata aga aag gca cat tgt aac att agt aga      1008
Gly Asp Ile Ile Gly Asp Ile Arg Lys Ala His Cys Asn Ile Ser Arg
                325                 330                 335 ata caa tgg agt aac act tta gaa caa gta aaa gca gag tta aag cct      1056
Ile Gln Trp Ser Asn Thr Leu Glu Gln Val Lys Ala Glu Leu Lys Pro
            340                 345                 350 cat ttt aat aat aaa aca ata gaa ttt gaa cca cca tcc cca gga gga      1104
His Phe Asn Asn Lys Thr Ile Glu Phe Glu Pro Pro Ser Pro Gly Gly
        355                 360                 365 gac cta gaa att aca atg cat agt ttt aat tgt aga gga gaa ttt ttc      1152
Asp Leu Glu Ile Thr Met His Ser Phe Asn Cys Arg Gly Glu Phe Phe
    370                 375                 380 tac tgc aat aca tca gga ctg ttt aat acc aca gaa tcc aat gaa act      1200
Tyr Cys Asn Thr Ser Gly Leu Phe Asn Thr Thr Glu Ser Asn Glu Thr
385                 390                 395                 400 ata gtt gtt ctc cca tgt aaa ata aaa caa att gta aga atg tgg cag      1248
Ile Val Val Leu Pro Cys Lys Ile Lys Gln Ile Val Arg Met Trp Gln
                405                 410                 415 gga gta ggg caa gca atg tat gct cct ccc att gca gga aat att acc      1296
Gly Val Gly Gln Ala Met Tyr Ala Pro Pro Ile Ala Gly Asn Ile Thr
            420                 425                 430 tgt aac tca aat att aca ggc cta ctg ttg aca aga gat ggt ggt cag      1344
Cys Asn Ser Asn Ile Thr Gly Leu Leu Leu Thr Arg Asp Gly Gly Gln
        435                 440                 445 cat aat gat agt aat act act gag acc ttc aga cct ggg gga gga gat      1392
His Asn Asp Ser Asn Thr Thr Glu Thr Phe Arg Pro Gly Gly Gly Asp
    450                 455                 460 atg aga gac aat tgg aga agt gaa cta tat aaa tat aaa gta gta gaa      1440
Met Arg Asp Asn Trp Arg Ser Glu Leu Tyr Lys Tyr Lys Val Val Glu
465                 470                 475                 480 att gag cca cta gga gta gca ccc acc agg gca aaa aga caa gtg gtg      1488
Ile Glu Pro Leu Gly Val Ala Pro Thr Arg Ala Lys Arg Gln Val Val
                485                 490                 495 aag aga gaa aaa aga gca gtg gga ata gga gct ttg ttc ctt ggg ttc      1536
Lys Arg Glu Lys Arg Ala Val Gly Ile Gly Ala Leu Phe Leu Gly Phe
            500                 505                 510 ttg gga gca gca gga agc act atg ggc gcg gcg tca ata acg ctg acg      1584
Leu Gly Ala Ala Gly Ser Thr Met Gly Ala Ala Ser Ile Thr Leu Thr
        515                 520                 525 gta cag gcc aga caa tta ttg tct gga ata gtg caa cag caa aac aat      1632
Val Gln Ala Arg Gln Leu Leu Ser Gly Ile Val Gln Gln Gln Asn Asn
```

```
                530             535             540
ttg ctg agg gct att gaa gcg caa cag cat ctg ttg cag ctc aca gtc    1680
Leu Leu Arg Ala Ile Glu Ala Gln Gln His Leu Leu Gln Leu Thr Val
545                 550                 555                 560 tgg ggc att aaa cag ctc cag gca aga gtc ctg gct gtg gaa aga tac    1728
Trp Gly Ile Lys Gln Leu Gln Ala Arg Val Leu Ala Val Glu Arg Tyr
                565                 570                 575 cta aag gat caa cgg ctc cta ggg att tgg ggc tgc tct gga aaa ctc    1776
Leu Lys Asp Gln Arg Leu Leu Gly Ile Trp Gly Cys Ser Gly Lys Leu
            580                 585                 590 atc tgc acc act aat gta ccc tgg aac tct agt tgg agt aat aaa tct    1824
Ile Cys Thr Thr Asn Val Pro Trp Asn Ser Ser Trp Ser Asn Lys Ser
        595                 600                 605 cag acg gag att tgg ggg aac atg acc tgg atg gag tgg gaa aaa gag    1872
Gln Thr Glu Ile Trp Gly Asn Met Thr Trp Met Glu Trp Glu Lys Glu
    610                 615                 620 att agc aat tac tca aat gaa ata tac agg tta att gaa cta tcg cag    1920
Ile Ser Asn Tyr Ser Asn Glu Ile Tyr Arg Leu Ile Glu Leu Ser Gln
625                 630                 635                 640 aac cag cag gaa aag aat gaa caa gaa tta ttg gca ttg gac aag tgg    1968
Asn Gln Gln Glu Lys Asn Glu Gln Glu Leu Leu Ala Leu Asp Lys Trp
                645                 650                 655 gca agt ctg tgg aat tgg ttt gac ata tca cac tgg ctg tgg tat ata    2016
Ala Ser Leu Trp Asn Trp Phe Asp Ile Ser His Trp Leu Trp Tyr Ile
            660                 665                 670 aaa ata ttt ata atg ata gta gga ggc ttg ata ggc tta aga ata att    2064
Lys Ile Phe Ile Met Ile Val Gly Gly Leu Ile Gly Leu Arg Ile Ile
        675                 680                 685 ttt gct gtg ctt tct ata gta aat aga gtt agg aag gga tac tca cct    2112
Phe Ala Val Leu Ser Ile Val Asn Arg Val Arg Lys Gly Tyr Ser Pro
    690                 695                 700 ttg tca tta cag acc ctt atc cca agc ccg agg gga ccc gcc agg ccc    2160
Leu Ser Leu Gln Thr Leu Ile Pro Ser Pro Arg Gly Pro Ala Arg Pro
705                 710                 715                 720 gaa gga atc gaa gaa gga gat gga gag gaa gac aaa gac aga tcc gtg    2208
Glu Gly Ile Glu Glu Gly Asp Gly Glu Glu Asp Lys Asp Arg Ser Val
                725                 730                 735 aga tta gtg aac gga ttc tta gct ctt gtc tgg gac gac ttg agg aac    2256
Arg Leu Val Asn Gly Phe Leu Ala Leu Val Trp Asp Asp Leu Arg Asn
            740                 745                 750 ctg tgc ctc ttc agc tac cgc cac ttg aga gac ttc ata tta att gca    2304
Leu Cys Leu Phe Ser Tyr Arg His Leu Arg Asp Phe Ile Leu Ile Ala
        755                 760                 765 gcg agg att atg gac agg ggg ctg acg agg ggg tgg gaa gcc ctc aaa    2352
Ala Arg Ile Met Asp Arg Gly Leu Thr Arg Gly Trp Glu Ala Leu Lys
    770                 775                 780 tat ctg tgg aac ctc acg cag tat tgg agt cgg gaa cta aag aat agt    2400
Tyr Leu Trp Asn Leu Thr Gln Tyr Trp Ser Arg Glu Leu Lys Asn Ser
785                 790                 795                 800 gct att agc ttg ttt gat acc aca gca ata ata gta gct gaa gga aca    2448
Ala Ile Ser Leu Phe Asp Thr Thr Ala Ile Ile Val Ala Glu Gly Thr
                805                 810                 815 gat aga gtt ata gaa gct ttg caa aga gct ggt aga gct gtt ctc amc    2496
Asp Arg Val Ile Glu Ala Leu Gln Arg Ala Gly Arg Ala Val Leu Xaa
            820                 825                 830 gta cct aga aga ata aga cag ggc tta gaa agg gct ttg cta taa        2541
Val Pro Arg Arg Ile Arg Gln Gly Leu Glu Arg Ala Leu Leu
        835                 840                 845

<210> SEQ ID NO 47
```

```
<211> LENGTH: 846
<212> TYPE: PRT
<213> ORGANISM: Human immunodeficiency virus type 1
<220> FEATURE:
<221> NAME/KEY: misc_feature
<222> LOCATION: (100)..(100)
<223> OTHER INFORMATION: The 'Xaa' at location 100 stands for Val.
<220> FEATURE:
<221> NAME/KEY: misc_feature
<222> LOCATION: (832)..(832)
<223> OTHER INFORMATION: The 'Xaa' at location 832 stands for Asn, or
      Thr.

<400> SEQUENCE: 47
```

Met Arg Val Arg Gly Met Gln Arg Asn Trp Gln His Leu Gly Lys Trp
1               5                   10                  15

Gly Leu Leu Phe Leu Gly Ile Leu Ile Ile Cys Asn Ala Ala Asp Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Gly Tyr Glu Lys Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Xaa Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Ser Cys Asn Asn Val Asn Gly Thr Ala Thr Asp Gln Asn Ser Thr Leu
130                 135                 140

Lys Glu Glu Ser Gly Ala Ile Gln Asn Cys Ser Phe Asn Met Thr Thr
145                 150                 155                 160

Glu Val Arg Asp Lys Lys Leu Gln Val His Ala Leu Phe Tyr Arg Leu
                165                 170                 175

Asp Ile Val Pro Ile Ser Asn Ser Asn Gly Ser Asp Gly Asn Arg Glu
            180                 185                 190

Tyr Arg Leu Ile Asn Cys Asn Thr Ser Thr Ile Lys Gln Ala Cys Pro
        195                 200                 205

Lys Val Ser Trp Asp Pro Ile Pro Ile His Tyr Cys Ala Pro Ala Gly
    210                 215                 220

Tyr Ala Ile Leu Lys Cys Asn Asn Lys Lys Phe Asn Gly Thr Gly Pro
225                 230                 235                 240

Cys Gln Asn Val Ser Thr Val Gln Cys Thr His Gly Ile Lys Pro Val
                245                 250                 255

Val Ser Thr Gln Leu Leu Leu Asn Gly Ser Leu Ala Glu Glu Ser Ile
            260                 265                 270

Ile Ile Arg Ser Gln Asn Ile Ser Asp Asn Thr Lys Thr Ile Ile Val
        275                 280                 285

His Leu Asn Glu Ser Val Gln Ile Asn Cys Thr Arg Pro Asn Asn Asn
    290                 295                 300

Thr Arg Lys Gly Ile His Leu Gly Pro Gly Gln Ala Phe Tyr Ala Thr
305                 310                 315                 320

Gly Asp Ile Ile Gly Asp Ile Arg Lys Ala His Cys Asn Ile Ser Arg
                325                 330                 335

Ile Gln Trp Ser Asn Thr Leu Glu Gln Val Lys Ala Glu Leu Lys Pro
            340                 345                 350

```
His Phe Asn Asn Lys Thr Ile Glu Phe Glu Pro Pro Ser Pro Gly Gly
        355                 360                 365
Asp Leu Glu Ile Thr Met His Ser Phe Asn Cys Arg Gly Glu Phe Phe
        370                 375                 380
Tyr Cys Asn Thr Ser Gly Leu Phe Asn Thr Thr Glu Ser Asn Glu Thr
385                 390                 395                 400
Ile Val Val Leu Pro Cys Lys Ile Lys Gln Ile Val Arg Met Trp Gln
                405                 410                 415
Gly Val Gly Gln Ala Met Tyr Ala Pro Pro Ile Ala Gly Asn Ile Thr
            420                 425                 430
Cys Asn Ser Asn Ile Thr Gly Leu Leu Leu Thr Arg Asp Gly Gly Gln
        435                 440                 445
His Asn Asp Ser Asn Thr Thr Glu Thr Phe Arg Pro Gly Gly Gly Asp
        450                 455                 460
Met Arg Asp Asn Trp Arg Ser Glu Leu Tyr Lys Tyr Lys Val Val Glu
465                 470                 475                 480
Ile Glu Pro Leu Gly Val Ala Pro Thr Arg Ala Lys Arg Gln Val Val
                485                 490                 495
Lys Arg Glu Lys Arg Ala Val Gly Ile Gly Ala Leu Phe Leu Gly Phe
            500                 505                 510
Leu Gly Ala Ala Gly Ser Thr Met Gly Ala Ala Ser Ile Thr Leu Thr
        515                 520                 525
Val Gln Ala Arg Gln Leu Leu Ser Gly Ile Val Gln Gln Gln Asn Asn
        530                 535                 540
Leu Leu Arg Ala Ile Glu Ala Gln Gln His Leu Leu Gln Leu Thr Val
545                 550                 555                 560
Trp Gly Ile Lys Gln Leu Gln Ala Arg Val Leu Ala Val Glu Arg Tyr
                565                 570                 575
Leu Lys Asp Gln Arg Leu Leu Gly Ile Trp Gly Cys Ser Gly Lys Leu
            580                 585                 590
Ile Cys Thr Thr Asn Val Pro Trp Asn Ser Ser Trp Ser Asn Lys Ser
        595                 600                 605
Gln Thr Glu Ile Trp Gly Asn Met Thr Trp Met Glu Trp Glu Lys Glu
        610                 615                 620
Ile Ser Asn Tyr Ser Asn Glu Ile Tyr Arg Leu Ile Glu Leu Ser Gln
625                 630                 635                 640
Asn Gln Gln Glu Lys Asn Glu Gln Glu Leu Leu Ala Leu Asp Lys Trp
                645                 650                 655
Ala Ser Leu Trp Asn Trp Phe Asp Ile Ser His Trp Leu Trp Tyr Ile
            660                 665                 670
Lys Ile Phe Ile Met Ile Val Gly Gly Leu Ile Gly Leu Arg Ile Ile
        675                 680                 685
Phe Ala Val Leu Ser Ile Val Asn Arg Val Arg Lys Gly Tyr Ser Pro
        690                 695                 700
Leu Ser Leu Gln Thr Leu Ile Pro Ser Pro Arg Gly Pro Ala Arg Pro
705                 710                 715                 720
Glu Gly Ile Glu Glu Gly Asp Gly Glu Asp Lys Asp Arg Ser Val
                725                 730                 735
Arg Leu Val Asn Gly Phe Leu Ala Leu Val Trp Asp Asp Leu Arg Asn
            740                 745                 750
Leu Cys Leu Phe Ser Tyr Arg His Leu Arg Asp Phe Ile Leu Ile Ala
        755                 760                 765
Ala Arg Ile Met Asp Arg Gly Leu Thr Arg Gly Trp Glu Ala Leu Lys
```

```
                  770                 775                 780
Tyr Leu Trp Asn Leu Thr Gln Tyr Trp Ser Arg Glu Leu Lys Asn Ser
785                 790                 795                 800

Ala Ile Ser Leu Phe Asp Thr Thr Ala Ile Ile Val Ala Glu Gly Thr
                805                 810                 815

Asp Arg Val Ile Glu Ala Leu Gln Arg Ala Gly Arg Ala Val Leu Xaa
            820                 825                 830

Val Pro Arg Arg Ile Arg Gln Gly Leu Glu Arg Ala Leu Leu
            835                 840                 845

<210> SEQ ID NO 48
<211> LENGTH: 2562
<212> TYPE: DNA
<213> ORGANISM: Human immunodeficiency virus type 1
<220> FEATURE:
<221> NAME/KEY: CDS
<222> LOCATION: (1)..(2562)

<400> SEQUENCE: 48 atg aga gtg agg ggg atg cag agg aat tgg cag cac ttg ggg aaa tgg      48
Met Arg Val Arg Gly Met Gln Arg Asn Trp Gln His Leu Gly Lys Trp
1               5                  10                  15 ggc ctt tta ttc ctg gga ata tta ata atc cgt aat gct gca gac aac      96
Gly Leu Leu Phe Leu Gly Ile Leu Ile Ile Arg Asn Ala Ala Asp Asn
            20                  25                  30 ttg tgg gtc aca gtc tat tat ggg gta cct gtg tgg aaa gaa gca acc     144
Leu Trp Val Thr Val Tyr Tyr Gly Val Pro Val Trp Lys Glu Ala Thr
        35                  40                  45 act act cta ttt tgt gca tca gat gct aaa gga tat gag aaa gag gta     192
Thr Thr Leu Phe Cys Ala Ser Asp Ala Lys Gly Tyr Glu Lys Glu Val
    50                  55                  60 cat aat gtc tgg gct aca cat gcc tgt gta ccc aca gac ccc aac cca     240
His Asn Val Trp Ala Thr His Ala Cys Val Pro Thr Asp Pro Asn Pro
65                  70                  75                  80 caa gaa gta gtc ctg aaa aat gta aca gaa aat ttt aat atg tgg aaa     288
Gln Glu Val Val Leu Lys Asn Val Thr Glu Asn Phe Asn Met Trp Lys
                85                  90                  95 aat aac atg gta gaa caa atg cat gaa gat ata atc agt tta tgg gat     336
Asn Asn Met Val Glu Gln Met His Glu Asp Ile Ile Ser Leu Trp Asp
            100                 105                 110 caa agc cta aag cca tgt gta aag cta acc cca ctc tgt gtt act tta     384
Gln Ser Leu Lys Pro Cys Val Lys Leu Thr Pro Leu Cys Val Thr Leu
        115                 120                 125 aac tgt act gat ttc aat ggc aat acc act gat caa aac agc acc ctg     432
Asn Cys Thr Asp Phe Asn Gly Asn Thr Thr Asp Gln Asn Ser Thr Leu
    130                 135                 140 aag gaa gag tca gga gca ata caa gac tgt tct ttc aat atg acc aca     480
Lys Glu Glu Ser Gly Ala Ile Gln Asp Cys Ser Phe Asn Met Thr Thr
145                 150                 155                 160 gaa gta aga gat aag gag ctg caa gta cat gca ctt ttt tat aga ctt     528
Glu Val Arg Asp Lys Glu Leu Gln Val His Ala Leu Phe Tyr Arg Leu
                165                 170                 175 gat ata gtg cca atc agc ggt agc aat gat agt agt ggc aat ggg aaa     576
Asp Ile Val Pro Ile Ser Gly Ser Asn Asp Ser Ser Gly Asn Gly Lys
            180                 185                 190 tat agg cta ata aat tgt aat acc tca acc att aaa cag gct tgt cca     624
Tyr Arg Leu Ile Asn Cys Asn Thr Ser Thr Ile Lys Gln Ala Cys Pro
        195                 200                 205 aag gta tct tgg gat cca att ccc ata cat tat tgt gct ccg gct ggt     672
Lys Val Ser Trp Asp Pro Ile Pro Ile His Tyr Cys Ala Pro Ala Gly
    210                 215                 220
```

-continued

```
tat gcg att cta aaa tgt aat gat aaa aag ttc aat ggg aca ggg cca        720
Tyr Ala Ile Leu Lys Cys Asn Asp Lys Lys Phe Asn Gly Thr Gly Pro
225                 230                 235                 240 tgc cgg aat gtc agc aca gta caa tgt aca cat ggc att aag cca gtg        768
Cys Arg Asn Val Ser Thr Val Gln Cys Thr His Gly Ile Lys Pro Val
            245                 250                 255 gta tca act cag ttg ctg tta aat ggc agc cta gca gaa gaa agt ata        816
Val Ser Thr Gln Leu Leu Leu Asn Gly Ser Leu Ala Glu Glu Ser Ile
        260                 265                 270 ata ata aga tct caa aat atc tca gat aat aca aaa act ata ata gta        864
Ile Ile Arg Ser Gln Asn Ile Ser Asp Asn Thr Lys Thr Ile Ile Val
    275                 280                 285 cac ctt aat gaa tct ata cag att aat tgt aca aga ccc aac aac agt        912
His Leu Asn Glu Ser Ile Gln Ile Asn Cys Thr Arg Pro Asn Asn Ser
290                 295                 300 aca aga aaa ggt ata cat ata gga cca gga caa gca ttc tat gca aca        960
Thr Arg Lys Gly Ile His Ile Gly Pro Gly Gln Ala Phe Tyr Ala Thr
305                 310                 315                 320 ggt gaa ata ata ggg gat ata aga aag gca cat tgt aac att agt aga       1008
Gly Glu Ile Ile Gly Asp Ile Arg Lys Ala His Cys Asn Ile Ser Arg
            325                 330                 335 gga caa tgg agg aaa act cta aaa caa gta gaa gca gag tta aag cct       1056
Gly Gln Trp Arg Lys Thr Leu Lys Gln Val Glu Ala Glu Leu Lys Pro
        340                 345                 350 cat ttt aat aat aat aca ata gaa ttt aaa cca cca ccc cca gga gga       1104
His Phe Asn Asn Asn Thr Ile Glu Phe Lys Pro Pro Pro Pro Gly Gly
    355                 360                 365 gat cta gaa att aca atg cat agt ttt aat tgt aga gga gaa ttt ttc       1152
Asp Leu Glu Ile Thr Met His Ser Phe Asn Cys Arg Gly Glu Phe Phe
370                 375                 380 tac tgc aat aca tca gga ctg ttt aat act aat aca tca gga cag ttt       1200
Tyr Cys Asn Thr Ser Gly Leu Phe Asn Thr Asn Thr Ser Gly Gln Phe
385                 390                 395                 400 aat acc aca gga tcc aat gaa act ata gtt ctc cca tgt aaa atg aaa       1248
Asn Thr Thr Gly Ser Asn Glu Thr Ile Val Leu Pro Cys Lys Met Lys
            405                 410                 415 caa att gta aga atg tgg cag gga gta aga caa gca atg tat gct cct       1296
Gln Ile Val Arg Met Trp Gln Gly Val Arg Gln Ala Met Tyr Ala Pro
        420                 425                 430 ccc att gca gga aat att acc tgt aac tca aat att aca ggc cta ctg       1344
Pro Ile Ala Gly Asn Ile Thr Cys Asn Ser Asn Ile Thr Gly Leu Leu
    435                 440                 445 tta aca aga gat ggt ggt aat agt agt aat gct aat gct aat gag acc       1392
Leu Thr Arg Asp Gly Gly Asn Ser Ser Asn Ala Asn Ala Asn Glu Thr
450                 455                 460 ttc aga cct ggg gga gga gat atg aga gac aat tgg aga agt gaa cta       1440
Phe Arg Pro Gly Gly Gly Asp Met Arg Asp Asn Trp Arg Ser Glu Leu
465                 470                 475                 480 tat aaa tat aaa gta gta gaa att gaa cca cta gga gta gca ccc acc       1488
Tyr Lys Tyr Lys Val Val Glu Ile Glu Pro Leu Gly Val Ala Pro Thr
            485                 490                 495 ggg gca aaa aga caa gtg gtg aag aga gaa aaa aga gca gtg gga atg       1536
Gly Ala Lys Arg Gln Val Val Lys Arg Glu Lys Arg Ala Val Gly Met
        500                 505                 510 gga gct ttg ttc ctt ggg ttc ttg gga gca gca gga agc act atg ggc       1584
Gly Ala Leu Phe Leu Gly Phe Leu Gly Ala Ala Gly Ser Thr Met Gly
    515                 520                 525 gcg gcg tca ata acg ctg acg gta cag gcc aga cag tta ttg tct gga       1632
Ala Ala Ser Ile Thr Leu Thr Val Gln Ala Arg Gln Leu Leu Ser Gly
530                 535                 540
```

```
ata gtg caa cag caa aac aat ttg ctg agg gct att gaa gcg caa cag    1680
Ile Val Gln Gln Gln Asn Asn Leu Leu Arg Ala Ile Glu Ala Gln Gln
545                 550                 555                 560 cat ctg ttg cag ctc aca gtc tgg ggc att aaa cag ctc cag gca aga    1728
His Leu Leu Gln Leu Thr Val Trp Gly Ile Lys Gln Leu Gln Ala Arg
                565                 570                 575 gtc ctg gct gtg gaa aga tac ctc agg gat caa cag ctc cta ggg ctt    1776
Val Leu Ala Val Glu Arg Tyr Leu Arg Asp Gln Gln Leu Leu Gly Leu
            580                 585                 590 tgg ggc tgc tct gga aaa ctc atc tgc acc act aat gta ccc tgg aac    1824
Trp Gly Cys Ser Gly Lys Leu Ile Cys Thr Thr Asn Val Pro Trp Asn
595                 600                 605 tct agt tgg agt aat aaa tct cag gag gag att tgg gag aac atg acc    1872
Ser Ser Trp Ser Asn Lys Ser Gln Glu Glu Ile Trp Glu Asn Met Thr
610                 615                 620 tgg atg gag tgg gaa aga gag att agc aat tac tca gat gaa ata tac    1920
Trp Met Glu Trp Glu Arg Glu Ile Ser Asn Tyr Ser Asp Glu Ile Tyr
625                 630                 635                 640 agg tta att gaa cta tcg cag aac cag cag gaa aag aat gaa caa gaa    1968
Arg Leu Ile Glu Leu Ser Gln Asn Gln Gln Glu Lys Asn Glu Gln Glu
                645                 650                 655 tta ttg aca ttg gac aaa tgg gca agt ctg tgg aat tgg ttt gac ata    2016
Leu Leu Thr Leu Asp Lys Trp Ala Ser Leu Trp Asn Trp Phe Asp Ile
            660                 665                 670 tca cac tgg ctg tgg tat ata aga ata ttt ata atg ata gta gga ggc    2064
Ser His Trp Leu Trp Tyr Ile Arg Ile Phe Ile Met Ile Val Gly Gly
        675                 680                 685 ttg ata ggc tta aga ata att ttt gct gtg ctt tct ata gta aat aga    2112
Leu Ile Gly Leu Arg Ile Ile Phe Ala Val Leu Ser Ile Val Asn Arg
690                 695                 700 gtt agg aag gga tac tca cct gtg tca tta cag acc ctt atc cca agc    2160
Val Arg Lys Gly Tyr Ser Pro Val Ser Leu Gln Thr Leu Ile Pro Ser
705                 710                 715                 720 ccg agg gaa ccc gcc agg ccc gaa gga atc gaa gaa gga gat gga gag    2208
Pro Arg Glu Pro Ala Arg Pro Glu Gly Ile Glu Glu Gly Asp Gly Glu
                725                 730                 735 gaa gac aaa gac aga tcc gtg aga tta gtg aac gga ttc tta gct ctt    2256
Glu Asp Lys Asp Arg Ser Val Arg Leu Val Asn Gly Phe Leu Ala Leu
            740                 745                 750 gtc tgg gac gac ttg agg aac ctg tgc ctc ttc agc tac cgc cgc ttg    2304
Val Trp Asp Asp Leu Arg Asn Leu Cys Leu Phe Ser Tyr Arg Arg Leu
        755                 760                 765 aga gac ttc ata tta att gca gcg agg att gtg gac agg ggg ctg acg    2352
Arg Asp Phe Ile Leu Ile Ala Ala Arg Ile Val Asp Arg Gly Leu Thr
770                 775                 780 agg ggg tgg gaa gcc ctc aaa tac ctg tgg aac ctt gcg cag tat tgg    2400
Arg Gly Trp Glu Ala Leu Lys Tyr Leu Trp Asn Leu Ala Gln Tyr Trp
785                 790                 795                 800 agt cgg gaa cta aag aat agt gct att agc ttg ttt gat acc ata gca    2448
Ser Arg Glu Leu Lys Asn Ser Ala Ile Ser Leu Phe Asp Thr Ile Ala
                805                 810                 815 ata ata gta gct gaa gga aca gat aga gtt ata gaa gct tta caa aga    2496
Ile Ile Val Ala Glu Gly Thr Asp Arg Val Ile Glu Ala Leu Gln Arg
            820                 825                 830 gct ggt aga gct gtt ctc aac gta cct aga aga ata aga cag ggc tta    2544
Ala Gly Arg Ala Val Leu Asn Val Pro Arg Arg Ile Arg Gln Gly Leu
        835                 840                 845 gaa agg gct ttg cta taa                                            2562
Glu Arg Ala Leu Leu
            850
```

<210> SEQ ID NO 49
<211> LENGTH: 853
<212> TYPE: PRT
<213> ORGANISM: Human immunodeficiency virus type 1

<400> SEQUENCE: 49

```
Met Arg Val Arg Gly Met Gln Arg Asn Trp Gln His Leu Gly Lys Trp
1               5                   10                  15
Gly Leu Leu Phe Leu Gly Ile Leu Ile Ile Arg Asn Ala Ala Asp Asn
            20                  25                  30
Leu Trp Val Thr Val Tyr Tyr Gly Val Pro Val Trp Lys Glu Ala Thr
        35                  40                  45
Thr Thr Leu Phe Cys Ala Ser Asp Ala Lys Gly Tyr Glu Lys Glu Val
50                  55                  60
His Asn Val Trp Ala Thr His Ala Cys Val Pro Thr Asp Pro Asn Pro
65                  70                  75                  80
Gln Glu Val Val Leu Lys Asn Val Thr Glu Asn Phe Asn Met Trp Lys
                85                  90                  95
Asn Asn Met Val Glu Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Asn Cys Thr Asp Phe Asn Gly Asn Thr Thr Asp Gln Asn Ser Thr Leu
130                 135                 140
Lys Glu Glu Ser Gly Ala Ile Gln Asp Cys Ser Phe Asn Met Thr Thr
145                 150                 155                 160
Glu Val Arg Asp Lys Glu Leu Gln Val His Ala Leu Phe Tyr Arg Leu
                165                 170                 175
Asp Ile Val Pro Ile Ser Gly Ser Asn Asp Ser Ser Gly Asn Gly Lys
            180                 185                 190
Tyr Arg Leu Ile Asn Cys Asn Thr Ser Thr Ile Lys Gln Ala Cys Pro
        195                 200                 205
Lys Val Ser Trp Asp Pro Ile Pro Ile His Tyr Cys Ala Pro Ala Gly
210                 215                 220
Tyr Ala Ile Leu Lys Cys Asn Asp Lys Lys Phe Asn Gly Thr Gly Pro
225                 230                 235                 240
Cys Arg Asn Val Ser Thr Val Gln Cys Thr His Gly Ile Lys Pro Val
                245                 250                 255
Val Ser Thr Gln Leu Leu Leu Asn Gly Ser Leu Ala Glu Glu Ser Ile
            260                 265                 270
Ile Ile Arg Ser Gln Asn Ile Ser Asp Asn Thr Lys Thr Ile Ile Val
        275                 280                 285
His Leu Asn Glu Ser Ile Gln Ile Asn Cys Thr Arg Pro Asn Asn Ser
290                 295                 300
Thr Arg Lys Gly Ile His Ile Gly Pro Gly Gln Ala Phe Tyr Ala Thr
305                 310                 315                 320
Gly Glu Ile Ile Gly Asp Ile Arg Lys Ala His Cys Asn Ile Ser Arg
                325                 330                 335
Gly Gln Trp Arg Lys Thr Leu Lys Gln Val Glu Ala Glu Leu Lys Pro
            340                 345                 350
His Phe Asn Asn Asn Thr Ile Glu Phe Lys Pro Pro Pro Gly Gly
        355                 360                 365
Asp Leu Glu Ile Thr Met His Ser Phe Asn Cys Arg Gly Glu Phe Phe
370                 375                 380
```

```
Tyr Cys Asn Thr Ser Gly Leu Phe Asn Thr Asn Thr Ser Gly Gln Phe
385                 390                 395                 400

Asn Thr Thr Gly Ser Asn Glu Thr Ile Val Leu Pro Cys Lys Met Lys
            405                 410                 415

Gln Ile Val Arg Met Trp Gln Gly Val Arg Gln Ala Met Tyr Ala Pro
            420                 425                 430

Pro Ile Ala Gly Asn Ile Thr Cys Asn Ser Asn Ile Thr Gly Leu Leu
            435                 440                 445

Leu Thr Arg Asp Gly Gly Asn Ser Asn Ala Asn Ala Asn Glu Thr
        450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Glu Pro Leu Gly Val Ala Pro Thr
                485                 490                 495

Gly Ala Lys Arg Gln Val Val Lys Arg Glu Lys Arg Ala Val Gly Met
            500                 505                 510

Gly Ala Leu Phe Leu Gly Phe Leu Gly Ala Ala Gly Ser Thr Met Gly
            515                 520                 525

Ala Ala Ser Ile Thr Leu Thr Val Gln Ala Arg Gln Leu Leu Ser Gly
        530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
            565                 570                 575

Val Leu Ala Val Glu Arg Tyr Leu Arg Asp Gln Gln Leu Leu Gly Leu
            580                 585                 590

Trp Gly Cys Ser Gly Lys Leu Ile Cys Thr Thr Asn Val Pro Trp Asn
            595                 600                 605

Ser Ser Trp Ser Asn Lys Ser Gln Glu Glu Ile Trp Glu Asn Met Thr
        610                 615                 620

Trp Met Glu Trp Glu Arg Glu Ile Ser Asn Tyr Ser Asp Glu Ile Tyr
625                 630                 635                 640

Arg Leu Ile Glu Leu Ser Gln Asn Gln Gln Glu Lys Asn Glu Gln Glu
                645                 650                 655

Leu Leu Thr Leu Asp Lys Trp Ala Ser Leu Trp Asn Trp Phe Asp Ile
            660                 665                 670

Ser His Trp Leu Trp Tyr Ile Arg Ile Phe Ile Met Ile Val Gly Gly
            675                 680                 685

Leu Ile Gly Leu Arg Ile Ile Phe Ala Val Leu Ser Ile Val Asn Arg
690                 695                 700

Val Arg Lys Gly Tyr Ser Pro Val Ser Leu Gln Thr Leu Ile Pro Ser
705                 710                 715                 720

Pro Arg Glu Pro Ala Arg Pro Glu Gly Ile Glu Glu Gly Asp Gly Glu
            725                 730                 735

Glu Asp Lys Asp Arg Ser Val Arg Leu Val Asn Gly Phe Leu Ala Leu
            740                 745                 750

Val Trp Asp Asp Leu Arg Asn Leu Cys Leu Phe Ser Tyr Arg Arg Leu
        755                 760                 765

Arg Asp Phe Ile Leu Ile Ala Ala Arg Ile Val Asp Arg Gly Leu Thr
770                 775                 780

Arg Gly Trp Glu Ala Leu Lys Tyr Leu Trp Asn Leu Ala Gln Tyr Trp
785                 790                 795                 800

Ser Arg Glu Leu Lys Asn Ser Ala Ile Ser Leu Phe Asp Thr Ile Ala
```

```
                    805                 810                 815
Ile Ile Val Ala Glu Gly Thr Asp Arg Val Ile Glu Ala Leu Gln Arg
                820                 825                 830

Ala Gly Arg Ala Val Leu Asn Val Pro Arg Arg Ile Arg Gln Gly Leu
        835                 840                 845

Glu Arg Ala Leu Leu
    850

<210> SEQ ID NO 50
<211> LENGTH: 2562
<212> TYPE: DNA
<213> ORGANISM: Human immunodeficiency virus type 1

<400> SEQUENCE: 50
atgagagtga ggggatgca gaggaattgg cagcacttgg ggaaatgggg ccttttattc     60
ctggggatat aataatctg taatgctgca gacaacttgt gggtcacagt ctattatggg    120
gtacctgtgt ggaaagaagc aaccactact ctatttttgtg catcagatgc caaaggatat   180
gagaaagagg tacataatgt ctgggctaca catgcctgtg tacccacaga ccccaaccca   240
caagaagtag ttctgaaaaa tgtaacagaa aatttttaata tgtggaaaaa taacatggta   300
gaacaaatgc atgaagatat aatcagttta tgggatcaaa gcctaaagcc atgtgtaaag   360
ctaaccccac tctgtgttac tttaaactgt actgatttca atggcaatac cactgatcaa   420
aacagcaccc tgaaggaaga gtcaggagca atacaagact gttctttcaa tatgaccaca   480
gaagtaagag ataaggagct gcaagtacat gcacttttt atagacttga tatagtgcca   540
atcagcggta gcaatgatag tagtggcaat gggaaatata ggctaataaa ttgtaatacc   600
tcaaccatta gacaggcttg tccaaaggta tcttgggatc caattcccat acattattgt   660
gctccggctg gttatgcgat tctaaaatgt aatgataaaa agttcaatgg gacagggcca   720
tgccagaatg tcagcacagt acaatgtaca catggcatta agccagtggt atcaactcag   780
ttgctgttaa atggcagcct agcagaagaa agtataataa taagatctca aaatatctca   840
gataatacaa aaactataat agtacacctt aatgaatcta tacagattaa ttgtacaaga   900
cccaacaaca atacaagaaa aggtatacat ataggaccag acaagcatt ctatgcaaca    960 ggtgaaataa tagggatat aagaaaggca cattgtaaca ttagtagagg acaatggagg   1020
aaaactctaa acaagtaga agcagagtta aagcctcatt ttaataataa tacaatagaa   1080
tttaaaccac cacccccagg aggagatcta gaaattacaa tgcatagttt taattgtaga   1140 ggagaattttt tctactgcaa tacatcagga ctgtttaata ctaatacatc aggacagttt   1200
aataccacag gatccaatga aactatagtt ctcccatgta aaataaaaca aattgtaaga   1260
atgtggcagg gagtaggaca agcaatgtat gctcctccca ttgcaggaaa tattacctgt   1320
aactcaaata ttacaggcct actgttaaca agagatggtg gtaatagtag taatgctaat   1380
gctaatgaga ccttcagacc tggggaagga gatatgagag acaattggag aagtgaacta   1440 tataatatata agtagtaga aattgaacca ctaggagtag cacccaccgg ggcaaaaaga   1500
caagtggtga gagagaaaa aagagcagtg ggaatggag ctttgttcct tgggttcttg    1560
ggagcagcag gaagcactat gggcgcggcg tcaataacgc tgacggtaca ggccagacaa   1620
ttattgtctg gaatagtgca acagcaaaac aatttgctga ggctattga gcgcaacag    1680 catctgttgc agctcacagt ctggggcatt aaacagctcc aggcaagagt cctggctgtg   1740
gaaagatacc tcaggatca acagctccta gggctttggg gctgctctgg aaaactcatc   1800
tgcaccacta atgtaccctg gaactctagt tggagtaata atctcaggta ggagatttgg   1860
```

```
gagaacatga cctggatgga gtgggaaaga gagattagca attactcaga tgaaatatac   1920
aggttaattg aactatcgca gaaccagcag gaaaagaatg aacaagaatt attgacattg   1980
gacaaatggg caagtctgtg gaattggttt gacatatcac actggctgtg gtatataaga   2040
atatttataa tgatagtagg aggcttgata ggcttaagaa taattttttgc tgtgctttct   2100 atagtaaata gagttaggaa gggatactca cctgtgtcat tacagaccct tatcccaagc   2160
ccgagggaac ccgccaggcc cgaaggaatc gaagaaggag atggagagga agacaaagac   2220
agatccgtga gattagtgaa cggattctta gctcttgtct gggacgactt gaggaacctg   2280
tgcctcttca gctaccgccg cttgagagac ttcatattaa ttgcagcgag gattgtggac   2340
agggggctga cgaggggtg ggaagccctc aaatacctgt ggaaccttgc gcagtattgg   2400
agtcgggaac taaagaatag tgctattagc ttgtttgata ccatagcaat aatagtagct   2460
gaaggaacag atagagttat agaagctttg caaagagctg gtagagctgt tctcaacgta   2520
cctagaagaa taagacaggg cttagaaagg gctttgctat aa                      2562
```

<210> SEQ ID NO 51
<211> LENGTH: 2571
<212> TYPE: DNA
<213> ORGANISM: Human immunodeficiency virus type 1

<400> SEQUENCE: 51

```
atgagagtga tggggataca gaggaactat ccactcttat ggagatgggg tatgacaata    60
ttttggttaa tgatgatttg taatgctgaa aatttgtggg tcacggtcta ctatggggta   120
cctgtgtgga aagacgcaaa gaccacccta ttttgtgcat cagatgctaa agcatatgat   180
acagaagtac ataatgtttg ggctacacat gcctgtgtac ccacagaccc taacccacaa   240
gaaatggatt tgaaaaatgt aacagaaaat tttaacatgt ggaaaaataa catggtagag   300
cagatgcatg aagatataat tagcctatgg gaccaaagcc taaagccatg tgtacagtta   360 accctctct gcgttacttt agattgtcat aactacaata gcagcaatga caacccccct   420
gggcaagagg taaaaaactg ctcttttcaat atgaccacag aactaagaga taagagacag   480
aaagtgtatg cacttttttta taaaattgat gtagtaccac ttagtaatag tagtaacagt   540
agtcaatata gtttaataaa ttgtaatacc tcagccatta cacaagcttg tccaaaggta   600
tcctttgatc caattcccat acattattgt gctccagctg gttttgcaat tctaaagtgt   660
aaggataaga agttcaatgg agcagggcca tgcaataatg tcagcacagt acaatgcaca   720
catggaatca agccagtagt atcaactcaa ctgctgttaa acggcagtct agcagaagga   780
gaggtagtga tcagatctga aaatatctca aacaatgcca aaaccataat agtacagttg   840
gttgagccta taagaattaa ttgtaccaga cctggcaaca atacaagaaa aagtgtacgt   900
ataggaccag gcaaacatt ctatgcaaat gaggtaatag ggaatataag acaagcacat   960
tgtaatgtca gtagatcaga ctggaataaa actttacaac aggtagctgt acaattaggg  1020
aagcaatttg agaataaaac aataatcttt aagaacact caggagggga tgtagaaatt  1080
acaacacata gttttaattg tagaggagaa ttttttctatt gcaatacacc gatactgttt  1140
aatagcacct gggagtacaa tagcacttgg ggtaactata gctcaaatta cacagggtca  1200
aatgacatta taactctcca atgcaaaata aagcaaattg taaatatgtg gcagaaagta  1260
ggacaagcaa tgtatgcccc tcccatccca ggagagttaa ggtgtgaatc aaacattaca  1320
ggattattat taacaaggga tggagggact aatagtacaa atgagacttt cgagactttt  1380
aggcctggag gaggagacat gagggacaat tggagaagtg aattatataa gtataaggta  1440
```

| | |
|---|---|
| gtaaaaattg aaccactagg tgtggcaccc acccatgcaa aaagaagagt ggtgcagaga | 1500 |
| gaaaaaagag cagttggact gggagctgtc ttccttgggt tcttaggagc agcaggaagc | 1560 |
| actatgggcg cggcgtcaat aacgctgacg gtacaggcca gacaattatt gtccggtata | 1620 |
| gtgcaacagc agaacaattt gctgagggct atagaggctc aacaacatct gttgaaactc | 1680 |
| acggtctggg gcattaaaca gctccaggca agagtcctgg ctctggaaag atacctaagg | 1740 |
| gatcaacagc tcctaggaat ttggggctgc tctggaaaac tcatctgcac cactactgta | 1800 |
| ccctggaact cgacttggag taataaaact tataaggaaa tatgggataa catgacctgg | 1860 |
| ctggaatggg ataaagaaat tagcaggtac acaaacataa tatatgatct aattgaagaa | 1920 |
| tcgcagaacc agcaggaaaa gaatgaacaa gacttattag cattggacaa atgggcaagt | 1980 |
| ctgtggaatt ggtttaacat atcaaattgg ctatggtata taagaatatt tataatgata | 2040 |
| gtaggaggtt tgataggttt aagaatagtt tttgctgtgc ttgctataat aaatagagtt | 2100 |
| aggcagggat actcaccttt gtctttccag acccttaccc accaacagag ggaacaaccc | 2160 |
| gacagacccg aaagaatcga agaaggaggt ggcgagcaag acagagacag atccgtgcga | 2220 |
| ttagtgagcg ggttcttagc acttgcctgg gacgatctgc ggagcctgtg cctcttcagc | 2280 |
| taccaccgat tgagagactt tgtcttgatt gcaacgagga ctgtggaact tctgggacac | 2340 |
| agcagtctca agggactgag actggggtgg gaagccctca aatatctgtg gagccttctg | 2400 |
| tcatactggg gtcaggaact aaagaatagt gctattagtt tgcttgatac aacagcaata | 2460 |
| gcagtagcta actggacaga cagagttata gaaataggac aaagaattgg tagagctatt | 2520 |
| tggaacatac ctacaagaat cagacagggt atcgaaaggg ctttgctata a | 2571 |

<210> SEQ ID NO 52
<211> LENGTH: 2556
<212> TYPE: DNA
<213> ORGANISM: Human immunodeficiency virus type 1

<400> SEQUENCE: 52

| | |
|---|---|
| atgaaagtga aggagatcag gaagaattgt cggcacttgt ggagatgggg caccatgctc | 60 |
| cttgggatgt tgatgatttg tagtgctaca gaaaaattgt gggtcacagt ctattatggg | 120 |
| gtaccggtat ggaaagaaac agacaccact ttattttgtg catcagatgc taaagcatat | 180 |
| gacagagagg tacataatgt ttgggccaca catgcctgtg tacccacaga ccccaaccca | 240 |
| caagaagtag tattggaaaa tgtgacagaa aattttaaca tgtggaaaaa taacatggta | 300 |
| gaacagatgc aggaggatat aatcagttta tgggatcaaa gcctaaagcc atgtgtaaaa | 360 |
| ttaaccccac tctgtgttac tttaaattgc actgctccga atgttaccaa taccaataat | 420 |
| agtactaata ccaataatag tagtttggac gaaggagaaa tgaaaaactg ctctttcaac | 480 |
| atcaccacaa gcataaaaga taagatacag agagaatatg cacttttta tagacttgat | 540 |
| atagtaccaa tagatggtag taatagcagc tataggttga caaagtgtaa cacctcagtc | 600 |
| attacacagg cctgtccaaa ggtgaccttt gagccaattc ccatacatta ttgtgccccg | 660 |
| gctggttttg cgattctaaa gtgtaacgat aaaaagttca atggaacagg accatgtaaa | 720 |
| aatgtcagca cagtacaatg tacacatgga attaggccag tagtatcaac tcaactgttg | 780 |
| ttaaatggca gtctagcaga agaaggta ataattgat ctgaaaattt ctcggacaat | 840 |
| gctaaaaaca atatagtaca tctaaatgaa tctgtagaaa ttaattgtac aagacccagc | 900 |
| aacaatacaa gaaaaagtat acatatggga ccaggaggca catttatgc aacaggaaaa | 960 |
| ataataggag atataagaca agcacattgt aacattagtg aaaaaaaatg gggagaagct | 1020 |

| | |
|---|---|
| ttagaaagga tagttaaaaa attaagaaaa caatataaca acacaataat ctttactcaa | 1080 |
| ccctcaggag gggacccaga aattgtaatg cacagtttta attgtggagg ggaatttttc | 1140 |
| tactgtaata catcacaact gtttaatact acttggagtg atactactac ttggaataat | 1200 |
| actaacaaca caaatggcaa tatcacactc ccatgcagaa taaaacaaat tataaacatg | 1260 |
| tggcagggag taggaaaagc aatgtatgct cctcccatca gtggacaaat tagatgttca | 1320 |
| tcaaatatta cagggctgat attaacaaga gatggtggtc tcgcgaacag gaccaaagag | 1380 |
| accttcagac ctggaggagg agatatgagg gacaattgga gaagtgaatt atataaaatat | 1440 |
| aaagtagtaa aaattgaacc attaggagta gcacccacca aggcaaagag aagagtggtg | 1500 |
| cagagagaaa aaagagcagt gggaatgcta ggagctgtgt tccttgggtt cttgggagca | 1560 |
| gcaggaagca ctatgggcgc agcgtcaata acgctgacgg tacaggccag acaattattg | 1620 |
| tctggtatag tgcaacagca gaacaatctg ctgaaggcta ttgaggcgca acagcatctg | 1680 |
| ttgcaactca cagtctgggg catcaagcag ctccaggcaa gagtcctggc tgtggaaaga | 1740 |
| tacctacagg atcagcagct cctggggatt tggggttgct ctggaaaact catttgcacc | 1800 |
| actactgtgc cttggaatgc tagttggagt aataaatctc tggaaaagat ttggaataac | 1860 |
| atgacctgga tggagtggga aaaagaaatt gacaattaca caaacttaat atacaccttaa | 1920 |
| attgaagaat cgcagaacca caagaaaaaa atgaacaag aattattgga gttgggcaag | 1980 |
| tgggacagtt tgtggagttg gttcgacata tcacaatggc tgtggtatat aaaaatattc | 2040 |
| ataatgatag taggaggttt ggtaggttta agaatagttt ttgctgtact ttctatagta | 2100 |
| aatagagtta ggcagggata ttcaccatta tcgtttcaga cccgcttccc agccccgagg | 2160 |
| ggacccgaca ggcccgaagg aatcgaagaa gaaggtggag agagacag agacagatcc | 2220 |
| gatcgattag tgaacggatt cttggcactt atctggaacg atctgggcag cctgtgcctc | 2280 |
| ttcagctacc atcgcttgag agacttactc ttgattgcag cgaggattgt ggaacttctg | 2340 |
| ggacgcaggg ggtgggaagt cctcaaatat tggtggaatc tcctgcagta ctggagtcag | 2400 |
| gaactaaaga atagtgctgt tagcttgctc aatgccacag ctatagcagt agctgagggg | 2460 |
| acagataggg ttatagaagt agtacaaaga gctgggagag ctattctcca catacctaga | 2520 |
| agaataagac agggcgcgga aagggctttg atataa | 2556 |

<210> SEQ ID NO 53
<211> LENGTH: 2577
<212> TYPE: DNA
<213> ORGANISM: Human immunodeficiency virus type 1

<400> SEQUENCE: 53

| | |
|---|---|
| atgagagtga aggagacaca gatgaattgg ccaaacttgt ggaaatgggg gactttgatc | 60 |
| attgggttgg tgataatttg tagtgcctcg gacaacctgt gggttacagt ttattatggg | 120 |
| gttcctgtgt ggagagatgc agataccacc ctattttgtg catcagatgc caaagcacat | 180 |
| gagacagaag tgcacaatgt ctgggccaca catgcctgtg tacccacaga ccccaaccca | 240 |
| caagaaatat acctagaaaa tgtaacagaa aattttaaca tgtggaaaaa taacatggtg | 300 |
| gagcagatgc aggaggatgt aatcagctta tgggatcaaa gtctaaagcc atgtgtaaag | 360 |
| ttaactcctc tctgcgttac tttaacttgt accaatgcta ctgcgaaaaa cataaccaat | 420 |
| ttctctaaca taacaggaac tataacagat gaagtaagaa actgttcttt taatatgacc | 480 |
| acagaaataa gagataagca gcagaaggtc catgcacttt tttataagct tgatttagta | 540 |
| caaatggaag gtagtaatag tagtaaaggt agtaatagta gtgagtatag gttaataaat | 600 |

```
tgtaatactt cagtcattaa gcaggcttgt ccaaagatat cctttgatcc aattcctata       660
cattattgta ctccagctgg ttatgcgatg ttaaagtgta atgataggaa tttcaatggg       720
acagggccat gtaacaatgt cagctcagta caatgcacac atggaattaa gccagtggta       780
tcaactcaat tgctgttaaa tggtagtcta gcagaagaag ataataat cagatctgag         840 aatctcacaa acaatgccaa aaccataata gtgcaccta ataaatctgt agaaatcaat        900
tgtaccagac cctccaacaa tataagaaga agtataacta taggaccagg acaagtattc       960
tataaaacag gaagcataat gggagatata agaaaagcat attgtgagat taatggaaca      1020
aaatggtacg aagctttaaa aaaggtaaag gaaagattag aagagcactt tactaataag      1080 acaataaccct ttcaaccacc ctcaggagga gatctagaga ttacaatgca tcattttaat     1140
tgtagagggg aattttccta ttgcaataca acacaactgt ttaataatac ctgcatagga      1200
aataaaacgt gtaatagcac tatcacactt ccatgcaaga taaagcaaat tataaacatg      1260
tggcagggag taggacaagc aatgtatgct cctcccatca gtggaaaaat taattgtgta      1320
tcaaatatta caggaatact attgacmaga gatggtggtg ctaataataa tacgaatgac      1380
gagaccttca gacctgggg aggaaatata aaggacaatt ggagaagtga attatataaa       1440
tataaagtag tagaaattga accactagga atagcaccca ccagggcaaa gagaagagtg      1500
gtggagagag aaaaaagagc agtgggaata ggagctgatga tctttgggtt cttaggagca    1560
gcaggaagca ctatgggcgc ggcgtcaata acgctgacgg tacaggccag acaattattg      1620
tctggtatag tgcaacagca aagcaatttg ctgagggcta tagaggcgca gcagcatatg     1680
ttgcaactca cagtctgggg cattaaacag ctccaggcaa gagtcctggc tgtggaaaga     1740
tacctaaagg atcaaaagtt cctaggactt tgggctgctc tgggaaaac catctgcacc       1800 actgctgtgc cctggaactc cacttggagt aataaatctt ttgaagagat ttggaacaac     1860
atgacatgga tagaatggga gagagaaatt agcaattata caagccaaat atttgagata     1920
cttacagaat cgcagaacca gcaggaaagg aatgaaaagg atttgttaga attggataaa     1980
tgggcaagtc tgtggaattg gtttgacata acaaagtggc tgtggtatat aaaaatatttt    2040 ataatgatag taggaggttt aataggttta agaataattt ttgctgtgct ttctatagta     2100
aatagagtta ggcagggata ctcacctttg tctttccaga cccctaccca tcatcagagg     2160
gaacccgaca gacccgaaag aatcgaagaa gaaggtggcg agcaaggcag agacagatcc     2220
gtgcgattag tgagcggatt cttagcactt gcctgggacg atctacgag cctgtgcctc      2280 ttcagctacc accgcttgag agacttcatc ttgattgcag cgaggactgt ggaacttctg     2340
ggacacagca gcctcaaggg actgagacgg gggtgggaag gcctcaaata tctgggaat     2400 cttctggtat attggggcca ggaactaaaa attagtgcta tttctttgct tgatgctaca     2460
gcaatagcag tagcggggcg gacagatagg gttatagaag tagcacaagg agcttggaga     2520
gccattctcc acatacctag aagaatcaga cagggcttag aaagggctttt gctataa       2577

<210> SEQ ID NO 54
<211> LENGTH: 2556
<212> TYPE: DNA
<213> ORGANISM: Human immunodeficiency virus type 1

<400> SEQUENCE: 54
atgagagtga aggggataca gaagaattgg caacacttat ggaaatgggg aactttgatc         60
cttgggttgg tgatagtttg tagtgcctca aataacctgt gggtcacagt ctattatggg        120
gtgcctgtgt gggaagatgc agataccatt ctattttgtg catctgatgc taaagcctat        180
```

```
agtactgaaa agcataatgt ctgggctaca catgcctgtg tacccacaga ccccaaccca    240
caagaaataa ctctggaaaa tgtaacagaa aaatttaata tgtgggacaa tcacatggta    300
gaccagatga atgaggatat aatcagttta tgggatgaaa gcctaaagcc atgtgtaaaa    360
ctgacccctc tctgtgttac tttgagttgt actaacgtaa caaaaaacag tactgcaaac    420
aatggcactg tagatgacaa ataggaatg aaaaactgct cttttaatat aaccacagaa    480
ataagagata agaaaaagac agaatacgcg cttttctata aacttgacat agagccaatt    540
gataaaaatg atactactta tagattaata aattgtaatg tctcaaccat taaacaggct    600
tgtccaaagg tgacttttga accaatcccc atacattatt gtgctccagc tggttttgcg    660
attctaaagt gtagggatag gaacttcaat ggaacaggac tatgtaaaaa tgtcagtaca    720
gtacaatgca cacatggaat caagccagta gtgtcaactc aactgctgtt gaatggcagc    780
ctagcagaag gagatgtaat gattagatct gaaaatctca cagacaataa aaaaatcata    840
atagtacagt ttaatgagtc tgtaagcatt aattgtacca gacccaacaa caatacaagg    900
agaagtgtac atatagcacc aggacaagca ttctatgcaa caggtgacat aatagggat    960 ataagacaag cacattgtaa tgtcagtgaa tcaaaatgga atgagatgtt acaaaaggta   1020
gctgtacagt taagacaaca ctttaacaaa acagcaataa aatttactaa ctcctcagga   1080
ggggatttag aaattacaac acatagtttt aattgtggag gagaattttt ctattgcaat   1140
acatcaggtc tgtttaatag tacttggtat cggaatggca ctgccatcag gcagaacggc   1200
acggggttaa atgatactat aactctccca tgcagaataa ggcaaattgt acgtacatgg   1260
cagagagtag gacaagcaat gtatgcccct cccattcaag gagtaataaa atgtgaatca   1320
aacattacgg ggctactgtt aacaagagat ggtgggaata atagtagtaa taatgacact   1380
gagaccttca gacctggagg aggagatatg gaagacaatt ggagaagtga attatacaac   1440
tataaggtag taaaaattaa accattagga atagcaccca ccaaggcaag gagaagagta   1500
gtggggagag agaaaagagc agttggactg ggagctgttt tccttgggtt cttagggaca   1560
gcaggaagca ctatgggcgc agcgtcaata acgctgacgg tacaggtcag acaattattg   1620
tctggcatag tgcaccagca aagcaatttg ctgagagcta tagaggcgca gcagcatctg   1680
ttgcagctca cagtctgggg cattaaacag ctccaggcaa gagtcctggc gttagaaaga   1740
tacctaaagg atcaacagct cctaggaatt tggggctgct ctggaaaact catctgcccc   1800
actaatgtgc cctggaatgc tagttggagt aataaaactt ttaatgaaat ttgggataac   1860
atgacctgga tagaatggga tagggaaatt aacaattaca cacaacaaat atacagacta   1920
attgaagaat cgcaaggtca gcaggaaaag aatgaacaag acttattggc attggacaaa   1980
tgggcaagtc tgtggaattg gtttgacata tcaaactggc tatggtacat aagaatattt   2040
ataatgatag taggaggctt aataggttta agaatagttt ttgctgtgct ttctatagtc   2100
aatagagtta ggcagggcta ctcacccttg tcgttgcaga cccttatccc aaacccaacg   2160
ggagccgaca ggcccggaga atcgaagaa ggaggtggag agcaaggcag aaccagatcg   2220
attcgattgg tggacagatt cttagcactt gcctgggacg acctacgag cctgtgcctt   2280 tgcagctacc accgattgag agacttcgtc ttgattgcag cgaggactgt ggaaactctg   2340
ggacgcaggg ggtgggagat cctcaaatac ctggggaacc tagtatggta ttgggacag   2400 gaactaaaga atagtgctat taatttagtt gatacaatag caatagcagt agctaactgg   2460
acagataggg ttatagaagt aatacaaaga gttgttagag cttttctgca catacctaga   2520
agaataagac aaggctttga gagagctttg ctataa                             2556
```

-continued

```
<210> SEQ ID NO 55
<211> LENGTH: 7
<212> TYPE: PRT
<213> ORGANISM: Human adenovirus type 1
<220> FEATURE:
<221> NAME/KEY: MISC_FEATURE
<222> LOCATION: (3)..(3)
<223> OTHER INFORMATION: The 'Xaa' at location 3 stands for Asp or Gly.
<220> FEATURE:
<221> NAME/KEY: MISC_FEATURE
<222> LOCATION: (4)..(4)
<223> OTHER INFORMATION: The 'Xaa' at location 4 stands for Thr or Lys.
<220> FEATURE:
<221> NAME/KEY: MISC_FEATURE
<222> LOCATION: (6)..(6)
<223> OTHER INFORMATION: The 'Xaa' at location 6 stands for Ala or Asp.
<220> FEATURE:
<221> NAME/KEY: MISC_FEATURE
<222> LOCATION: (7)..(7)
<223> OTHER INFORMATION: The 'Xaa' at location 7 stands for Ser or Asn.

<400> SEQUENCE: 55

Thr Leu Xaa Xaa Trp Xaa Xaa
1               5
```